(12) United States Patent
Bandy et al.

(10) Patent No.: US 9,173,592 B2
(45) Date of Patent: Nov. 3, 2015

(54) METHODS AND SYSTEMS FOR ACOUSTIC DATA TRANSMISSION

(71) Applicant: Innurvation, Inc., Columbia, MD (US)

(72) Inventors: William Robert Bandy, Gambrills, MD (US); Roger Allen Davenport, Plantation, FL (US); Yuri Okunev, Middle Island, NY (US)

(73) Assignee: INNURVATION, INC., Columbia, MD (US)

( * ) Notice: Subject to any disclaimer, the term of this patent is extended or adjusted under 35 U.S.C. 154(b) by 0 days.

(21) Appl. No.: 13/969,979

(22) Filed: Aug. 19, 2013

(65) Prior Publication Data

US 2014/0200418 A1 Jul. 17, 2014

Related U.S. Application Data

(63) Continuation of application No. 11/896,946, filed on Sep. 6, 2007, now Pat. No. 8,512,241.

(60) Provisional application No. 60/941,184, filed on May 31, 2007, provisional application No. 60/842,360, filed on Sep. 6, 2006.

(51) Int. Cl.
| | |
|---|---|
| *A61B 5/07* | (2006.01) |
| *H03G 5/00* | (2006.01) |
| *A61B 19/00* | (2006.01) |
| *A61B 1/00* | (2006.01) |
| *A61B 1/04* | (2006.01) |
| *A61B 5/00* | (2006.01) |
| *A61B 8/08* | (2006.01) |
| *A61B 8/00* | (2006.01) |

(52) U.S. Cl.
CPC ............ *A61B 5/073* (2013.01); *A61B 1/00016* (2013.01); *A61B 1/041* (2013.01); *A61B 5/0022* (2013.01); *A61B 5/0028* (2013.01); *A61B 5/411* (2013.01); *A61B 5/6861* (2013.01); *A61B 8/0833* (2013.01); *A61B 8/4236* (2013.01); *A61B 8/56* (2013.01); *A61B 8/565* (2013.01); *A61B 1/00036* (2013.01); *A61B 5/42* (2013.01)

(58) Field of Classification Search
CPC ............ A61B 5/70; A61B 1/16; A61B 1/41; A61B 5/22; A61B 5/28; A61B 5/411; A61B 5/6861; A61B 8/833; A61B 8/56; A61B 8/565; A61B 8/4236; A61B 1/36; A61B 5/42
See application file for complete search history.

*Primary Examiner* — Reza Ghafoorian
(74) *Attorney, Agent, or Firm* — Sterne, Kessler, Goldstein & Fox P.L.L.C.

(57) ABSTRACT

A method of communicating with an ingestible capsule includes detecting the location of the ingestible capsule, focusing a multi-sensor acoustic array on the ingestible capsule, and communicating an acoustic information exchange with the ingestible capsule via the multi-sensor acoustic array. The ingestible capsule includes a sensor that receives a stimulus inside the gastrointestinal tract of an animal, a bidirectional acoustic information communications module that transmits an acoustic information signal containing information from the sensor, and an acoustically transmissive encapsulation that substantially encloses the sensor and communications module, wherein the acoustically transmissive encapsulation is of ingestible size. The multi-sensor array includes a plurality of acoustic transducers that receive an acoustic signal from a movable device, and a plurality of delays, wherein each delay is coupled to a corresponding acoustic transducer. Each delay may be adjusted according to a phase of a signal received by the corresponding acoustic transducer.

20 Claims, 38 Drawing Sheets

FIRST LOGIC VALUE

SECOND LOGIC VALUE

THIRD LOGIC VALUE

FOURTH LOGIC VALUE

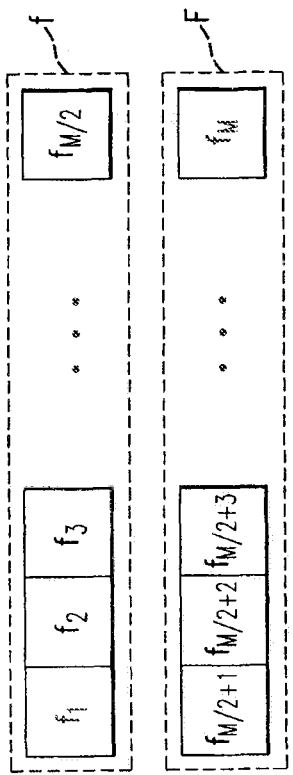

FIG. 39B

METHODS AND SYSTEMS FOR ACOUSTIC DATA TRANSMISSION

CROSS-REFERENCE TO RELATED APPLICATIONS

The present application is a continuation of U.S. patent application Ser. No. 11/896,946, filed Sep. 6, 2007, now U.S. Pat. No. 8,512,241, which claims the benefit of U.S. Provisional Patent Appl. No. 60/842,360, filed Sep. 6, 2006, and U.S. Provisional Patent Appl. No. 60/941,184, filed May 31, 2007, each of which is incorporated by reference herein in its entirety.

BACKGROUND OF THE INVENTION

1. Field of the Invention

The present invention generally relates to data transmission in a communication system, and more specifically to acoustic data transmission involving an ingestible capsule.

2. Related Art

The surface between the animal body and air is almost a perfect acoustic reflector. Therefore, the animal body is an acoustic reverberation chamber, where sound launched into and within the body echoes back and forth between these surfaces until attenuation causes the sound to die out. Other materials in the body such as lungs, gas pockets, bone, etc., cause reflections which further add to the effect of a reverberation chamber. Attenuation is linearly dependent upon frequency, with higher frequencies having greater attenuation. For example, a 500 KHz acoustic pulse launched within the body will take almost 200 microseconds for the echoing to die out, while a 1 MHz pulse would take only 100 microseconds, and a 100 KHz pulse echo would not die out until a millisecond has passed.

The body is not a static fixed cavity resonator, but rather is a dynamic one, with the echo characteristics changing with time. Many factors affect the dynamic behavior of this reverberation chamber, including breathing, the heart beat, speaking, organ movement, bowel function, vein pulsing, body movement, and even Doppler frequency shifting. The result is that an acoustic signal source (modulation at a given frequency or set of frequencies) in the body will create a noise signal which is a complicated function of the multiple echoes of all previously sent frequencies and which is amplitude modulated and phase shifted by the differences in tissue densities and dynamic changes of the body cavity. A modulation is a change to a carrier frequency, which includes a change from a constant wave to a reduced amplitude constant wave as is used typically to transfer both power and data communications. The complex noise signal in the acoustic communication channel makes high data rate information transfer a difficult challenge within the body as it is difficult for the receiver, attached to the skin of the body, to distinguish a signal transmitted by an ingestible diagnostic capsule from this additional noise signal that will accompany the intended signal. Low data rates are achieved simply by waiting until the noise dies out before sending another data bit or symbol which can be unambiguously identified by the receiver. However, to achieve high data rates, data bits or symbols need to be pushed through the channel in the presence of the noise. Therefore, what is needed is a method and apparatus that may achieve high data rates by pushing data bits or symbols through the channel in the presence of the noise.

BRIEF SUMMARY OF THE INVENTION

In one embodiment, a method of communicating with an ingestible capsule includes selecting one or more carrier frequencies associated with one or more frequency channels based on a hopping pattern. Data from the ingestible capsule is encoded base upon the one or more carrier frequencies. The encoded data is then acoustically transmitted through a body of an animal. If encoding includes generating one or more delay intervals based on the data, transmitting may include transmitting a first carrier frequency associated with a first frequency channel, waiting the one or more delay intervals, and then transmitting a second carrier frequency associated with a second frequency channel. Encoding may include embedding one or more phases of the one or more carrier frequencies into the one or more frequency channels. If selecting carrier frequencies includes dividing the carrier frequencies into one or more sets of carrier frequencies, encoding may include, for example and without limitation, embedding a carrier frequency into one or more frequency channels and/or embedding one or more phases of the frequencies into one or more frequency channels.

In another embodiment, a method of communicating with an ingestible capsule includes acoustically receiving encoded data from a body of an animal. One or more carrier frequencies associated with one or more frequency channels is selected based on a hopping pattern. The encoded data is then decoded based upon the one or more carrier frequencies. If decoding includes measuring one or more delay intervals based on the data, receiving may include receiving a first carrier frequency associated with a first frequency channel, waiting the one or more delay intervals, receiving a second carrier frequency associated with a second frequency channel. Decoding may include detecting one or more phases of carrier frequencies in one or more frequency channels. If selecting frequencies includes dividing the frequencies into sets of carrier frequencies, decoding may include, for example and without limitation, detecting a carrier frequency from sets of carrier frequencies in one or more frequency channels and/or detecting one or more phases of the frequencies in the frequency channels.

These and other advantages and features will become readily apparent in view of the following detailed description of the invention. Note that the Summary and Abstract sections may set forth one or more, but not all exemplary embodiments of the present invention as contemplated by the inventor(s).

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

Figure 29A:
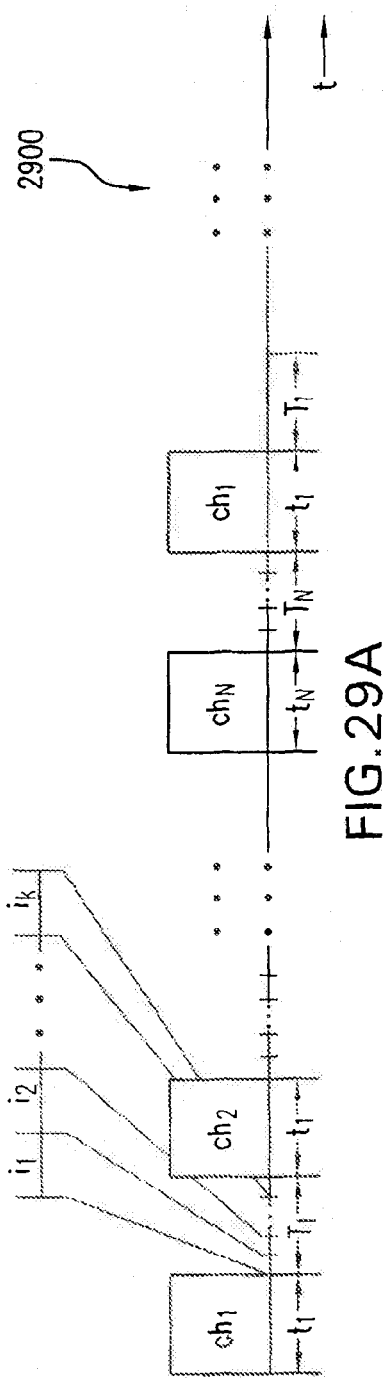
FIG. 29A illustrates a combined FH and pulse interval encoding (PIE) scheme to encode and/or decode an acoustic communication signal according to an exemplary embodiment of the present invention.
Figure 29A:
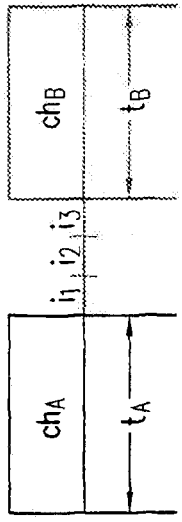
Figure 29A:
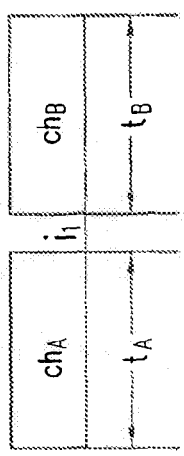
Figure 29B:
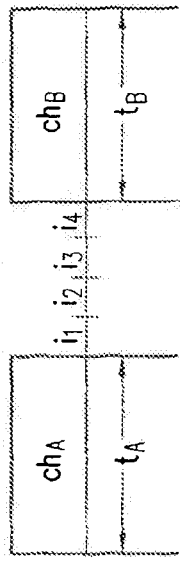
Figure 29B:
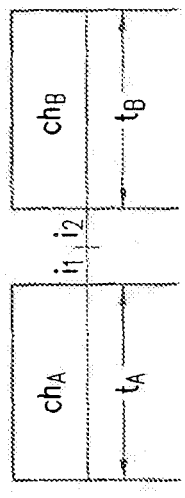

FIG. 29B further illustrates the combined FH and PIE scheme according to an exemplary embodiment of the present invention.

Figure 30A:
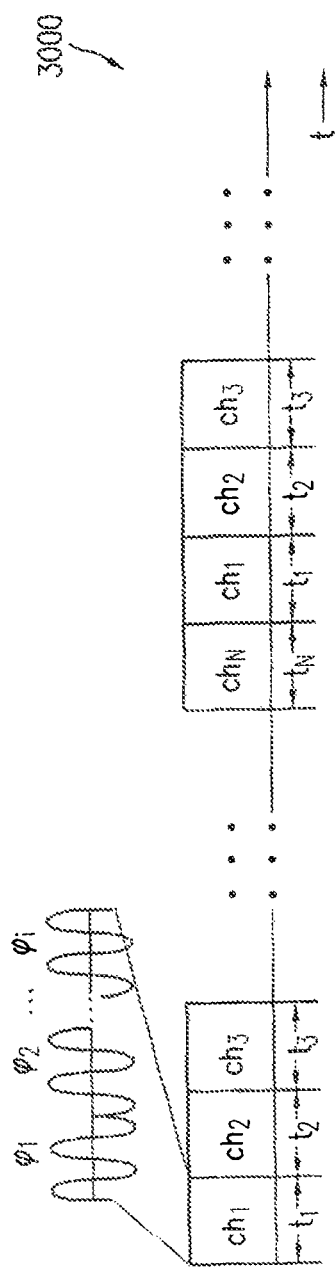

FIG. 30A illustrates a combined FH and differential phase shift keying (DPSK) scheme to encode and/or decode an acoustic communication signal according to an exemplary embodiment of the present invention.

Figure 30B:
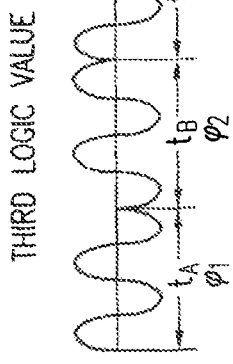
Figure 30B:
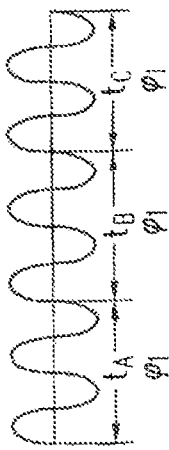
Figure 30B:
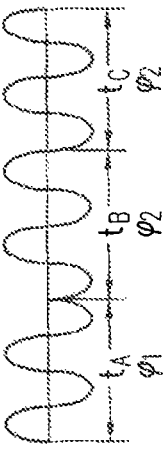
Figure 30B:
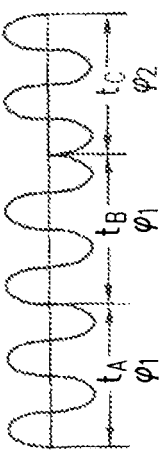

FIG. 30B further illustrates the combined FH and DPSK scheme according to an exemplary embodiment of the present invention.

Figure 31:
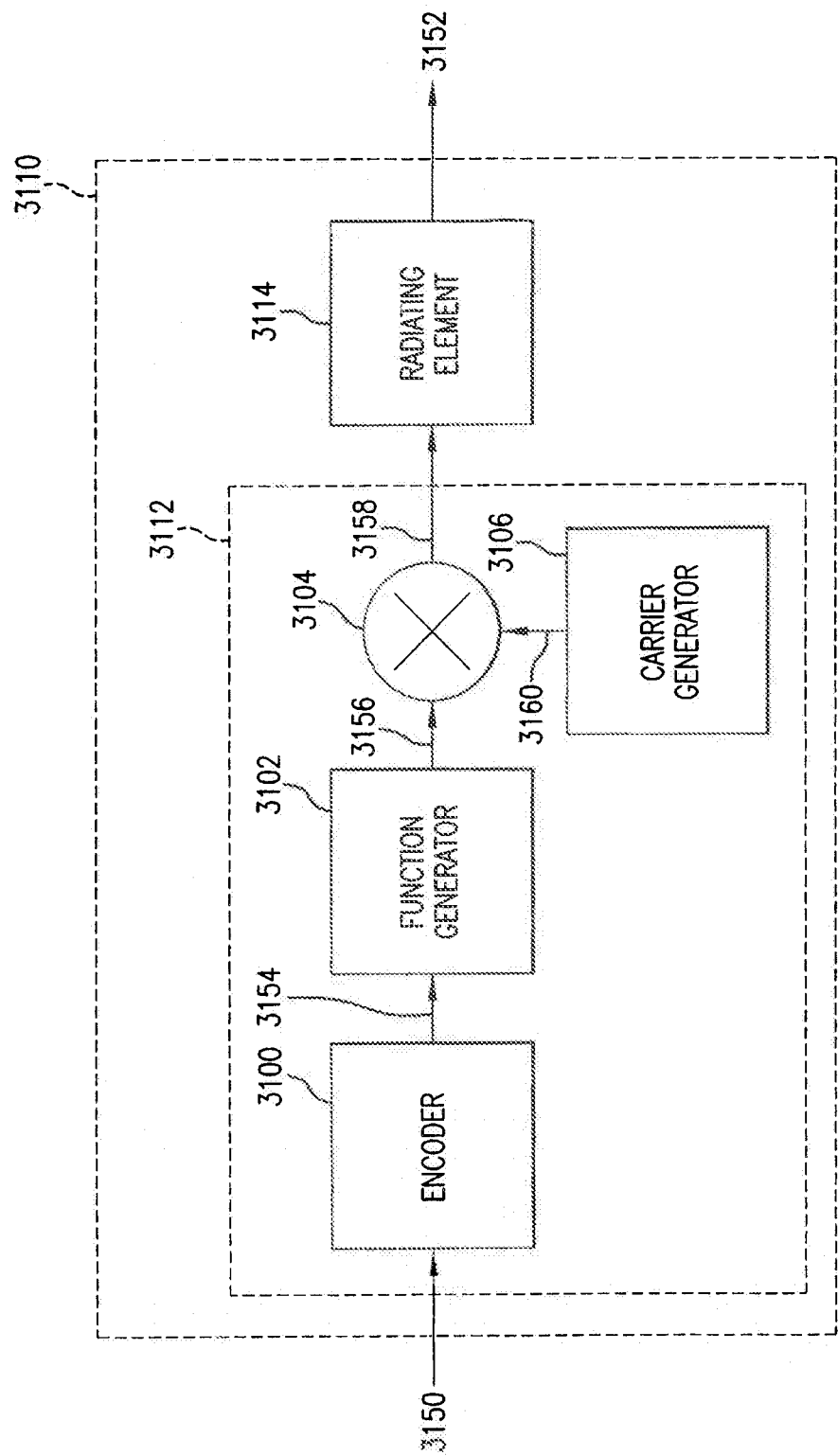

FIG. 31 illustrates a block diagram of a transmitter to encode an information signal using a combined FH and DPSK scheme according to an exemplary embodiment of the present invention.

Figure 32:
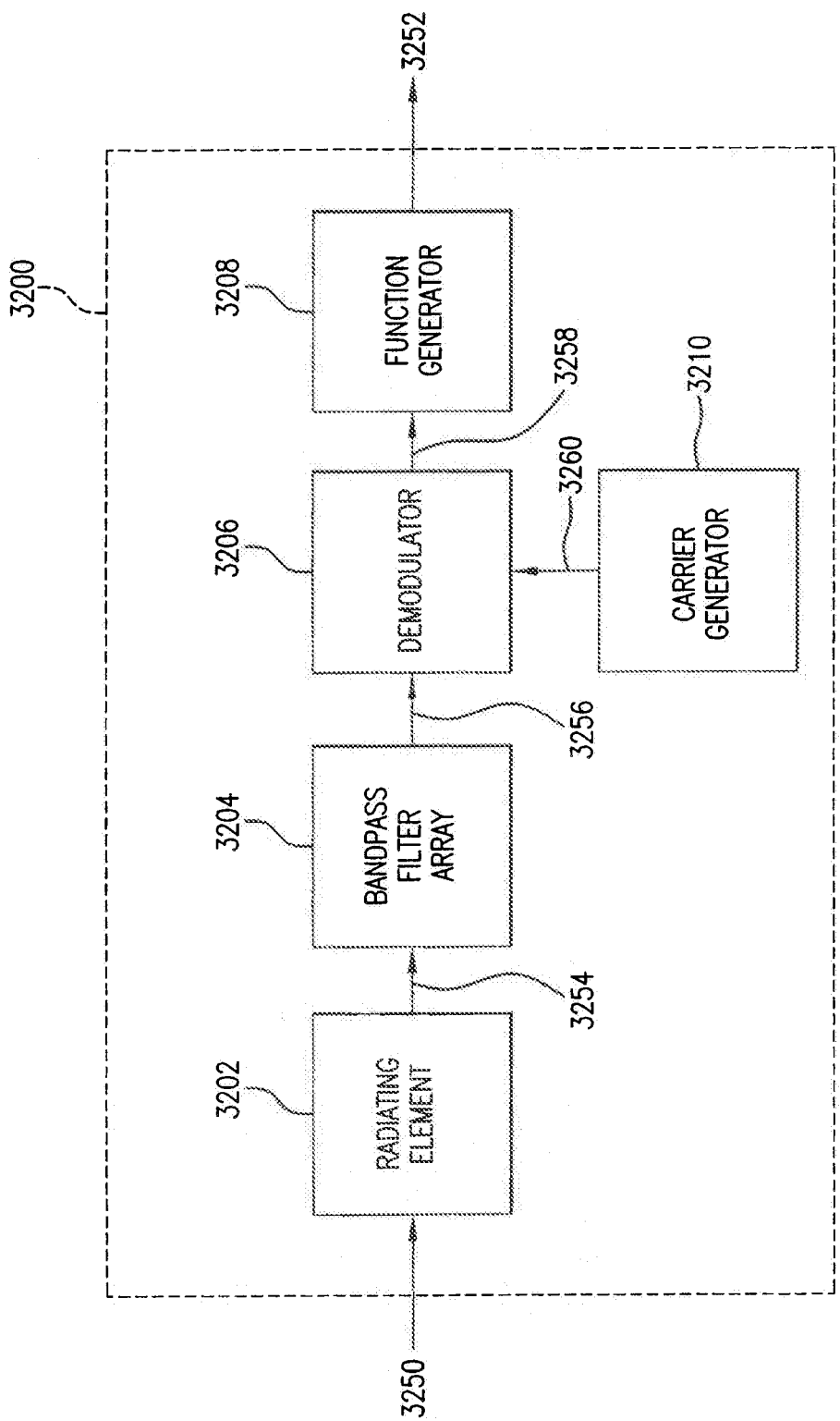

FIG. 32 illustrates a block diagram of a receiver to decode an acoustic communication signal using a combined FH and DPSK scheme according to an exemplary embodiment of the present invention.

Figure 33A:
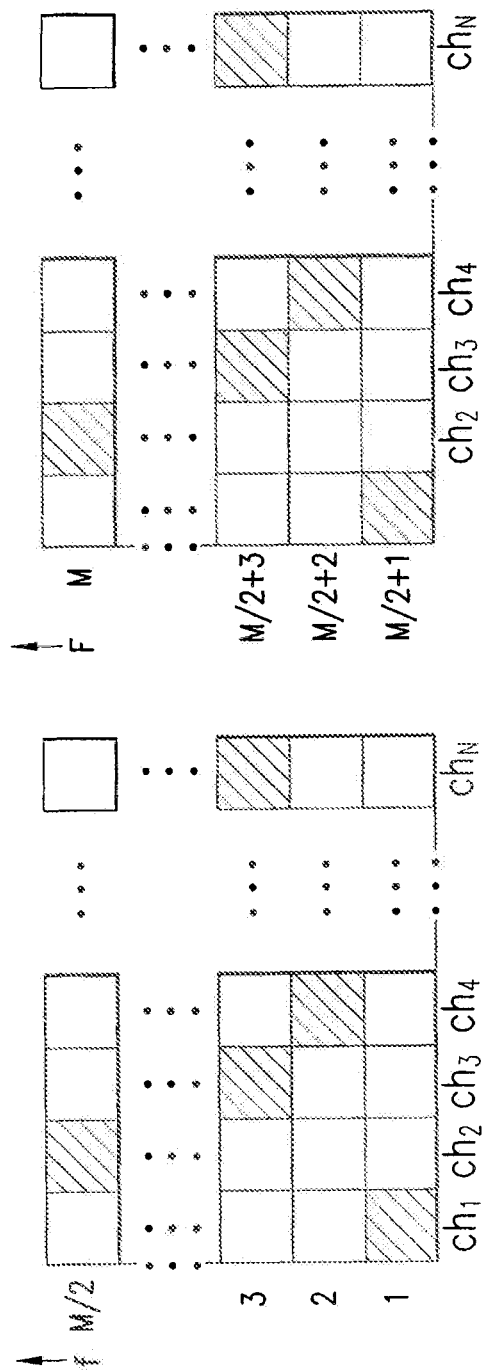

FIG. 33A illustrates a hopping pattern used to encode and/or decode an acoustic communication signal using a combination of FH and differential frequency shift keying (DFSK) according to an exemplary embodiment of the present invention.

FIG. 33B further illustrates the hopping pattern used to encode and/or decode the acoustic communication signal using the combination of FH and DFSK according to an exemplary embodiment of the present invention.

FIG. 33C illustrates a combined FH and DFSK scheme to encode and/or decode an acoustic communication signal according to an exemplary embodiment of the present invention.

Figure 34A:
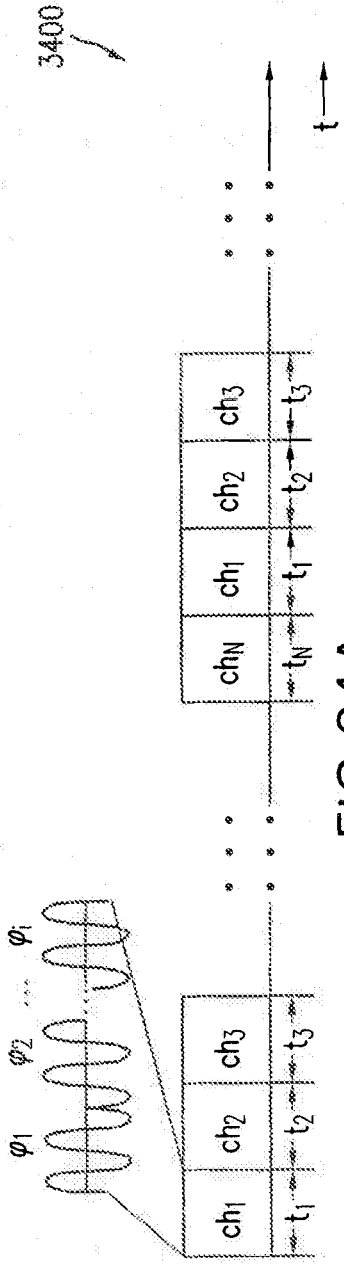

FIG. 34A illustrates a combined FH, DFSK, and DPSK scheme to encode and/or decode an acoustic communication signal according to an exemplary embodiment of the present invention.

Figure 34B:
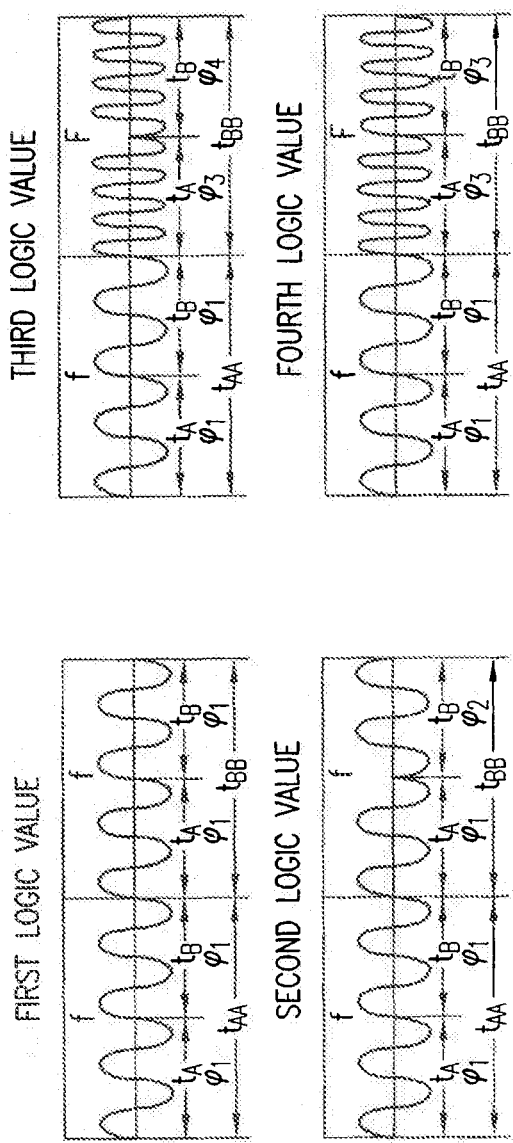

FIG. 34B further illustrates the combined FH, DFSK, and DPSK scheme according to an exemplary embodiment of the present invention.

Figure 34C:
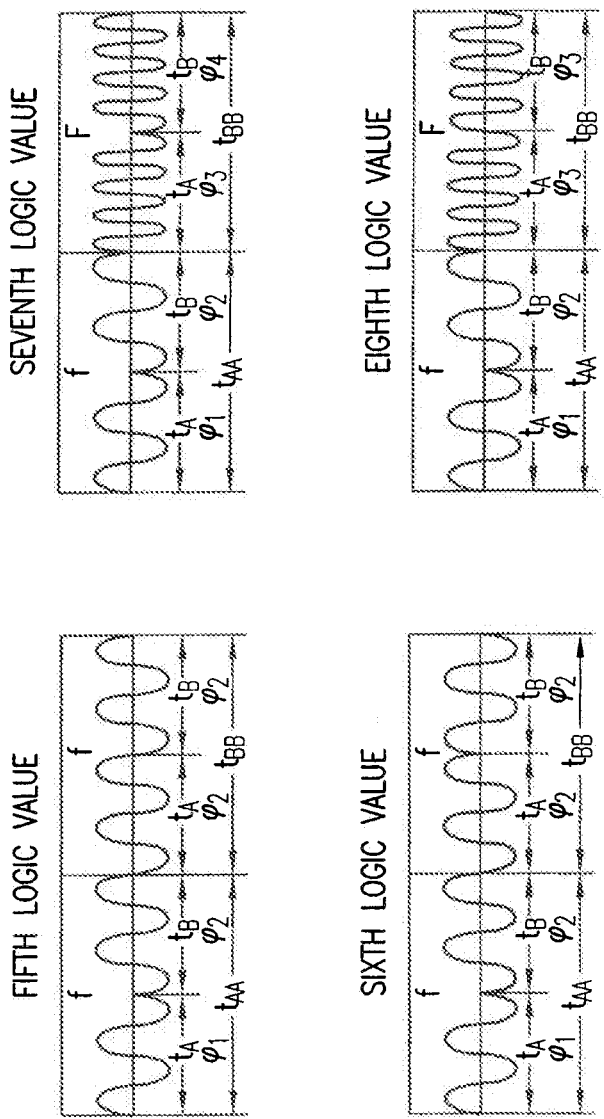

FIG. 34C further illustrates the combined FH, DFSK, and DPSK scheme according to an exemplary embodiment of the present invention.

Figure 35:
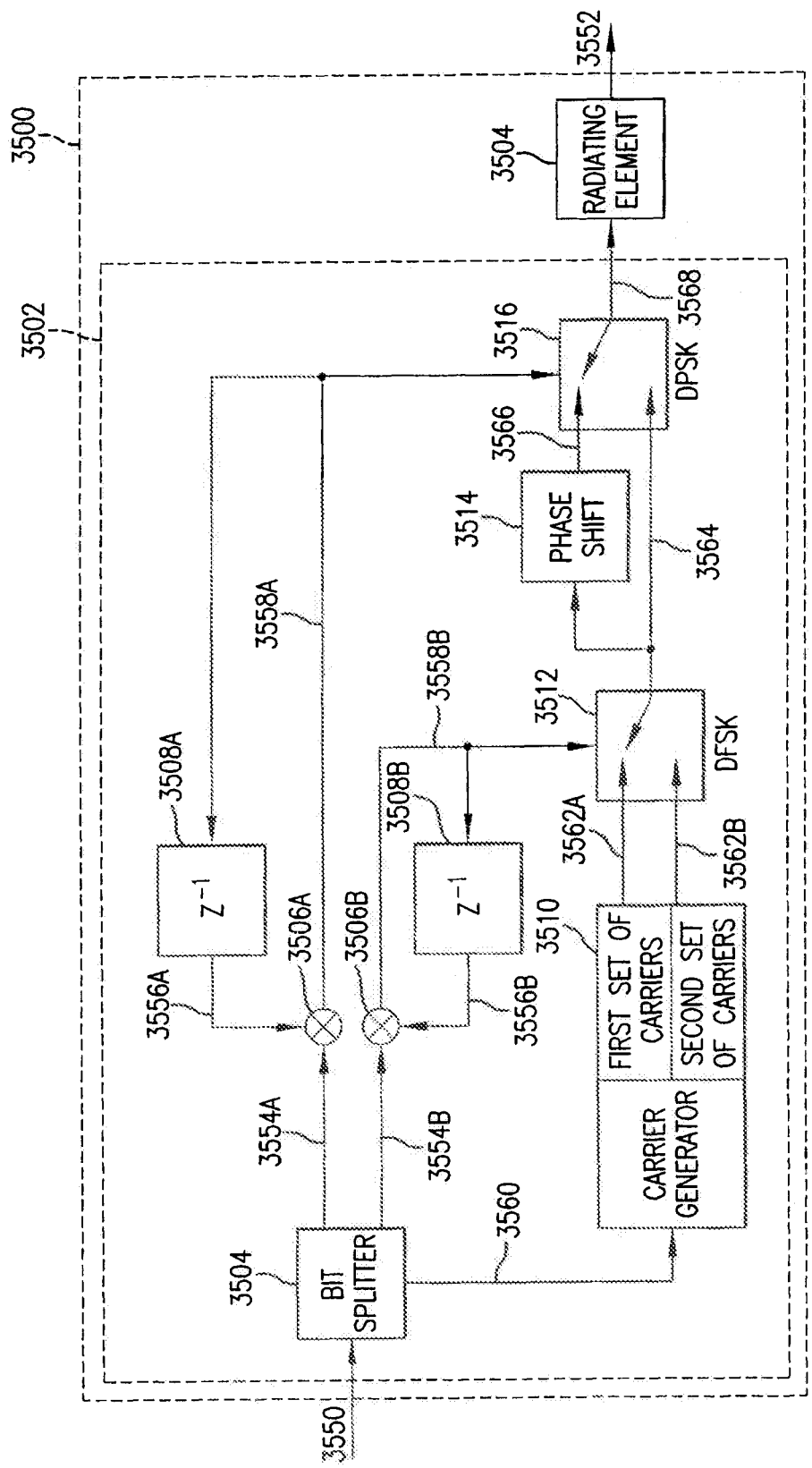

FIG. 35 illustrates a block diagram of a transmitter to encode an information signal to a combination of FH, DFSK and DPSK acoustic communication signal according to an exemplary embodiment of the present invention.

Figure 36:
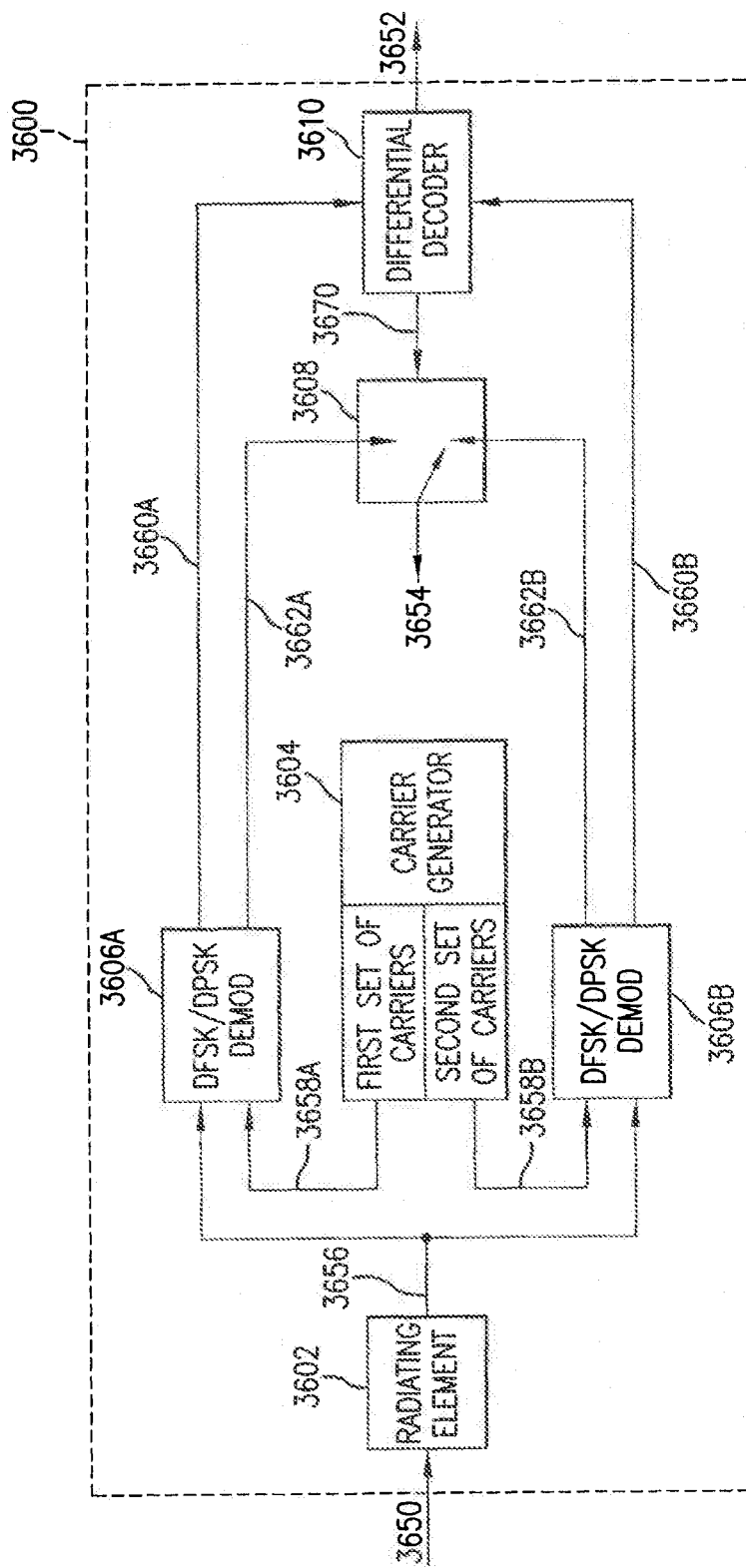

FIG. 36 illustrates a block diagram of a receiver to decode an information signal from an acoustic communication signal encoded using a combination of FH, DFSK and DPSK according to an exemplary embodiment of the present invention.

Figure 37:
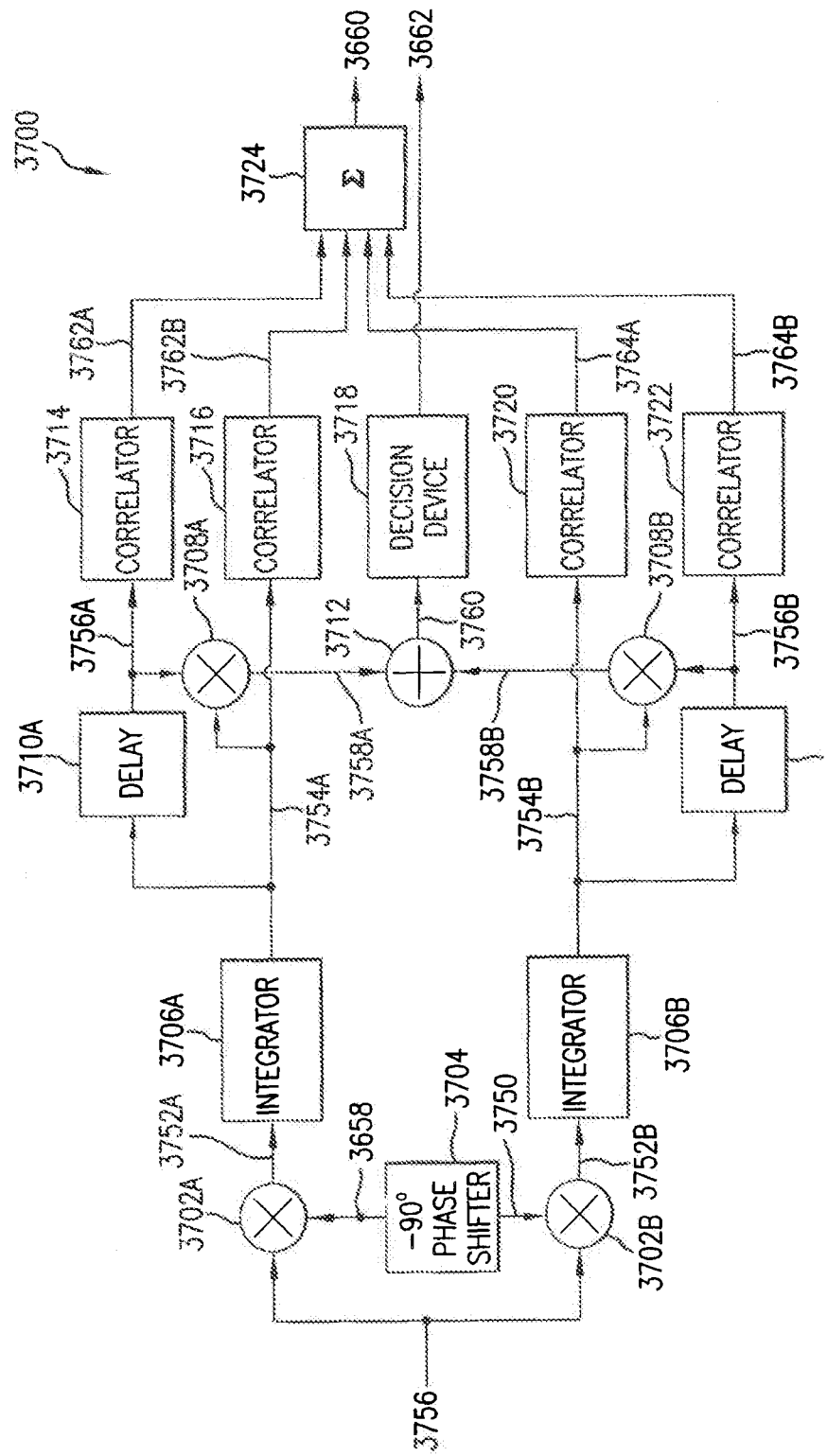

FIG. 37 illustrates a block diagram of a demodulator to decode an information signal from an acoustic communication signal encoded using a combination of FH, DFSK, and DPSK according to an exemplary embodiment of the present invention.

Figure 38:
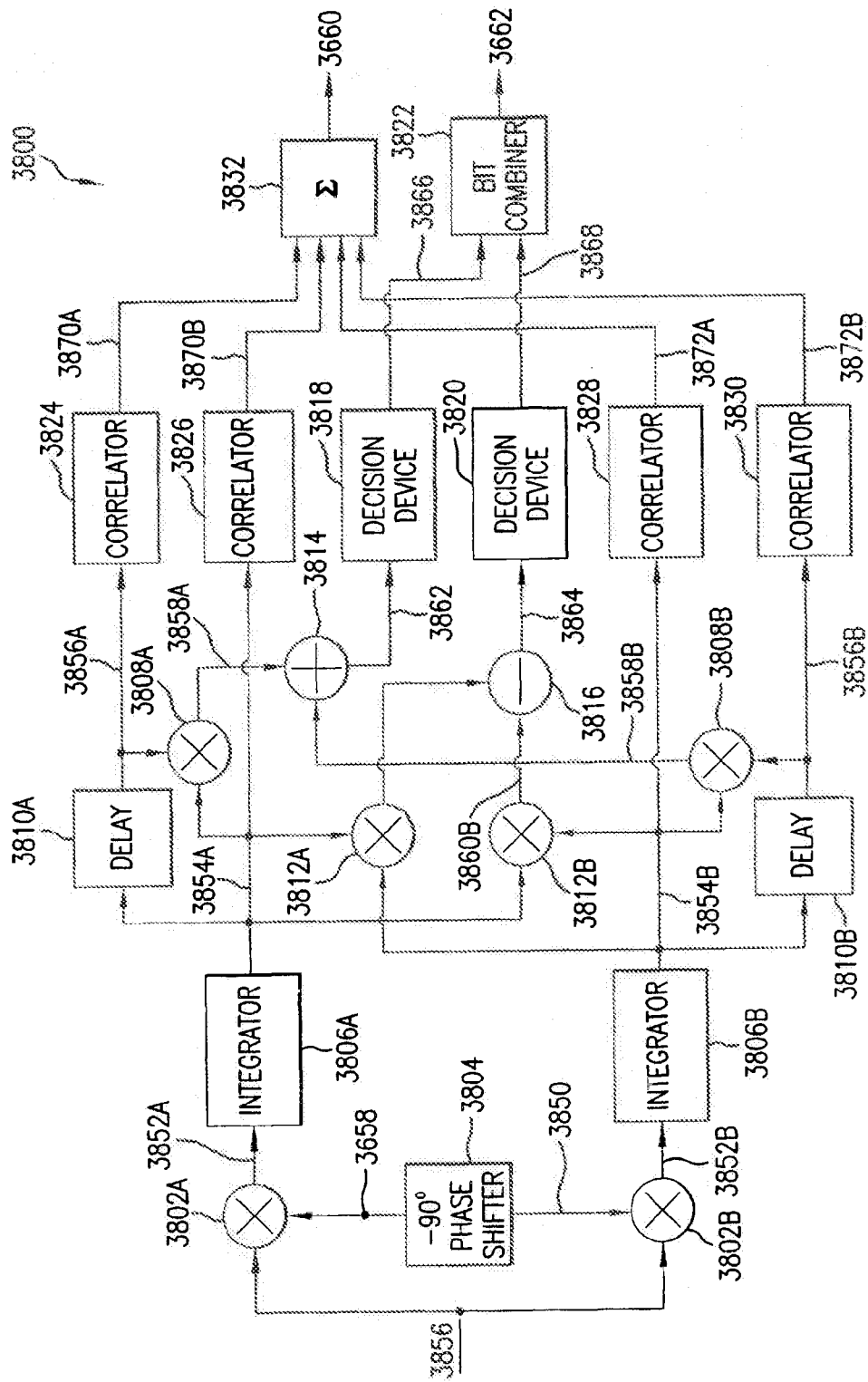

FIG. 38 illustrates a block diagram of a demodulator to decode an information signal from an acoustic communication signal encoded using a combination of FH, DFSK, and DPSK according to another exemplary embodiment of the present invention.

Figure 39A:
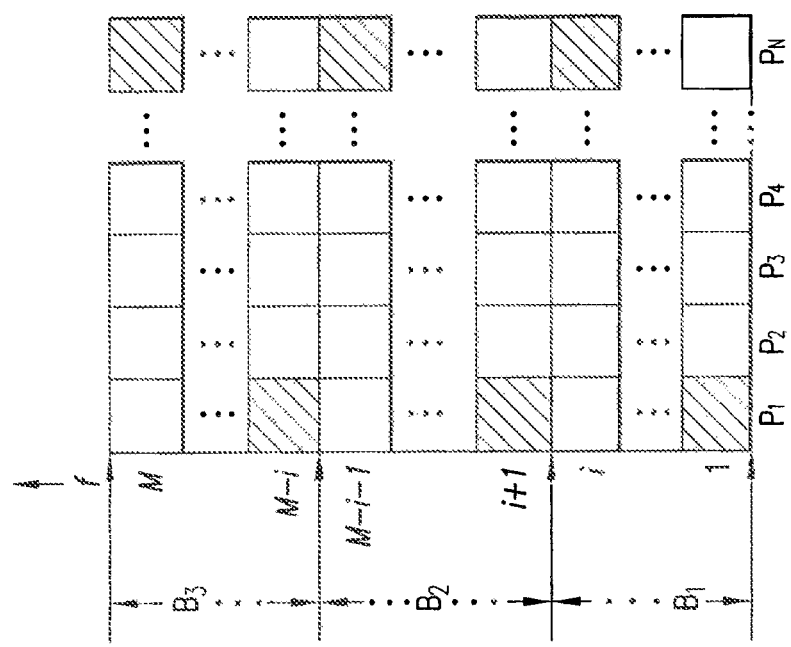

FIG. 39A illustrates a hopping pattern used to encode and/or decode an acoustic communication signal using multiple frequency bands with FH according to an exemplary embodiment of the present invention.

Figure 39B:
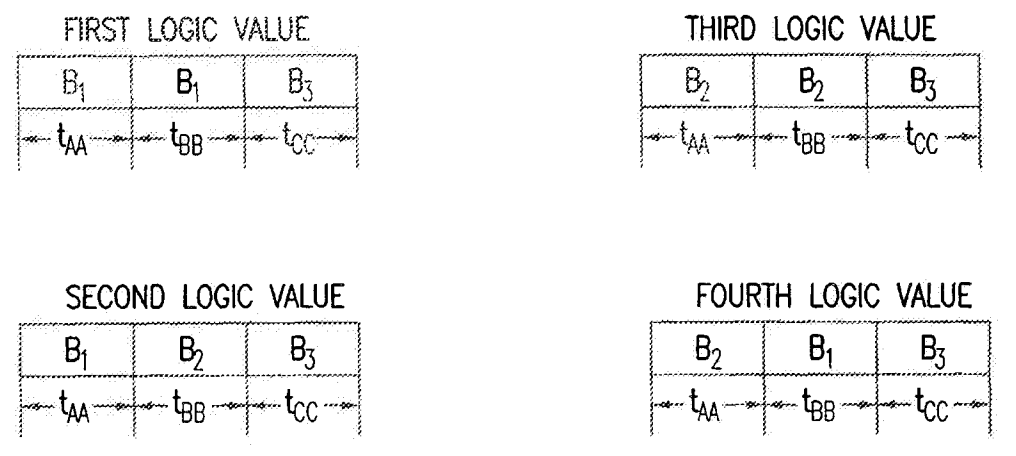

FIG. 39B illustrates a multiple frequency band with FH scheme to encode and/or decode an acoustic communication signal according to an exemplary embodiment of the present invention.

Figure 39C:
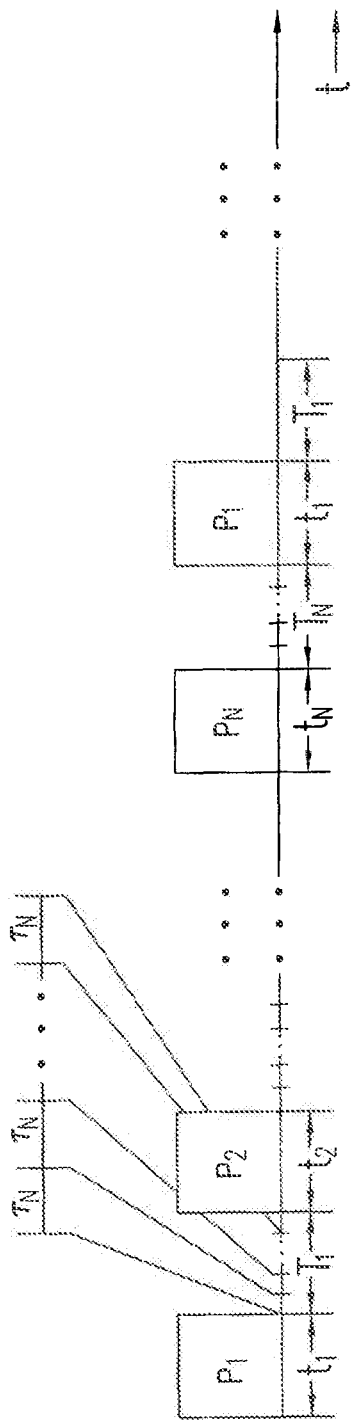

FIG. 39C illustrates a multiple frequency band with FH and time interval encoding scheme to encode and/or decode an acoustic communication signal according to an exemplary embodiment of the present invention.

Figure 39D:
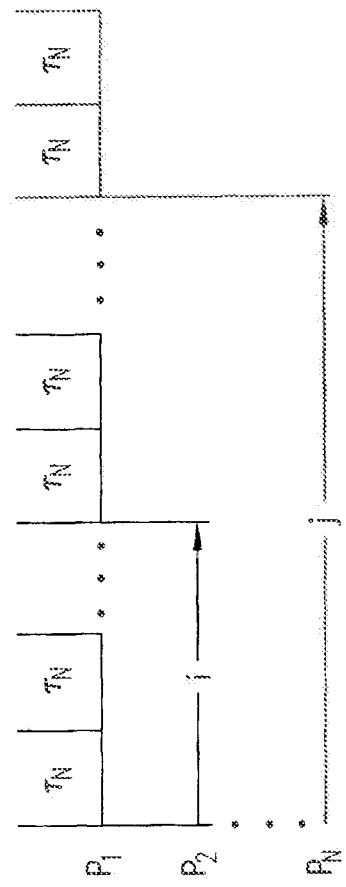

FIG. 39D illustrates an advancement function that may be used with the multiple frequency bands with FH and time interval encoding scheme according to an exemplary embodiment of the present invention.

The present invention will now be described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

I. Introduction

Methods, systems, and apparatuses for ingestible capsules are described. Furthermore, methods, systems, and apparatuses for operating and communicating with the ingestible capsules are also described. The present specification discloses one or more embodiments that incorporate the features of the invention. The disclosed embodiment(s) merely exemplify the invention. The scope of the invention is not limited to the disclosed embodiment(s). The invention is defined by the claims appended hereto.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner. Likewise, particular bit values of "0" or "1" (and representative voltage values) are used in illustrative examples provided herein to represent information for purposes of illustration only. Information described herein can be represented by either bit value (and by alternative voltage values), and embodiments described herein can be configured to operate on either bit value (and any representative voltage value), as would be understood by persons skilled in the relevant art(s).

The example embodiments described herein are provided for illustrative purposes, and are not limiting. Further structural and operational embodiments, including modifications/alterations, will become apparent to persons skilled in the relevant art(s) from the teachings herein.

Methods and systems for an ingestible capsule are described. The ingestible capsule may be swallowed by an animal to diagnose or aid in the diagnosis of one or more conditions of the animal through either an immediate detection or a historical and/or statistical analysis of multiple detections of conditions or attributes over a time period. Example embodiments are described below as related to a human subject, for illustrative purposes. However, embodiments of the present invention are applicable to further types of animals other than humans, including livestock (cattle, sheep, pigs, chickens, turkeys, ostriches, etc.), pets (e.g., dogs, cats, horses, etc.), and other animals of interest such as race horses or other performance/sport animals. Such applicability to these types of animals, and other types, will be apparent to persons skilled in the relevant art(s) from the teachings herein, and is within the scope and spirit of embodiments of the present invention.

Furthermore, example embodiments are described below as related to passing an ingestible capsule through a gastrointestinal tract, for illustrative purposes. However, embodiments of the present invention are applicable to further bodily systems other than the gastrointestinal tract, including the circulatory system, the urinary tract, and other bodily systems and additionally other means of entry or implant into a body cavity of an animal or human. Such applicability to other types of bodily systems will be apparent to persons skilled in the relevant art(s) from the teachings herein, and is within the scope and spirit of embodiments of the present invention.

II. Ingestible Acoustic Device

Figure 1:
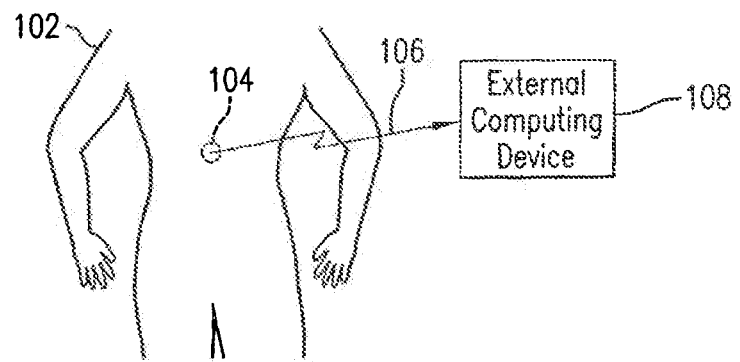
FIG. 1 illustrates a partial view of a human according to an embodiment of the present invention.

FIG. 1 shows a partial view of a human 102 according to an embodiment of the present invention. In FIG. 1, human 102 has swallowed or ingested an ingestible capsule 104. Ingestible capsule 104 is configured to sense one or more attributes or conditions of human 102 as ingestible capsule 104 passes through human 102. While passing through human 102, ingestible capsule 104 transmits information in a communication signal 106 to be received on the outside of the human 102. Ingestible capsule 104 may send information to and receive information from an external device, or it may be a beacon that only emits information to the external device. As shown in FIG. 1, an external computing device 108 may receive communication signal 106. Computing device 108 may be used to display the information received in communication signal 106, to interact with the information, to process the information, and/or to transmit the information (raw or processed) to another entity or component. In an embodiment, computing device 108 can interact with ingestible capsule 104 to control functions of ingestible capsule 104.

In a simplistic embodiment, computing device 108 may simply act as a protocol converter in a store and forward manner. However, in a more complex environment, computing device 108 may perform complex and intensive functions such as data normalization, compression, and encryption for example.

In another advanced embodiment, computing device 108 can interact with ingestible sensor device 104 to control functions of ingestible sensor device 104. This embodiment infers a bi-directional communication 106 with sensor device 104. Bi-directional communications are generally common place with persons skilled in the art. However, these designs are typically designed to be able to receive signals either at times not transmitting, or at all times. These common techniques are not desirable in the described environment as receivers require power, and additional power would consequently add to the size of sensor device 104. External computing device 108 receives and stores commands and/or information from a network. Upon termination of the next transmission from sensor device 104, sensor device 104 may turn on a receiver for a very short amount of time, while external device 108 commences transmission of commands or information to sensor device 104. Greatly reduced power requirements on sensor device 104 are gained from very rapidly turning off a receiver when no communications (or an indication of no information to communicate) are received from device 108 within a defined time window after a last transmission from sensor device 104.

In embodiments, human 102 may be provided with one or more ingestible capsules 104 that human 102 may at designated times and/or periodically swallow to perform an analysis of one or more health-related conditions of human 102. Multiple ingestible capsules 104 may interact with device 108 and/or each other. An exemplary ingestible capsule is described in U.S. Pat. No. 8,588,887, titled "Ingestible Low Power Sensor Device and System for Communicating with Same," which is incorporated by reference herein in its entirety.

Figure 2:
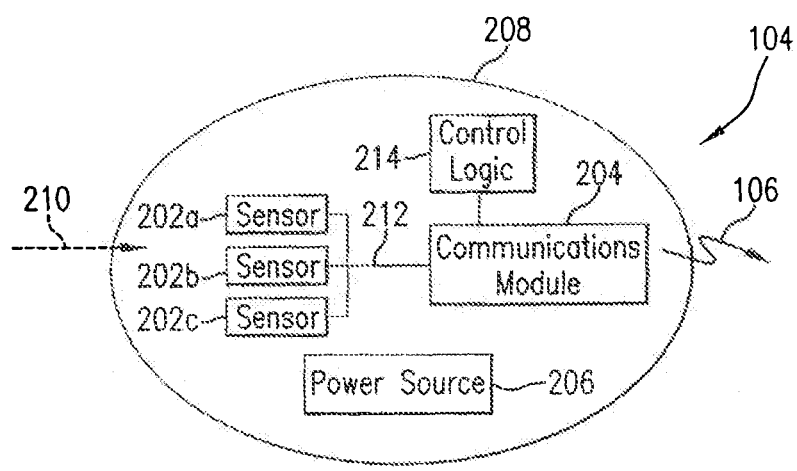
FIG. 2 is a block diagram of an ingestible capsule according to an embodiment of the present invention.

FIG. 2 shows an example block diagram of ingestible capsule 104, according to an embodiment of the present invention. In FIG. 2, ingestible capsule 104 includes an acoustically transmissive encapsulation 208 that holds one or more sensors 202, a communications module 204, and a power source 206. Although FIG. 2 illustrates ingestible capsule 104 as having three sensors 202a, 202b, and 202c, one of skill in the art will recognize that any number of sensors may be included in ingestible capsule 104. In one embodiment, there may be no sensor(s) 202 at all, providing a capability to track the pill movement in space, hence allowing a mapping of a gastro-intestinal tract and also the time of movement within that tract.

In an embodiment where ingestible capsule 104 has one or more sensor(s) 202, sensor(s) 202 are used to sense (e.g., measure, detect, etc.) a received stimulus 210, and generate a sensor output signal 212. Sensor output signal 212 may be a digital or analog signal, depending on the particular implementation of sensor 202. In alternative embodiments the acoustically transmissive encapsulation 208 may be made of sensor(s) 202, or sensor 202 may be integrated within the materials known as acoustically transmissive encapsulation 208. Ingestible capsule 104 can include any number of sensors 202, each of which may all sense the same condition or may sense a different condition than another sensor 202. Sensor 202 may detect and/or interact directly with conditions of the body. Sensor 202 may also detect and/or interact with signals emanating from the pill and reflecting off nearby tissues, such as is the case with, for example and without limitation, a camera detecting light that originates from the capsule, ultrasonic detectors, and radioactivity sensors. In an embodiment, sensor 202 detects reflections of signal 106 from nearby gastro-intestinal and other body tissues.

Logic control 214 initiates activity of sensor 202. Sensor 202 detects or interacts with the body via signal 210 and produces a sensor output signal 212. Communications module 204 receives sensor output signal 212, and generates communication signal 106 to include information based on sensor output signal 212. Communication signal 106 is transmitted from ingestible capsule 104.

Figure 3:
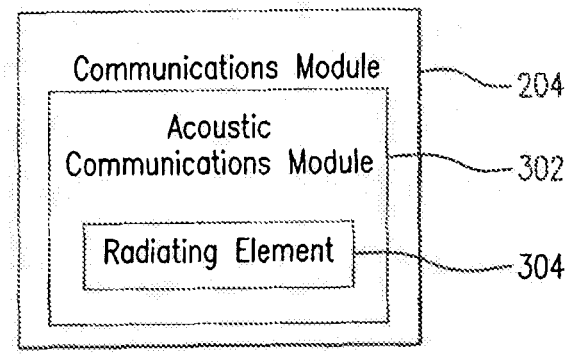
FIG. 3 is a block diagram of a communications module according to an embodiment of the present invention.

In an example embodiment, as shown in FIG. 3, communications module 204 may include an acoustic communications module 302, configured to transmit and/or receive an acoustic communications signal. For example, acoustic communications module 302 may include one or more acoustic transducers. Sensor output signal 212 is modulated on an acoustic signal that is transmitted as communications signal 106 by the acoustic transducer(s). The acoustic communications signal 106 may be transmitted by radiating element 304, which may be, for example, an electromechanical transducer or piezoelectric (e.g., PZT. PVDF, etc.) element or transducer that vibrates at acoustic or ultrasonic frequencies. An example acoustic frequency range in which acoustic communication signal 106 may be transmitted is 20 Hz to 16 KHz, although the frequency may be an acoustic frequency higher or lower than this range in some applications. An example frequency for acoustic communications signal 106 is 40 Hz. In another example embodiment, acoustic communications module 302 may include an ultrasonic communications module, configured to transmit and/or receive a communications signal at ultrasonic frequencies (e.g., between 0.5 to 5 MHz). Generally, transducers are smaller for ultrasonic frequencies, which is useful for a very small sensor device. However, smaller devices also generally transmit less power through a medium and thus need to have a high power input and hence a larger battery. Higher frequency transducers do generally have a higher bandwidth and may have an impact on the amount of sensor data can be transmitted to a receiver. However, attenuation is greater for higher frequencies. A person skilled in the art of acoustic transducers will be able to select an appropriate frequency range for an ideal situation of size and power consumption.

Communications module 204 may be configured to modulate information of sensor output signal 212 according to a variety of modulation techniques, including amplitude modulation (AM), frequency modulation (FM), and phase modulation (PM), and including any combination of these modulation techniques, including in quadrature or other modulation schemes. Acoustic pressures according to embodiments may have various levels, including greater or lower than 1 Pa, including in the KPa (or greater) range to the µPa (or less) range.

Figure 4:
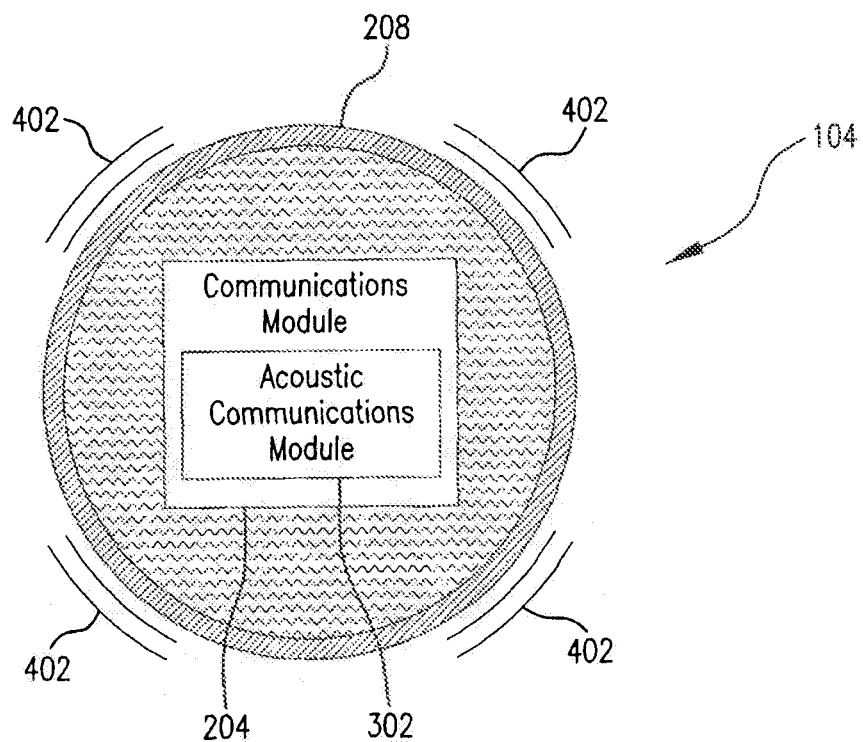
FIG. 4 is a block diagram of an ingestible capsule according to another embodiment of the present invention.

FIG. 4 shows a view of ingestible capsule 104, with communications module 204 including acoustic communications module 302. In FIG. 4, communications module 204 is coupled to acoustically transmissive encapsulation 208. Acoustically transmissive encapsulation 208 vibrates according to acoustic communications module 302 to transmit a communications signal 402, which is an acoustic version of communications signal 106. In FIG. 4, acoustically transmissive encapsulation 208 functions as an acoustic radiating element, vibrating at acoustic frequencies according to acoustic communications module 302.

Returning to FIG. 2, operation of ingestible capsule 104 may be gated and controlled by control logic 214, which itself may be operating in a sub-threshold voltage (Vt) manner (e.g., to save power), or control logic 214 may operate in normal bias modes. In an embodiment, ingestible capsule 104 is an autonomous device with one way communication (transmission capability), so that control logic 214 may be extremely simple, and thus would not consume much power even when operating in normal bias modes. However, in another embodiment, ingestible capsule 104 may communicate in both directions, and may be configured to receive instructions from computing device 108. Control logic 214 may thus have additional complexity in order to, for example, decode and implement received instructions.

Power source 206 provides power (e.g., via electrical energy) to operate the components of ingestible capsule 104 that require power, such as communications module 204 and/or sensor 202. Power source 206 may include, for example and without limitation, a battery, a liquid, or an energy harvesting module.

Figure 16:
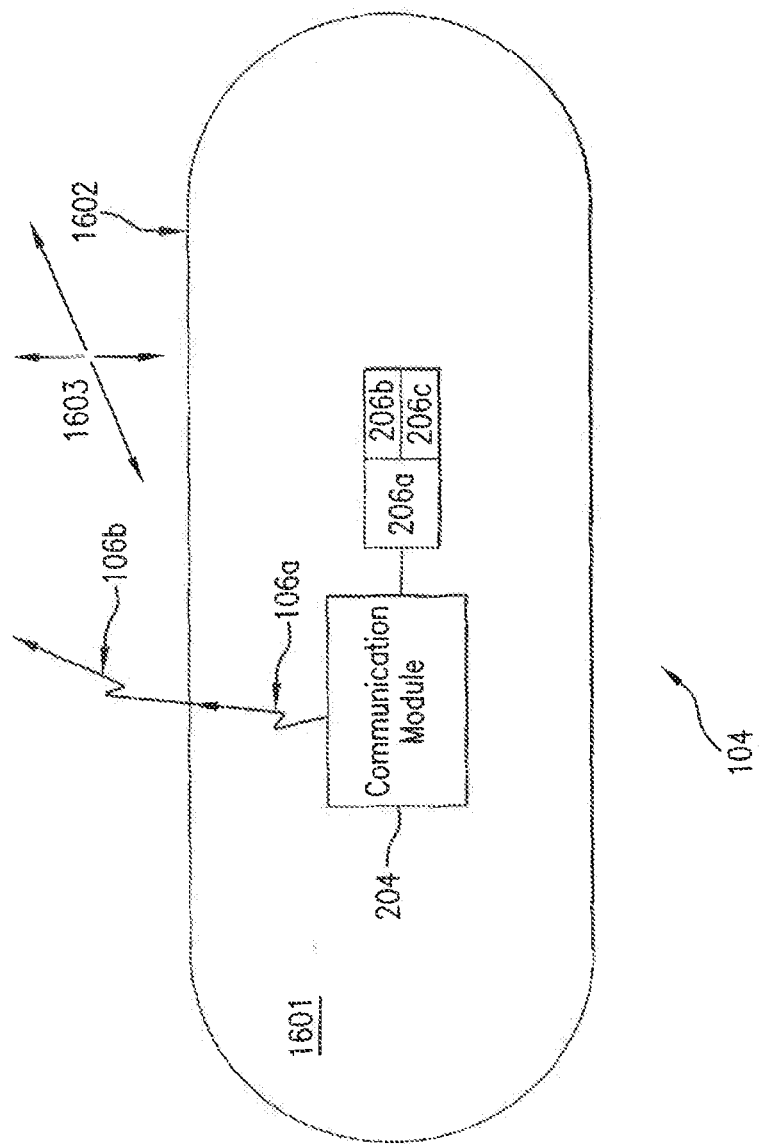
FIG. 16 illustrates a power source for an acoustic transmitter according to an embodiment of the present invention.

In an embodiment, power source 206 includes a liquid or semi-liquid, such as is illustrated in FIG. 16. In this embodiment, communications signal 106 is a signal of acoustic nature, and power source 206 includes an electrolyte 1601 in the form of an acoustically transmissive material such as a liquid or semi-liquid. Electrolyte 1601 serves a first purpose of a battery component but also serves an efficient medium of acoustic transmission. Furthermore, as illustrated in FIG. 16, a material 1602 serves a dual purpose of housing battery 1601 as well as other components, while allowing an efficient transfer of acoustic energy from inside to outside of ingestible capsule 104. FIG. 16 additionally demonstrates control and regulation component 206a, anode 206b, and cathode 206c.

Communication signals 106 pass through electrolyte 1601 and external animal flesh environment 1603. In the case of an acoustic propagation, the most efficient energy transfer is accomplished when the acoustic material impedance from material to material is gradually changed from origin to destination from high to low, or low to high impedance as is common knowledge to those skilled in the art. Communication signal 106 then is demonstrated in FIG. 16 as a combination of signals 106a and 106b to illustrate the change in medium properties from electrolyte 1601 through housing material 1602 and into flesh 1603. As one example of many, electrolyte 1601 may be a citric juice or gel that is nonharmful to human consumption; anode 206b and cathode 206c may include zinc and copper, which is also not harmful to human consumption; and housing 1602 may be comprised of a thin but soft plastic of reasonable acoustic impedance to electrolyte 1601 and animal flesh 1603. However, other material selections by those skilled in the art of battery technology and acoustic propagation for electrolyte 1601, housing 1602, anode 206b and cathode 206c do not depart from the spirit of this invention.

In an embodiment, ingestible capsule 104 is configured for low power operation, including extreme low power (XLP) operation. To achieve XLP operation, ingestible capsule 104 can use one or both of a very small battery and energy harvesting to operate ingestible capsule 104. In an embodiment, circuits of ingestible capsule 104 are implemented in one or more integrated circuits (ICs), in a technology such as CMOS, or other technology. The IC(s) and any other internal components of ingestible capsule 104 may be mounted to a circuit board, or mounted directly to acoustically transmissive encapsulation 208. Thus, in embodiments, power source 206 is configured for low power output, including supplying power in the milliwatt and microwatt ranges. Such low power requirements enable the size of power source 206 to be minimal.

In a CMOS embodiment, MOSFET circuits may be configured to operate in a deep sub-threshold voltage (sub-Vt) mode, which lowers their switching time to acoustic switching frequencies, and lowers their power consumption by orders of magnitude. In such a mode the MOSFET devices operate as analog devices. Such operation was demonstrated in the mid-1980's by Carver Meade with regard to eye and ear chips. Such a mode of operation eliminates the need for digitizing the sensor information, which can be very power intensive, and which further reduces the power consumption by a large factor. Further details on such sub-threshold voltage MOSFET circuits may be found in the following U.S. Patents, which are incorporated herein by reference in their entirety: U.S. Pat. Nos. 6,198,324, 6,252,448, 6,297,668, and 6,333,656.

Acoustically transmissive encapsulation 208 contains sensor 202, communications module 204, and power source 206, and is configured to be ingestible by or inserted within a human and/or animal. Acoustically transmissive encapsulation 208 may be the size of a vitamin or other type of pill that is ingestible by humans. For example, acoustically transmissive encapsulation 208 may be approximately 3 mm in diameter and approximately 5 mm in length. Acoustically transmissive encapsulation 208 may be any suitable shape, including oval, elliptical (as shown in FIG. 2), capsule shaped, or spherical. The small size of acoustically transmissive encapsulation 208 allows ingestible capsule 104 to be easily ingested by an average human 102. The small size overcomes difficulties present with existing camera pills, which are often so large that only a small percentage of the population can actually swallow them. Further, the small size of acoustically transmissive encapsulation 208 increases the ability of ingestible capsule 104 to pass completely through the digestive system of a human 102 without becoming trapped due to size incompatibility.

Acoustically transmissive encapsulation 208 may be made from a variety of non-digestible or slow rate of digestion materials, including: a plastic material, such as a resin, a resinoid, a polymer, a cellulose derivative, a casein material, and/or a protein; a metal, including a combination of metals/alloy; a glass material; a ceramic; a composite material; and/or other material/combination of materials. In a particular embodiment, acoustically transmissive encapsulation 208 may be comprised of a material that aids in the sensing of biological, chemical, or other attributes of body material that touches or comes in close proximity to the acoustically transmissive encapsulation 208, such as could be called an integrated encapsulation and sensor material.

After being swallowed by human 102, ingestible capsule 104 eventually passes from human 102, such as when human 102 has a bowel movement to excrete waste. In an embodiment, ingestible capsule 104 is disposable. In another embodiment, ingestible capsule 104 may be recovered, (and recycled) for reuse.

Depending upon the ability or control of the patient, ingestible capsule 104 may alternatively be inserted into a lower gastrointestinal tract of human 102 as a suppository device.

Depending on the configuration of sensor 202, while passing through human 102, ingestible capsule 104 can sense conditions and/or features of any part of the gastrointestinal tract, and any of the materials/fluids contained within and/or secreted by the organs in the gastrointestinal tract or organs indirectly associated with the gastrointestinal tract. Ingestible capsule 104 can also receive conditions or signals from even more remote body organs such as acoustic pickup of heartbeat and/or breathing and more indirect conditions such as temperature. In an embodiment, a camera is coupled to ingestible capsule 104 to allow visual observation of human 102.

As mentioned, ingestible capsule 104 transmits information in communication signal 106 to be received outside human 102, such as by computing device 108. In an embodiment, computing device 108 may be configured to communicate with a remote entity 502, such as shown in an example sensor communications network 500 shown in FIG. 5. Computing device 108 may be configured to communicate with remote entity 502 using wired and/or wireless links, in a direct fashion or through a network 504. For example, computing device 108 transmits a communication signal 506 to network 504, which transmits a communication signal 508 to remote entity 502. Network 504 may be any type of network or combination of networks, such as a telephone network (e.g., a land line and/or cellular network), a personal area network (PAN), a local area network (LAN), and/or a wide area network (WAN) such as the Internet.

Remote entity 502 may be one or more of a variety of entities, including a human and/or computer-based entity. For example, remote entity 502 may include a doctor who receives information collected by ingestible capsule 104 (and optionally processed by computer device 108) in communication signal 508.

Figure 5:
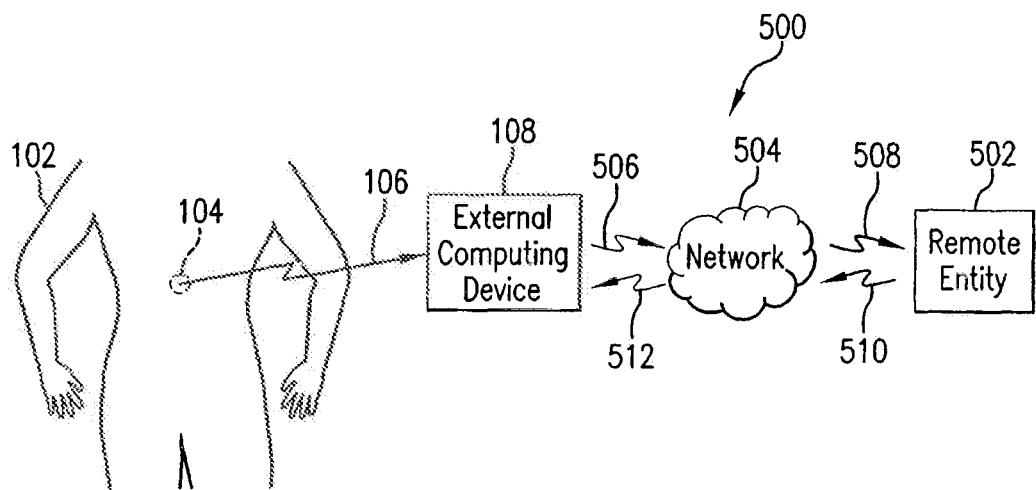
FIG. 5 is a block diagram of a communications network according to an embodiment of the present invention.

As shown in FIG. 5, sensor communications network 500 may include a return communications path from remote entity 502 through network 504 to computing device 108. For example, a return communication signal 510 is transmitted by remote entity 502 to network 504, which transmits a return communication signal 512 to computing device 108. In this manner, remote entity 502 (e.g., doctor and/or computer system) can provide feedback to computing device 108 in communication signal 512 regarding the analysis of human 102 performed by ingestible capsule 104. Return communication signal 512 may include any type of data/information format for providing the feedback, including an email, a text message, a text file, a document formatted for commercially available word processing software, a proprietary document/data format, auditory alarms, alerts and messages, etc.

Figure 6:
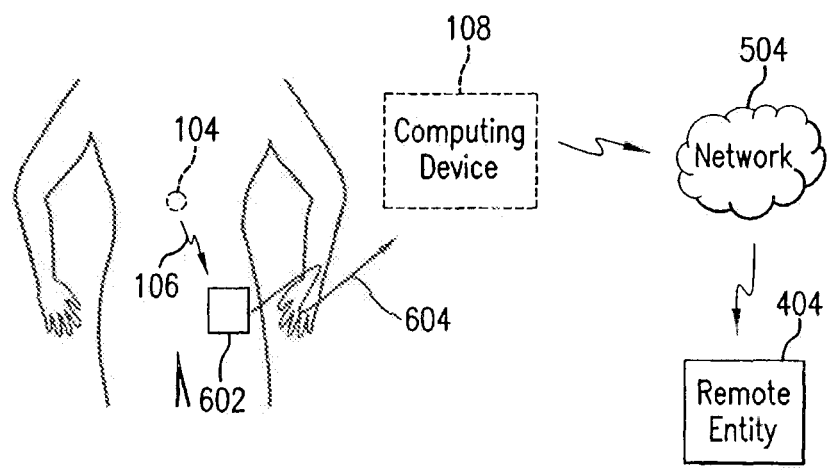
FIG. 6 is a block diagram of an exemplary communications network utilizing a sensor link module according to an embodiment of the present invention.

Ingestible capsule 104 may also communicate with computing device 108 via an intermediate sensor link module 602, as shown in FIG. 6. Sensor link module 602 receives communication signal 106 from ingestible capsule 104. Sensor link module 602 transmits a communication signal 604 to computing device 108, to provide the information sensed by sensor 202 to computing device 108. For example, sensor link module 602 may be used when ingestible capsule 104 communicates using an acoustic communications signal having a power level too low to reliably be received by computing device 108. As shown in FIG. 6, sensor link module 602 is coupled to human 102.

In another embodiment, sensor link module 602 may provide a communication interface between ingestible capsule 104 and network 504, such that a separate computing device 108 is not required. In such an embodiment, sensor link module 602 may perform some or all functions of computing device 108 described above, and thus sensor link module 602 may be referred to as a computing device.

Multiple sensor link modules 602 may provide a capability of location detection through triangulation and other algorithms, capable of detecting sensor device 104 to a very accurate, three (3) dimensional location within human 102. In an embodiment, multiple sensor link modules 602 may be attached to human 102 at various locations in order to receive the interior acoustic signal from different positions. Sensor link module 602 may be, for example, directly attached to the skin of human 102, such as by an adhesive or a strap. Sensor link module 602 may be attached to human 102 in one or more locations, including the head, neck, chest, back, abdomen, arm, leg, etc. With regard to receiving communication signal 106 from ingestible capsule 104 passing through the gastrointestinal tract, ingestible capsule 104 may be attached to the neck, chest, back, and/or abdomen for a short signal path.

An amount of received information is in part proportional to the number of sensor link modules 602 attached to human 102. The array of sensor link modules 602 may be attached at specific locations on human 102 to increase, and even maximize, the received diagnostic information. Multiple sensor link modules 602 can identify a specific location of the ingestible capsule 104 which can be used for linking a location to the detection of a sensed material. The location can also be used to identify a historical analysis of the track taken by the ingestible capsule and the speed of passage.

For example, the attachment of an array of three or more sensor link modules 602 to human 102 may enable triangulation or other location finding algorithms to be used to locate ingestible capsule 104 in human 102. Alternatively, one or more sensor link modules 602 having three or more receivers each may be used to the same effect. Further details regarding location of an ingestible capsule may be found in co-pending U.S. Patent Appl. Publication No. 2008/0058597 A1, titled "Imaging and Locating Systems and Methods for a Swallowable Sensor Device," incorporated by reference herein in its entirety. By locating ingestible capsule 104 in human 102, a location of a sensed material in human 102 can be determined.

Figure 7:
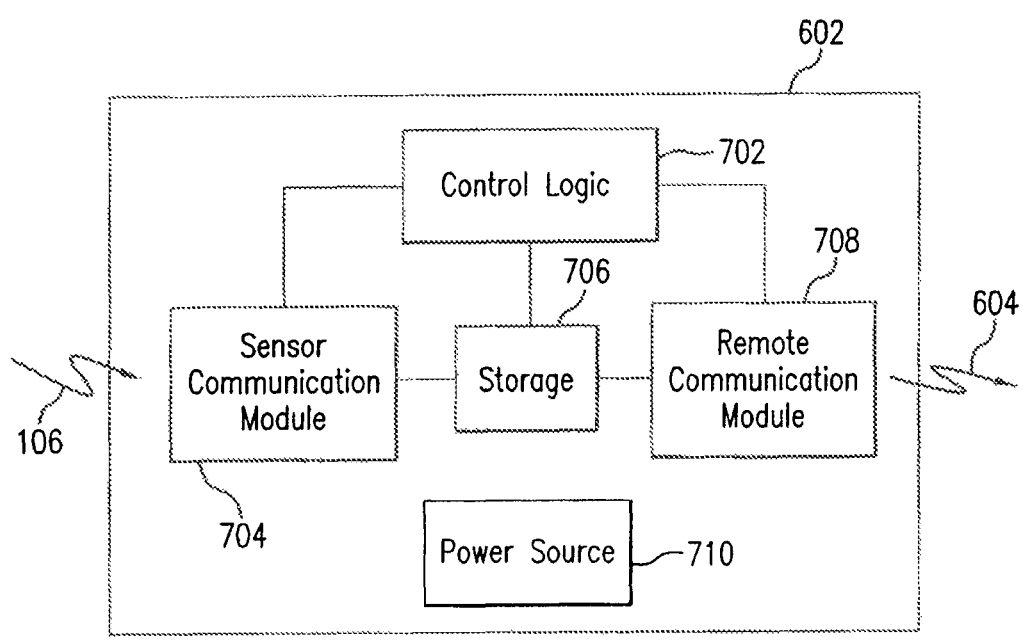
FIG. 7 is a block diagram of a sensor link module according to an embodiment of the present invention.

In embodiments, sensor link module 602 may be configured in various ways. For instance, FIG. 7 shows an example sensor link module 602, according to an embodiment of the present invention. As shown in FIG. 7, sensor link module 602 includes a control logic 702, a sensor communication module 704, a storage 706, a remote communication module 708, and a power source 710.

Sensor communication module 704 receives communication signal 106 from ingestible capsule 104. Sensor communication module 704 demodulates the sensor-related information of communication signal 106. Furthermore, sensor communication module 704 may process and/or convert a format of the information received in communication signal 106. For example, sensor communication module 704 may perform an analog-to-digital (A/D) conversion of the received sensor information, and outputs a sensor information signal. The sensor information signal may be received by storage 706 and/or by control logic 702. In an embodiment, sensor link module 602 may convert a communications signal 106 (for example, an acoustic protocol) into an industry adopted or standardized communications signal 604 (for example, Medical Implant Communications Services (MICS), an RF medical devices standardized protocol). Such an embodiment may not require much storage 706, potentially as small as a single register device.

In other embodiments, storage 706 is configured to store the sensor information of the sensor information signal. Storage 706 may include any type of suitable storage, including a hard drive and/or memory devices. For example, in an embodiment, storage 706 includes a read/write non-volatile memory, such as a secure digital (SD) memory card as is typically used in a PDAs and digital cameras. Storage 706 can output the stored information in a stored sensor information signal, for subsequent transmission to computing device 108 by remote communication module 708. In an embodiment with a removable storage 706 (SD memory, for example), physical removal of the memory and insertion into computing device 108 or remote entity 404 may be both possible and cost effective.

Control logic 702 is configured to control operation of sensor link module 602.

Remote communication module 708 receives the stored sensor information signal, and formats the sensor-related information for transmission. Furthermore, remote communication module 708 transmits the sensor information in communication signal 604. Remote communication module 708 may be configured to transmit communication signal 604 in a variety of formats/protocols, such as a standard RF communication protocol including Bluetooth, IEEE 802.11, Zigbee, or other communication protocol, standard or otherwise. For example, in embodiments, computing device 108 may be a Bluetooth, 802.11, and/or Zigbee configured handheld device such as cell phone, personal digital assistant (PDA), a Blackberry™, wrist watch, music player, or laptop, or other type of computer, handheld, desktop, or otherwise. Remote communication module 708 may also transmit an identification number assigned to ingestible capsule 104 for identification by a receiver.

Power source 710 provides power to elements of sensor link module 602 that require power, such as control logic 702, sensor communication module 704, storage 706, and remote communication module 708. For example, power source 710 may include one or more batteries that are rechargeable or non-rechargeable. Power source 710 may also (or alternatively) include an interface for externally supplied power, such as standard AC power.

As described above, in an embodiment, ingestible capsule 104 can transmit an acoustic signal. By receiving the acoustic signal transmitted by ingestible capsule 104, sensor link module 602 may perform a type of ultrasound analysis based on the human interior generated acoustic signal from ingestible capsule 104. As acoustic communication signal 106 is transmitted through human 102 from ingestible capsule 104, signal 106 is transformed by attenuation, refraction, and reflection, as a function of the tissue of human 102 that signal 106 passes through. The transformed signal thus provides additional diagnostic information to sensor link module 602, very much like a diagnostic ultrasound conveys diagnostic information that can be analyzed by a trained technician. The acoustic signal from ingestible capsule 104 may be viewed as an "interior" ultrasound or "sonogram", which can be analyzed to extract additional diagnostic information regarding human 102. In an embodiment, information received by sensor link module 602 regarding the interior ultrasound signal can be used to generate a graphical display of at least a portion of the interior of human 102.

III. Example Computer System Embodiments

According to an example embodiment, an ingestible capsule may execute computer-readable instructions to perform its functions. Furthermore, a sensor link module for communicating with the ingestible capsule may execute computer-readable instructions to communicate with the ingestible capsule. Still further, a computing device may execute computer-readable instructions to communicate with the ingestible capsule and/or the sensor link module, and/or to process information obtained by the ingestible capsule and/or sensor link module, as described above. Still further, a test kit and medical diagnostic network system may each execute computer-readable instructions to perform its functions.

Figure 8:
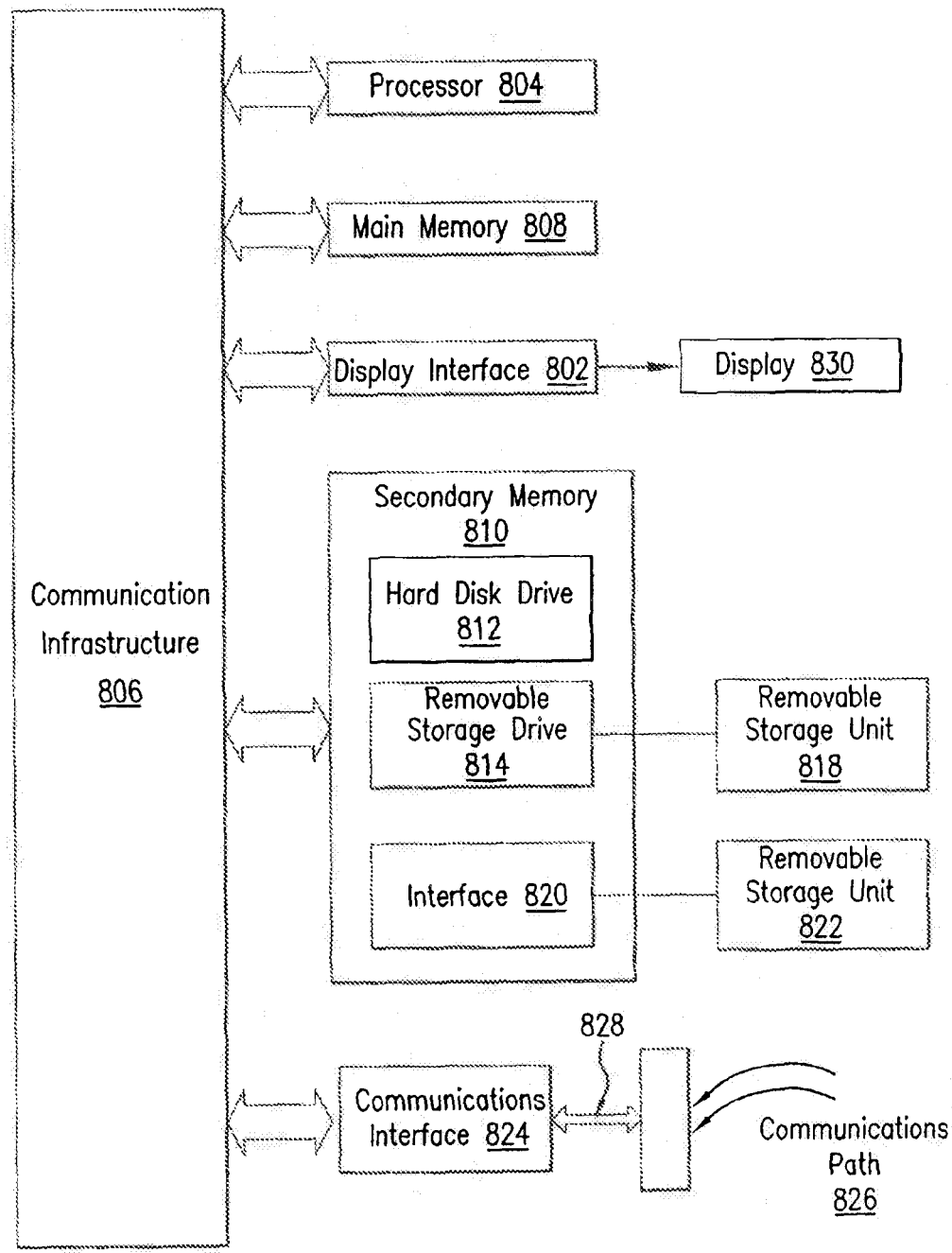
FIG. 8 is an exemplary computer system useful for implementing the present invention.

In one embodiment, one or more computer systems are capable of carrying out the functionality described herein. An example of a computer system 800 is shown in FIG. 8.

The computer system 800 includes one or more processors, such as processor 804. The processor 804 is connected to a communication infrastructure 806 (e.g., a communications bus, cross-over bar, or network). Various software embodiments are described in terms of this exemplary computer system. After reading this description, it will become apparent to a person skilled in the relevant art(s) how to implement the invention using other computer systems and/or architectures.

Computer system 800 can include a display interface 802 that forwards graphics, text, and other information from the communication infrastructure 806 (or from a frame buffer not shown) for display on the display unit 830.

Computer system 800 also includes a main memory 808, preferably random access memory (RAM), and may also include a secondary memory 810. The secondary memory 810 may include, for example, a hard disk drive 812 and/or a removable storage drive 814, representing a floppy disk drive, a magnetic tape drive, an optical disk drive, etc. The removable storage drive 814 reads from and/or writes to a removable storage unit 818 in a well known manner. Removable storage unit 818 represents a floppy disk, magnetic tape, optical disk, etc. which is read by and written to by removable storage drive 814. As will be appreciated, the removable storage unit 818 includes a computer usable storage medium having stored therein computer software and/or data.

In alternative embodiments, secondary memory 810 may include other similar devices for allowing computer programs or other instructions to be loaded into computer system 800. Such devices may include, for example, a removable storage unit 822 and an interface 820. Examples of such may include a program cartridge and cartridge interface (such as that found in video game devices), a removable memory chip (such as an erasable programmable read only memory (EPROM), or programmable read only memory (PROM)) and associated socket, and other removable storage units 822 and interfaces 820, which allow software and data to be transferred from the removable storage unit 822 to computer system 800.

Computer system 800 may also include a communications interface 824. Communications interface 824 allows software and data to be transferred between computer system 800 and external devices. Examples of communications interface 824 may include a modem, a network interface (such as an Ethernet card), a communications port, a Personal Computer Memory Card International Association (PCMCIA) slot and card, etc. Software and data transferred via communications interface 824 are in the form of signals 828 which may be electronic, electromagnetic, optical or other signals capable of being received by communications interface 824. These signals 828 are provided to communications interface 824 via a communications path (e.g., channel) 826. This channel 826 carries signals 828 and may be implemented using wire or cable, fiber optics, a telephone line, a cellular link, a radio frequency (RF) link and other communications channels.

In this document, the terms "computer program medium" and "computer usable medium" are used to generally refer to media such as removable storage drive 814 and a hard disk installed in hard disk drive 812. These computer program products provide software to computer system 800. The invention is directed to such computer program products.

Computer programs (also referred to as computer control logic) are stored in main memory 808 and/or secondary memory 810. Computer programs may also be received via communications interface 824. Such computer programs, when executed, enable the computer system 800 to perform the features of the present invention, as discussed herein. In particular, the computer programs, when executed, enable the processor 804 to perform the features of the present invention. Accordingly, such computer programs represent controllers of the computer system 800.

In an embodiment where the invention is implemented using software, the software may be stored in a computer program product and loaded into computer system 800 using removable storage drive 814, hard drive 812 or communications interface 824. The control logic (software), when executed by the processor 804, causes the processor 804 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

IV. Acoustic Information Exchange

Because signals are transmitted between ingestible capsule 104 and an external receiver and/or transmitter, the signals necessarily pass through living tissue of human 102. To minimize damage to the tissue, ingestible capsule 104 is configured for low power operation, including extreme low power (XLP) operation. Operating at a lower power than existing camera pills or radio frequency (RF) based pills enables ingestible capsule 104 to have a smaller, longer-lasting battery than existing pills. Low power operation also provides the flexibility to allocate power to functions of ingestible capsule 104 other than information exchange without sacrificing size. For example, reducing the power for information exchange enables additional power to be used to drive multiple sensors.

Ingestible capsule 104 can achieve low power communications by using acoustic signals for information exchange. The acoustic channel can deliver reliable information (e.g., a signal having a signal-to-noise ratio of approximately 15 dB) with a total required transmission power as low as a few microwatts, depending on the amount of information that is transmitted. Such low power is a possibility because ingestible capsule 104 need not transmit the signal any farther than approximately 20 cm (e.g., from the innermost point in human 102 to a detector on the skin of human 102).

As discussed with respect to FIG. 3, ingestible capsule 104 may include an acoustic communications module, such as acoustic communications module 302, configured to transmit and/or receive an acoustic communications signal. For the acoustic transmitter to effectively transmit a signal for detection outside the body, the signal must have a relatively high signal-to-noise ratio (SNR), such as, for example, 15 dB. Methods and systems for increasing the SNR will be described further below. Additionally, since the pill may rotate or otherwise change orientation while inside human 102, the acoustic signal should be transmitted substantially omnidirectionally.

In an embodiment, omnidirectionality can be obtained by creation of a spherical transducer that launches a spherical wave front. In another embodiment, omnidirectionality may be implemented with multiple transducers having a more directional radiation pattern utilized in sequential time periods transmitting the same information on multiple transducers. Orientation of these transducers is most efficient when the orientations of the peak signal are orthogonally placed within a final configuration. The number of transducers, the amount of information sent in a time period, and the algorithm employed to switch to another time period and transducer may be determined by a person having skill in the art without departing from the spirit and scope of the present invention.

As previously described, FIG. 4 shows a spherical embodiment of ingestible capsule 104, wherein signal 106 is transmitted omnidirectionally via a single acoustic transducer. When signal 106 is transmitted from the single acoustic transducer, signal 106 interacts with various surfaces, for example, the internal tissue and skin of human 102. Interaction with these surfaces results in one or both of reinforcement reflections and cancelling reflections that may interfere with signal 106. As a result, some of the information carried in signal 106 may be corrupted by the time it reaches an external receiver. Further, if the receiver is located at a null in the signal, no information will be received at all. In an embodiment, multiple external receivers may be utilized. Reflections (constructive or destructive) may interfere with signal 106, resulting in different signals being received by each of the multiple external receivers. Such an embodiment allows signal 106 to be received from one external receiver even when signal 106 is too distorted to be correctly detected on an external receiver.

Figure 9:
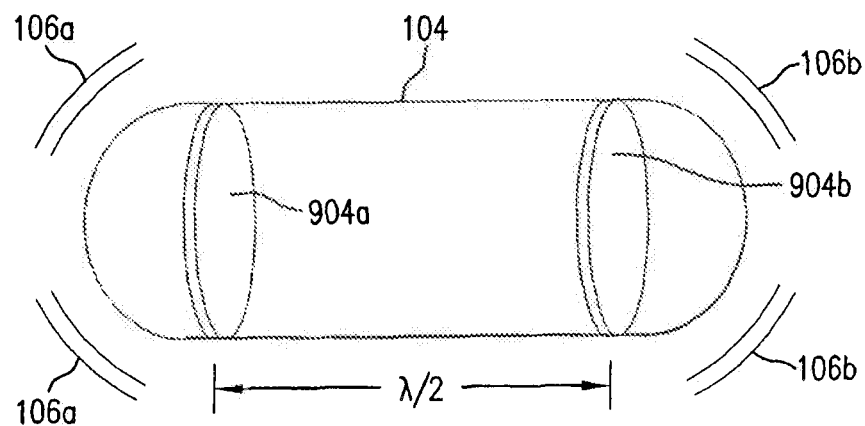
FIG. 9 is a block diagram of an ingestible capsule according to yet another embodiment of the present invention.

FIG. 9 illustrates an alternative embodiment of an ingestible capsule 104 that reduces problems with interfering signals. Ingestible capsule 104 is capsule-shaped, and includes two acoustic transducers, 904a and 904b. In an embodiment, acoustic transducers 904a and 904b are each placed at an equal distance from their respective ends. Transducer 904a transmits an output signal 106a. Transducer 904b transmits an output signal 106b. Due to the placement of transducers 904a and 904b near the ends of ingestible capsule 902, the combined effect of output signals 106a and 106b is an output signal having a uniformity similar to that of an omnidirectional transmitter. Furthermore, if transducers 904a and 904b are appropriately spaced, nulls in the output signal can be eliminated. For example, if the spacing between transducers 904a and 904b is approximately one-half the wavelength of the transmitted signal, a signal produced by one transducer will be received even when the signal produced by the other transducer is at a null.

In another embodiment, transducers 904a and 904b need not be located with specific spacing or orientation referenced to a frequency of operation as depicted in FIG. 9. In this embodiment, information can be transmitted during a first time period on transducer 904a, providing signal 106a to be received by one or multiple external receivers. Subsequently, a duplicate set of information may be transmitted during a second time period on transducer 904b, providing signal 106b to be received by one or multiple external receivers. By having different origins of signals 106, but the same content, an external receiver is likely to properly receive a signal 106b in the event that signal 106a has been severely impacted by destructive interference caused by reflections of the signals off a variety of body parts and cavities. While FIG. 9 depicts use of two transducers, the use of three or more transducers gains more probability that signals are received and do not depart from the scope and spirit of this invention.

Figure 10:
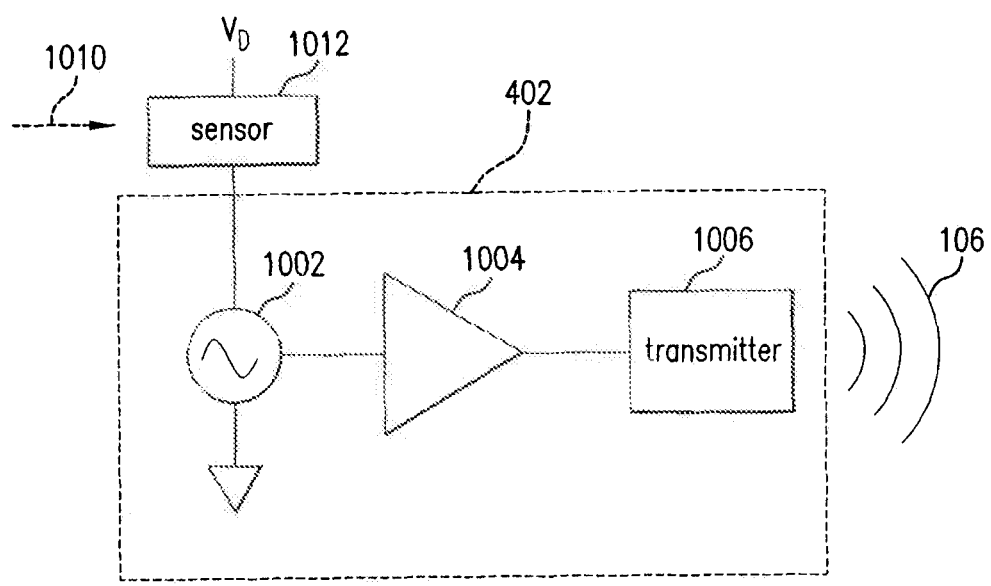
FIG. 10 is a circuit diagram of an acoustic communications module according to an embodiment of the present invention.

FIG. 10 shows an example circuit 1000 for acoustic communications module 402, according to an embodiment of the present invention. As shown in FIG. 10, circuit 1000 includes an oscillator 1002, an amplifier 1004, and an acoustic transducer 1006. In the example of FIG. 10, sensor 1012 has a resistance (or other impedance value) that changes based on the sensed stimulus, stimulus 1010. For example, sensor 1012 may be a temperature sensor. Sensor 1012 is coupled in series with oscillator 1002, which may be a current-dependent oscillator configured to operate in a deep-threshold voltage (Vt) range to lower an oscillation frequency generated by oscillator 1002 to a desired acoustic frequency range. As the resistance of sensor 1012 changes, the oscillator frequency changes in a predictable way. An output of oscillator 1002 is coupled to an input of an amplifier circuit 1004 for amplification. An output of amplifier 1004 is input to acoustic transducer 1006 (which may include or be coupled to an acoustic radiating element or acoustic actuator) that acts as a "speaker" to send the acoustic information out in an acoustic communication signal 106. Acoustic transducer 1006 may be, for example, one or more piezoelectric transducers. Although acoustic transducer 1006 is described as being used for transmitting a signal, one of skill in the art will recognize that acoustic transducer 1006 may also be used to receive an incoming acoustic signal. Additionally, although circuit 1000 is discussed herein as transmitting sensor information, one of skill in the art will recognize that circuit 1000 may also be modified to receive information from transducer 1006. Further, although circuit 1000 is discussed herein as transmitting sensor information, one of skill in the art will recognize that circuit 1000 may also be used to transmit acoustic signals used for imaging and/or locationing without departing from the spirit and scope of the present invention.

In another embodiment, no oscillator is needed to drive oscillation of acoustic transmitter 1006. Instead, an electromechanical modulation method using only a DC voltage instead of an internal oscillator may be used to modulate information into output signal 106. The electromechanical modulation method takes advantage of the nature of piezoelectric elements to expand or contract in response to an applied voltage. If voltage is applied in an appropriate manner, the resulting expansion or contraction of the piezoelectric element can be indicative of "1" and "0" bits in an information stream.

Figure 11:
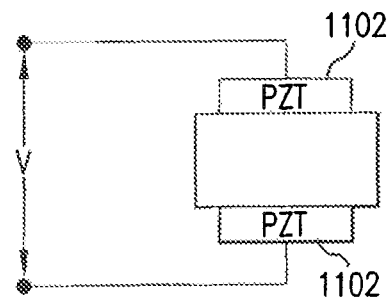
FIG. 11 is a cross-section of a piezoelectric transducer according to an embodiment of the present invention.

FIG. 11 is a block diagram illustrating a cross-section of an exemplary piezoelectric transducer 1102 for modulating information into output signal 106 using electromechanical modulation. In FIG. 11, a voltage V is coupled across piezoelectric transducer 1102. When voltage V is equal to 0 V, piezoelectric transducer 1102 is uncompressed and has a given acoustic impedance. When voltage V is greater than 0, piezoelectric transducer 1102 is compressed (e.g., clamped), which increases the spring force. This compression makes piezoelectric transducer 1102 stiffer, changing the acoustic impedance of piezoelectric transducer 1102. Piezoelectric transducer 1102 thus has a first resonant frequency at 0 V and a second resonant frequency at the higher voltage.

Figure 12:
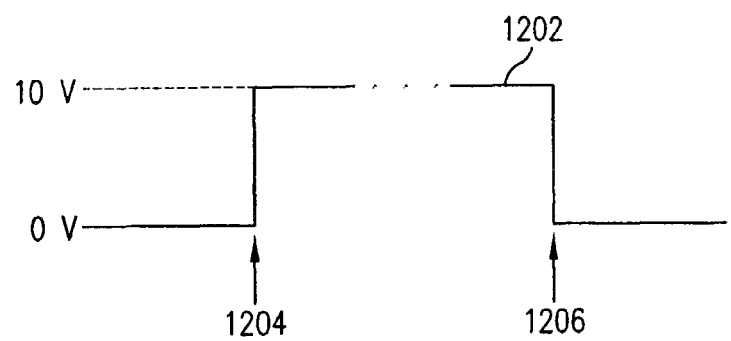
FIG. 12 is an exemplary step function.

A step function may be applied to piezoelectric transducer 1102 to take advantage of the resonant frequency variation. FIG. 12 illustrates an exemplary step function 1202. At point 1204, the voltage across piezoelectric transducer 1102 is suddenly increased from, for example, 0 V to 10 V. Although this example will be described with using a low voltage of 0 V and a high voltage of 10 V, one of skill in the art will recognize that any two voltages having a differential may be used without departing from the spirit and scope of the present invention. As a result, piezoelectric transducer begins ringing at a frequency $F_{10V}$. At point 1206, the voltage across piezoelectric transducer 1102 is suddenly decreased from, for example and without limitation, 10 V to 0 V. As a result, piezoelectric transducer changes impedance and begins ringing at a frequency $F_{0V}$ that is different from frequency $F_{10V}$.

The sudden changes in applied voltage in step function 1202 are similar to a tuning fork being struck. As a result, piezoelectric transducer 1102 rings at a self-resonance value with no additional energy applied. This makes electromechanical modulation useful for low power situations. Information bit values can be assigned to the frequencies at which piezoelectric transducer 1102 rings. For example, the frequency at which piezoelectric transducer 1102 rings when subject to a voltage at 10 V may indicate a "1" bit, while the frequency at which piezoelectric transducer 1102 rings when the voltage is dropped to 0 V may indicate a "0" bit.

Figure 13:
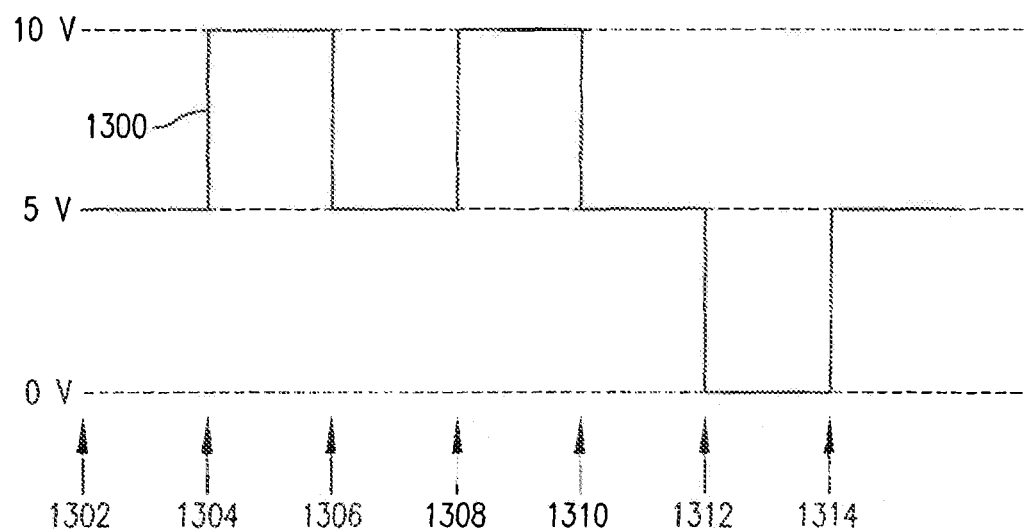
FIG. 13 is another exemplary step function.

An intermediate voltage may be utilized in electromechanical modulation to provide a drone frequency that separates out sequential bits in an information stream. FIG. 13 illustrates an exemplary waveform 1300 for providing a high frequency, a low frequency, and a drone frequency to produce an information stream. In this example, an intermediate voltage of 5 V is used between bits to provide bit separation. Waveform 1300 begins at point 1302 with the application of a 5 V signal, causing piezoelectric transducer 1102 to ring at a drone frequency, $f_D$. At point 1304, a 10 V signal is applied to piezoelectric transducer 1102. As a result, piezoelectric transducer 1102 resonates at a frequency $f_{10V}$, which may represent, for example, a "1" bit. At point 1306, after the resonance of piezoelectric transducer 1102 has faded due to damping in piezoelectric transducer 1102, voltage V is returned to 5 V. The drop from 10 V to 5 V causes piezoelectric transducer 1102 to ring at drone frequency $f_D$. At point 1308, a 10 V signal is applied, causing piezoelectric transducer 1102 to ring at frequency $f_{10V}$ again, producing another "1" bit. At point 1310, after the resonance of piezoelectric transducer 1102 has faded, voltage V is returned to 5 V, causing piezoelectric transducer 1102 to ring at drone frequency $f_D$. At point 1312, voltage V is dropped to 0 V. The drop causes piezoelectric transducer 1102 to resonate at a frequency $f_{0V}$, which may represent, for example, a "0" bit. At point 1314, after the resonance of piezoelectric transducer 1102 has faded, voltage V is returned to 5 V, causing piezoelectric transducer 1102 to ring at drone frequency $f_D$. In this manner, waveform 1300 provides a "1-1-0" signal.

The amount of time it takes the resonance of piezoelectric transducer 1102 to dampen out after each voltage is applied depends on the Q of the resonator. The receiver can be set accordingly to receive the low power information communication modulated using electromechanical modulation. Since piezoelectric transducer 1102 uses only a DC voltage in this embodiment and does not use an oscillator to drive piezoelectric transducer 1102, leakage in the circuit is similar to loss in a capacitor and the power level required is approximately $\frac{1}{1000}$ the power required to use electromagnetic signals (such as RF).

When a signal is transmitted from ingestible capsule 104, the vibration of, for example, piezoelectric transducer 1102 in communications module 204 may interfere with the operation of sensor 202. Control logic 604 can be configured to enable or disable operation of sensor 202 and/or communications module 204 at various times during the transit of ingestible capsule 104 through, for example, the gastrointestinal tract. Control logic 604 may enable or disable operation of elements of ingestible capsule 104 based on time and/or location of ingestible capsule 104. For example, control logic 214 may include a timing module. The timing module of control logic 214 may be used to enable and disable sensor 202 and/or communication module 204 in a periodic manner or at predetermined time intervals, so that sensor information is transmitted at set times.

In an embodiment, a sensor 202a may interfere with signals 106, and should therefore be sampled only when signals 106 are not present in sufficient energies, such as would be adjacent to communications module 204. For example, there may exist a standard standoff period after each information exchange that allows new, non-corrupted information to be taken by sensor 202. During this standoff period, sensor 202 may be activated and sensor readings read and stored. After the standoff period ends, the acoustic communications module may be re-activated for transmission. After transmission, a new standoff period begins. In another embodiment, however, sensor 202 may only be valid when in the presence of signal 106, such as with an acoustic receiver sensor to match in frequency with signal 106. In this embodiment, it is also likely that sensor 202 requires a signal of comparison electrically connected to communications module 204. Such a device results in sensing the reflectivity of tissue surrounding device 104, for example, a self-contained localized ultrasonic imaging device. Additionally, such a device is efficient in that a reference signal for imagery is derived from a communications signal 106, not a separate signal requiring more power, and hence a larger device 104.

Control logic 214 may be configured to gate power from power source 206 to sensor 202 and/or communications module 204, or to gate them in other manners to enable or inhibit their operation as desired. Alternatively, control logic 214 may receive information from sensor(s) 202 to determine a relative location of ingestible capsule 104 in gastrointestinal tract 300. Based on the determined location, control logic 214 may enable or disable operation of communications module 204 and/or sensor 202. Furthermore, control logic 214 may also place communications module 204 and/or sensor 202 in a power conservation mode, for example a reduced power signal 106, when in close proximity to an external receiver and/or reduced sensor activity. Alternatively, control logic 214 may instigate a cycle based on sensor activity and/or location.

V. Phased Array Sensor Link Module

As described above with respect to FIG. 6, ingestible capsule 104 may communicate with a sensor link module acting as an intermediary to or in lieu of computing device 108. Sensor link module 602 may be coupled to human 102 in a variety of ways. For example, sensor link module 602 may be directly attached to the skin of human 102, such as by an adhesive or a strap. Sensor link module 602 may be incorporated in a patch for direct attachment to a surface, such as skin, of human 102. An adhesive layer may be coupled to sensor link module 602. The adhesive layer may include, for example, an adhesive commonly used in transdermal patches.

In one embodiment, each sensor link module 602 includes a single acoustic transducer, and multiple patches can be used to triangulate the location of an ingestible capsule, receive information exchanges from the ingestible capsule, and/or transmit information to the ingestible capsule. In another embodiment, a single sensor link module 602 includes multiple acoustic transducers. The transducers are organized into an array, receive information exchanges from the ingestible capsule, and/or transmit information to the ingestible capsule. Additionally, transducers organized into an array can facilitate an accurate location, whereby phase differences between the transducers are used to calculate the direction (angle) of the ingestible capsule; in combination, amplitudes of signals between the transducers at the same or different frequencies derive distance. The combination creates an accurate location of device 104.

Figure 14:
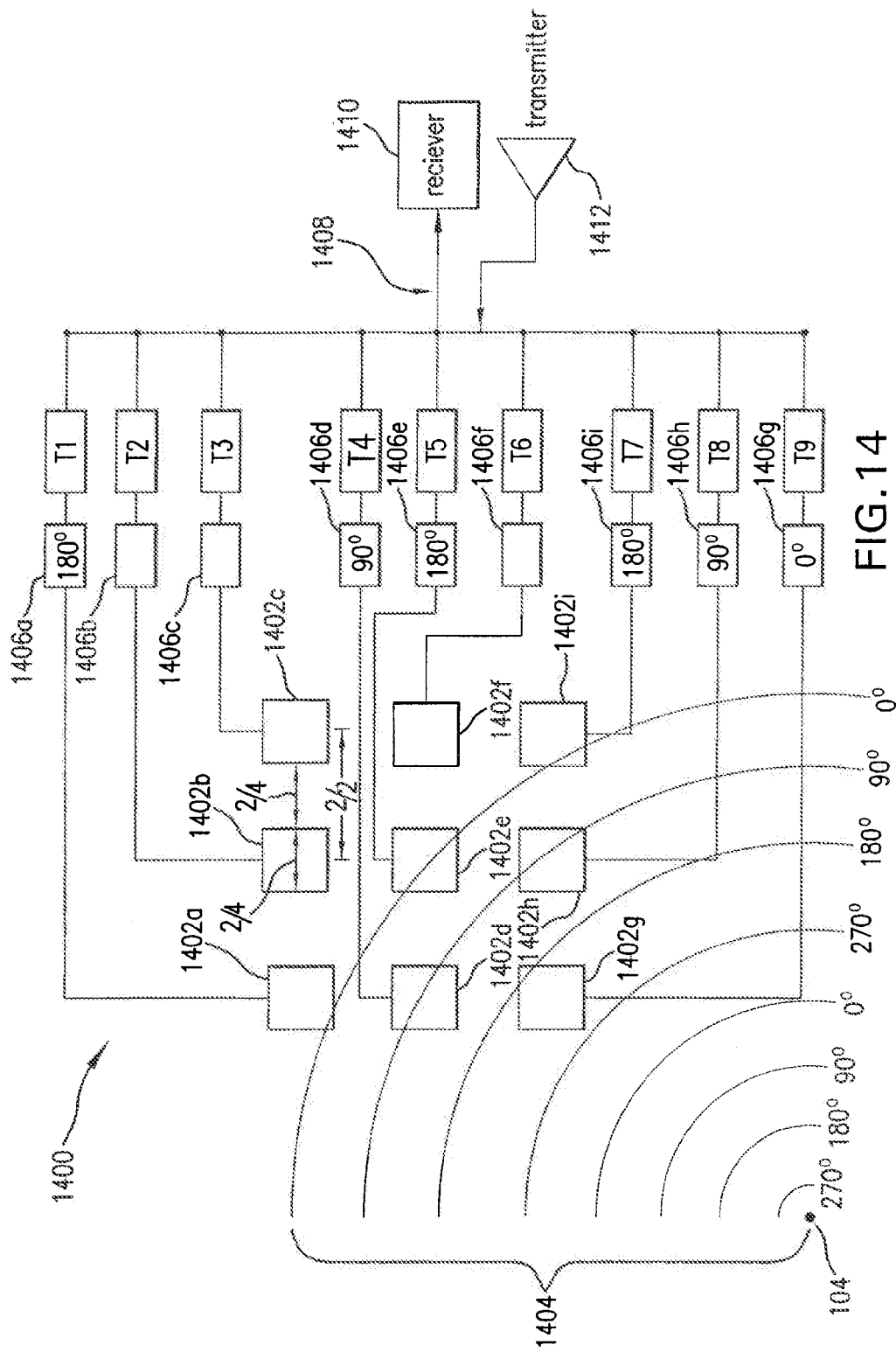
FIG. 14 is a block diagram of a phased array according to an embodiment of the present invention.

FIG. 14 is an illustration of an exemplary phased array 1400 for use as a sensor link module according to an embodiment of the present invention. Phased array 1400 includes multiple acoustic transducers 1402. Although FIG. 14 illustrates an array of nine acoustic transducers 1402a-1402i, one of skill in the art will recognize that any number of acoustic transducers 1402 may be used without departing from the spirit and scope of the present invention. Further, one of skill in the art will recognize that acoustic transducers 1402 may be placed in any pattern, such as a grid pattern or a close-packed hexagonal array pattern.

An array of acoustic transducers 1402 allows triangulation to be performed using a single sensor link module when a device, such as ingestible capsule 104, emits a signal 1404. Signal 1404 may be an information signal, such as information signal 106, or it may be a locationing signal emitted, for example, prior to the emission of information signal 106. As illustrated in FIG. 14, signal 1404 has various wavefronts.

The phase of the signal detected by a given acoustic transducer 1402 will vary, depending on the location of ingestible capsule 104 relative to the given acoustic transducer 1402. The operating wavelength $\lambda$ of ingestible capsule 104 determines the size and location of each acoustic transducer 1402. If each acoustic transducer has a width of $\lambda/4$ and is separated from other acoustic transducers by a distance of $\lambda/4$, such that the distance between the centers of two adjacent acoustic transducers is $\lambda/2$, different phases of each signal period can be detected by the various acoustic transducers 1402. The different phases and amplitudes of signal 1404 as detected by multiple acoustic transducers 1402 can then be used to pinpoint the location of ingestible capsule 106 relative to the sensor link module by calculation of angle and distance from the phase and amplitude, respectively, of signal 106 as it is received by transducers 1402.

Because the signal is acoustic, however, it can be difficult to ensure that the signal detected by transducer 1402 is at its peak at a combined reception point 1408 for input to receiver 1410, which is needed for accurate locationing. To solve this difficulty, an adjustable delay 1406 may be coupled to each acoustic transducer 1402. In an embodiment, each adjustable delay 1406 automatically adjusts itself to achieve maximum gain at a peak signal amplitude with respect to a combined signal at point 1408, or alternatively with respect to a single reference signal such as element 1402a, similarly to a radio frequency phased array construction. In another embodiment, a separate circuit may adjust delays 1402a-1402i. Detection of the peak signal amplitude at a maximum gain (thus maximizing SNR) may occur based on, for example, successive approximation or a previous location measurement. Use of a successive approximation method is possible because received acoustic signal 1404 is moving much more slowly than the time it takes to digitally process received signal 1404. For example, using a 1 MHz digital signal processor, all the calculations needed to focus on the signal can be performed more quickly than the signal changes.

For example, in FIG. 14, a first portion of a wavefront (e.g., a portion of signal 1404 assigned a 0° phase delay) of signal 1404 is detected by acoustic transducers 1402a, 1402e, and 1402i. A second portion of wavefront of signal 1404 detected by acoustic transducers 1402d and 1402h differs from the first portion of wavefront of signal 1404 by 90°. A third portion of wavefront of signal 1404 detected by acoustic transducer 1402g differs from the first portion of wavefront of signal 1404 by 180°. Therefore, the maximum gain of the signal is produced when a value of 0° is assigned to phase delay 1406g, a value of 90° is assigned to each of phase delays 1406d and 1406h, and a value of 180° is assigned to each of phase delays 1406a, 1406e, and 1406i. To achieve the maximum gain of the system, all wavefront peaks should be aligned at the output of adjustable delays 1406a-1406i.

Once the phase footprint of signal 1404 is determined, the phase footprint can be used to identify the location of ingestible capsule 104. That is, the phase separation of the different acoustic transducers 1402 identify the angular direction of ingestible capsule 104 while the differences in time of arrival between acoustic transducers 1402 indicate a distance to ingestible capsule 104.

The same phase information can also be used to maximize the SNR of an information signal received from ingestible capsule 104, such as output information signal 106. In an embodiment, a primary wavefront from device 104 is phase aligned throughout all transducers 1402a-1402i. However, acoustic noise is typically produced by reflections from objects within the human 102 and also the exterior skin of human 102. Reflections likely do not originate from the same angle with respect to the array 1402. Thus, the combined noise signal output at point 1408 is reduced from maximum signal as the reflections, originating from an off-angle position, are partially phase cancelled due to the delays set upon 1406a-1406i. Output information signal 106 can thus be transmitted at a lower power than is required for systems that do not have as high a SNR. That is, systems that are not optimized to receive a transmitted signal at maximum gain require a higher-power transmission, in case the signal is received off-peak and/or the noise is not partially phase cancelled, making the SNR relatively low. In the present embodiment, however, the signal is received on-peak and most reflected signals are partially phase cancelled so the SNR is relatively high. The power of the signal thus need not be as strong. This technique is therefore useful in an environment where low-power signals are preferable, such as the human body where signals are passing through live tissue.

Another advantage of the phased array design is that the potential angles of reception are extremely wide for an instance of the technology, whereas a larger receiver to provide signal gain is typically very narrow. For example, an example element nine times the size of transducer 1402 would provide potentially the same gain as the FIG. 14 array; however, this occurs only when device 104 is perpendicular to a flat receiving side of a large element. Furthermore, at an angle of 45 degrees, for example, the combined signal received by an maximized array far exceeds the output of the same single element nine times larger. This is due to the wavefront cancellation within a large element on an off-perpendicular wavefront, such as is the case for an acoustic signal transmitted and received within a human body 102.

Further, once the location of ingestible capsule 104 is determined, phased array 1400 can also be used to focus an information exchange signal on ingestible capsule 104 in order to send information from phased array 1400 to ingestible capsule 104. To do this, a known phase delay 1406a-1406i, such as a captured configuration from a signal reception, is implemented into a signal transmitted from an amplifier 1412, with the resulting phase delayed signal routed to transducers 1402a-1402i respectively. Because the transmission is focused on ingestible capsule 104, such that the point of maximum gain intersects with the location of ingestible capsule 104, either a lower average power signal may be used. Alternatively, a less sensitive (lower power) receiver design within sensor device 104 may be used.

Although locationing and information exchange are described in FIG. 14 with respect to a phased array in a single sensor link module, one of skill in the art will recognize that improved resolution may be provided when additional sensor link modules, each having its own phased array, are used. Furthermore, one of skill in the art will also recognize that multiple phased array devices can utilize phase-only information for the accurate determination of the location of sensor device 104, as multiple intersecting lines derived from multiple angles intersect at a point of origin of the signal from device 104.

In an alternate embodiment, multiple single element receivers and/or sensor link modules 602 exist and forward signals received to computing device 108. As described earlier, a desired signal 104 may be incident upon each of sensor link modules 602 in combination with reflections from a variety of body parts within and on (e.g., located on the skin of) human 102. Therefore, a computing device 108 can create a complex mathematical model (e.g., a Fourier transform) of the complex signal received. Given a particular received frequency of operation F1 of sensor device 104, computing device 108 may derive a close proximity to actual signals received by a combination of F1 at an amplitude A1, and phase P1; a second harmonic at frequency F2 (necessarily at F1×2), its amplitude A2, and phase P2, and so on for $3^{rd}$ harmonic, $4^{th}$ harmonic, and further frequencies as is well known as a Fourier transform. The closeness to actual signals is primarily a function of how many harmonics can be evaluated, and the resolution of amplitude and phase. Furthermore, computing device 108 performs this Fourier transform on each of the associated sensor link modules 602. The resulting analysis can be utilized to algorithmically combine signals from sensor link modules 602 for a maximum signal reception. Additionally, it can be utilized to minimize an out of phase reflection (considered in this case as noise).

In a further implementation of this embodiment, the resulting analysis of a received signal 104 at sensor link modules 602 can be utilized in a reverse manner, regenerating known frequencies, phases, and amplitudes of harmonics F1, F2, F3, and so on. This Inverse Fourier transform provides an environment of three (or more) transmitted waveforms from multiple sensor link modules 602 that maximally constructively interfere, with all reflection points in the body considered, at the point of the original signal received from device 104. Additionally, this process must be repeated for each location of device 104, location of sensor link modules 602 collectively, and for each transmitting frequency utilized. A person skilled in the art will recognize that the exemplified embodiment above utilizing three sensor link modules 602 may also utilize any number of sensor link modules 602 to afford a desired level of accuracy, including one sensor link module 602.

VI. Acoustic Biobus

The ability to modulate information into an acoustic transmission, coupled with the ability to focus the reception and/or transmission of the signal on a particular location to achieve maximum gain makes it possible to use acoustic waves for many applications in addition to communication with an ingestible sensor device or multiple sensor devices.

Figure 15:
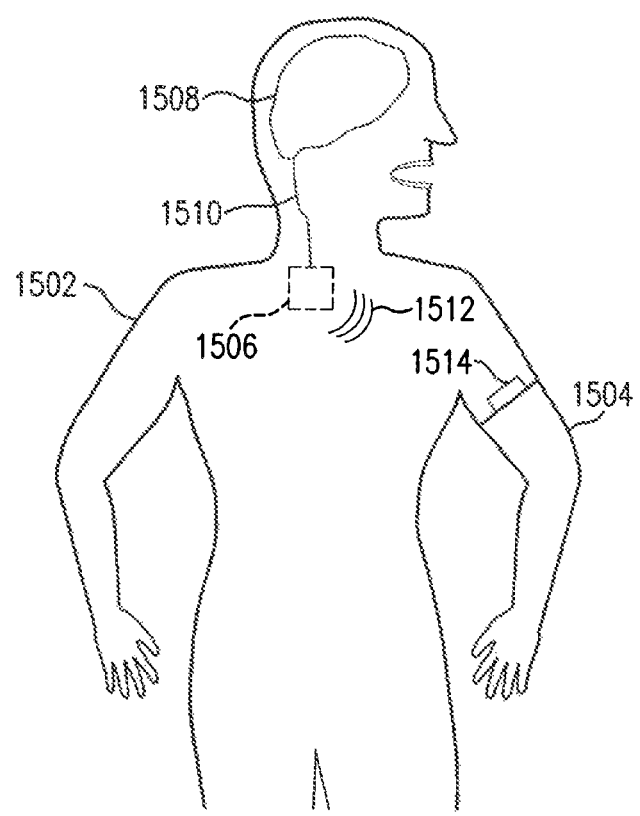
FIG. 15 is an illustration of an acoustic biobus according to an embodiment of the present invention.

One such application is communication with and control of implanted devices, such as prosthetic controls. Currently, prosthetics require a significant amount of wires and data paths (collectively referred to herein as a wiring harness) to effect movement of the prosthetic. According to an embodiment of the present invention, an internal acoustic biobus replaces or supplements the wiring harness of the prosthetic. FIG. 15 illustrates an exemplary biobus system according to an embodiment of the present invention. A human 1502 has a prosthetic limb 1504. An implanted prosthetic control unit 1506 receives signals from brain 1508 via connection 1510. Prosthetic control unit 1506 interprets the signals received from brain 1508 and modulates them into an instruction signal. The instruction signal is transmitted by prosthetic control unit 1506 as an acoustic information signal 1512. Acoustic information signal 1512 is received by a prosthetic operation unit 1514, which causes prosthetic limb 1504 to function accordingly. An acoustic biobus in accordance with this embodiment reduces or eliminates the wiring harness used for prosthetic limb 1504. Additionally, information is transmitted in a format friendly to human tissue, namely, acoustic format. Use of an acoustic biobus also reduces or eliminates the susceptability of prosthetic limb 1504 to interference from environmental noise, such as cellular telephone transmissions and many other forms of radio frequency communications common in today's society.

Similarly, acoustic information signals may be communicated between implantable devices, such as pacemakers, and external status and control devices.

VII. Modulation and/or Demodulation Methods

Communications module 204 (FIG. 2) may be configured to modulate information from sensor output signal 212 with a carrier frequency to generate acoustic output signal 106 according to a variety of modulation techniques. Such techniques include, for example and without limitation, amplitude modulation (AM), frequency modulation (FM), phase modulation (PM), pulse-width modulation (PWM), and pulse-position modulation (PPM), and any combination of these modulation techniques, including in-quadrature or other modulation schemes. Previous schemes have been used for short commands, such as that described in U.S. Pat. No. 7,024,248 to Penner et al., incorporated herein by reference in its entirety. Such previous schemes used for short commands do not consider difficulties present in long term and/or long stream data transmission, or communication with an ingestible capsule. For example, such previous schemes do not account for the multiple acoustic reflections and noise that may interfere with longer periods of transmissions.

Modulation schemes are also discussed in U.S. Pat. Publication No. 2008/0112885 A1 titled "System and Method for Acoustic Data Transmission," and U.S. Pat. No. 8,615,284, titled "System and Method for Acoustic Information Exchange Involving an Ingestible Low Power Capsule," each of which is incorporated herein by reference, both generally and as they pertain to acoustic data modulation/demodulation schemes.

Before further discussion of specific acoustic data transmission methods, it is important to describe the general acoustic environment of the medium, in this case human 102 (and similar for most animals of approximate size). Specifically, it is important to note i) how to transduce a signal, ii) what noise is to be considered, both external and internal, and iii) what methods to use to best decode the signal in the presence of the second item, noise.

When designing a transducer, well known principles apply to matching with transmitted medium. For example, a radio frequency antenna will launch electromagnetic waves into its environment, which includes air, buildings, etc. It is designed to assume contact with a certain medium (generally air). Similarly, a design of a speaker (and enclosure) is designed to be most efficient when operational at a certain normal air pressure (such as sea level). An exemplary transducer that may be used in embodiments of the present invention assumes a characteristic environment of a human body 102.

Such a transducer needs to be appropriate for use within a human body, for example in contact with human tissue. Greatly different from a speaker design in contact with air, a fluid possesses a different set of characteristics. For instance, a speed of an acoustic wave in air at sea level is approx 350 meters per second. However, a speed of an acoustic wave in an animal tissue is approx 1500 meters per second. Additionally, a force required to move a volume of air is substantially different from a force required to move a volume of tissue. Thus, when designing a transducer for a human tissue, a most efficient design comes as close as possible to matching the impedance of the medium (for example, closely matching a speed of an acoustic wave).

Additionally, it is useful for a transducer design to focus energy in the direction of a receiver for maximal use of energy. However, the transducer design needs also to be able to be efficient in energy transfer for most, if not all, potential locations of a receiver when the transducer is mobile. In the case of an ingestible sensor device, such as ingestible sensor device 104, in a human body, the receiver is very mobile as it transcends the full gastrointestinal tract.

Once a signal can be efficiently transmitted into a medium, the noise in the environment should be accounted for, both from an aspect of external noise, but also an aspect of self-generated noise due to reflections from a variety of materials. When working with radio frequencies (RF), as commonly as they are used a key study is in the external impact of unwanted signals from other unknown transmitters, characterized as noise. Conversely, when evaluating an acoustic environment within a human body, very little, if any, noise is present from other transmitters, given an ultrasonic frequency range. One of very few applications of ultrasonic signals upon a human body is in the case of ultrasound—an imaging technique by use of ultrasonic signals. However, this is not present for a general population, and a patient is typically under a doctor's care when ultrasonic frequencies are being transmitted into the body. Additionally, ultrasonic frequencies used exterior to the human body would need to convey internal to the body in order to interfere with an internal transducer. Although this is possible, it is unlikely as a result of the large difference in impedance of air and human tissue. Ultrasonic frequencies, as a result, mostly bounce off the human skin to return to the air medium from which they originated.

Additionally, some common uses of RF transcend long distances almost entirely in air, such as with cellular telephony. In these cases, reflections are reasonably spaced with respect to time, and are also very modestly attenuated with respect to power at a receiver. An ultrasonic environment within a relatively confined space, such as a human body, presents a difficult noise model. Since there are bones, air pockets, differing tissues, sacks of liquids, dynamic resonating cavity effects due to breathing, heart beat, larynx, moving fluid such as blood flow in blood vessels, etc., causing Doppler shifting, all within close proximity (tens and hundreds of wavelengths as opposed to tens and hundreds of thousands of wavelengths) to a transmitter and receiver, very complex waveforms are received at the receiver. These waveforms may be a combination of a multitude of re-transmitted waveforms in the form of reflections from the original transmitted waveform imposed upon the original waveform. Further complicating the acoustic model is the human skin. The skin is an effective reflector. As effective as the skin is in reflecting airborne ultrasonic transmissions, it also reflects a substantial amount of incident energy from within. Reflections may include a reflected original wavefront, but also a reflected complex wavefront built with all of the other reflected wavefronts from the variety of organs and materials within the body.

Timing of these reflections leads to an evaluation in three scenarios. A first timing scenario occurs when an original waveform is received prior to any substantial reflected waveforms from the original, referred to herein as 'clear channel'. A second timing scenario occurs during reception of some but not all of the complex wavefronts caused by some but not all of the reflections, referred to herein as 'transitionary channel'. A third timing scenario occurs after all reflections have substantially stabilized, herein referred to as 'standing wave channel'. It is noted that the standing wave channel is an adiabatic approximation, valid for acoustic event time periods much shorter than the dynamic changes in the resonating cavity, due to body functions such as heart beating and breathing. It is most important to note that a modulation of a carrier frequency (a traditional method of encoding data upon a frequency) in any of amplitude, frequency, or phase, imposes a same environment study as does turning a carrier on and off (the extreme of amplitude modulation). The acoustic environment may therefore be analyzed to determine clear channel, transitionary channel, and standing wave channel characteristics from the time period of the implementation of the modulation.

Differing technologies may apply to the three differing timing scenarios described above, or potentially a combination of multiple technologies to make use of multiple timing scenarios. For example, an embodiment of the present invention utilizes frequency hopping in order to maintain operation within a first timing scenario, clear channel. For continuous operation, frequencies are changed prior to the transitionary channel. As long as the frequency being hopped to was not previously sent or is completely attenuated from a previous transmission, it will be presented with a clear channel. In another example embodiment, a system makes use of a standing wave channel. Additional details of modulation schemes according to these and other embodiments of the present invention follow.

A. Drone Frequency

For example, in an embodiment, FM may be used to send the output information signal 106 from ingestible capsule 104, in a variety of schemes. For instance, an example FM protocol that can handle multiple sensors 202a-202c is described below:

$F_{Drone}$=a drone frequency,
$F_0$=a frequency for bit zero,
$F_1$=a frequency for bit 1.
$F_i$ an information frequency, where i=a, b, c, etc for sensors 202a-202c, respectively, and
$F_{ID}$=a frequency sequence of zero bits ($F_0$) and one bits ($F_1$) for an identification number of the particular ingestible sensor device 104.

The drone frequency $F_{Drone}$ is used to provide a detectable separation between frequencies Fa, Fb, and Fc related to information from sensors 202a-202c. The presence of drone frequency $F_{Drone}$ may not be required in all implementations. Frequencies Fa, Fb, and Fc may have frequency ranges that are non-overlapping so that communications related to sensors 202a-202c can be distinguished from each other. In an embodiment, after an ingestible capsule 104 is swallowed, the swallowed ingestible capsule 104 is configured to serially send out the following frequency sequence:

$F_{Drone} F_{ID} F_{Drone} F_a F_{Drone} F_b F_{Drone} F_c F_{Drone} F_{ID} F_{Drone}$ Thus, in a first time slot ($F_{Drone}$), ingestible capsule 104 transmits the drone frequency $F_{Drone}$. In a second time slot ($F_{ID}$), ingestible capsule 104 transmits the identification number for the particular ingestible capsule 104 as a series of 0 and 1 bits, respectively represented by frequencies $F_0$ and $F_1$. The identification number may be useful, for example, when more than one ingestible capsule 104 is transmitting from inside human 102.

In a third time slot ($F_{Drone}$), ingestible capsule 104 transmits the drone frequency $F_{Drone}$. In a fourth time slot ($F_a$), ingestible capsule 104 transmits information related to sensor 202a. The information is transmitted at a central frequency of $F_a$ that varies in frequency in a manner according to information from sensor output signal 212a. Thus, information from sensor 202a is transmitted in the fourth time slot. In a fifth time slot ($F_{Drone}$), ingestible capsule 104 transmits the drone frequency $F_{Drone}$. In a sixth time slot ($F_b$), ingestible capsule 104 transmits information related to sensor 202b. The information is transmitted at a central frequency of $F_b$ that varies in frequency in a manner according to information from sensor output signal 212b. Thus, information from sensor 202b is transmitted in the sixth time slot. In a seventh time slot ($F_{Drone}$), ingestible capsule 104 transmits the drone frequency $F_{Drone}$. In an eighth time slot ($F_c$), ingestible capsule 104 transmits information related to sensor 202c. The information is transmitted at a central frequency of $F_c$ that varies in frequency in a manner according to information from sensor output signal 212c. Thus, information from sensor 202c is transmitted in the eighth time slot. In a ninth time slot ($F_{Drone}$), ingestible capsule 104 transmits the drone frequency $F_{Drone}$. In a tenth time slot ($F_{ID}$), ingestible capsule 104 transmits the identification number for the particular ingestible capsule 104. In an eleventh time slot ($F_{Drone}$), ingestible capsule 104 transmits the drone frequency $F_{Drone}$. In subsequent time slots, information related to sensors 202a-202c can be further transmitted at frequencies $F_a$-$F_c$, and the identification number $F_{ID}$, can be further transmitted, separated by the drone frequency $F_D$ as desired.

This frequency sequence may be received, and due to the ordering of frequency signals, and the different frequencies used, the received information from sensors 202a-202c can be demodulated and stored in an organized manner.

In such embodiments, information from any number of sensors 202 can be accommodated. In some embodiments, the drone frequency $F_D$ may not be necessary. Furthermore, in some embodiments, the identification number sequence, $F_{ID}$, may not be necessary (e.g., if identical ingestible capsules 104 are individually used by human 102). Any length of identification number may be used.

A time interval, $T_d$, may be used for each of the time slots described above. The time interval $T_d$ may be bounded by a minimum time interval for $T_d$, $T_{dmin}$, and a maximum time interval for $T_d$, $T_{dmax}$. As discussed above, the minimum time interval, $T_{dmin}$, is determined by noise issues. Here, either the standing wave model or the clear channel model is employed. If the standing wave approach is applied, then the system needs to wait for the signal to stabilize to a standing wave. If the clear channel approach is chosen, then the system needs to wait for the signal to decay before sending out a new signal on the same frequency. The maximum time interval, $T_{dmax}$, may be determined by power consumption issues (such as a charge lifespan of battery 702) of ingestible capsule 104. Furthermore, a duty cycle, $T_c$, may be used for the time slots described above. The duty cycle, $T_c$, may be bounded by a minimum duty cycle length, $T_{cmin}$, and a maximum duty cycle length, $T_{cmax}$. The minimum duty cycle, $T_{cmin}$, may be determined by requirements of the particular diagnostic test(s) to be performed by ingestible capsule 104, and the maximum duty cycle, $T_{cmax}$, may be determined by power consumption issues (such as a charge lifespan of battery 702) of ingestible capsule 104.

B. Spread Spectrum i. Overview

An embodiment of the present invention is directed to acoustically transmitting data (such as communication signal 106) from a transmitter (such as ingestible capsule 104) to a receiver (such as sensor link module 602). In this embodiment, a high data rate is achieved by spreading acoustic data signals within a bandwidth considerably exceeding the data bandwidth. The spreading scheme is based on quasi-orthogonal spreading codes having substantially zero auto-correlation functions. Advantageously, the spreading scheme is combined with efficient modulation schemes, thereby considerably mitigating inter-symbol interference and providing reliable system performance. In addition, the spreading code and modulation schemes can be easily implemented using hardware components to reduce power consumption within and the size of ingestible capsule 104.

An acoustic transmission system according to an embodiment of the present invention includes a transmitter and a receiver. A data source provides a sequence of data symbols, which may be binary or M-ary symbols. An acoustic transmitter transforms the sequence of data symbols into an acoustic signal by an encoding procedure and acoustic carrier modulation. Sometimes the acoustic transmitter adds a preamble packet (preamble) for synchronization and channel parameters estimation at the receiving site.

Acoustic waves, radiated by the transmitter, propagate through an acoustic channel. The acoustic waves reach the receiver by several paths, reflecting from different objects, surface areas, surface boundaries and interfaces in the environment. This multi-path propagation provides a complex interference of acoustic rays, having different attenuation, phase and delay. Each acoustic ray has instable (variable) amplitude and phase (fading) because it includes several sub-rays with insignificant delay variations.

An acoustic receiver receives random noise and the acoustic signals transmitted by the transmitter. The acoustic receiver transforms the additive mixture of noise and delayed signals into data symbols using a demodulation and decoding procedure as described herein.

ii. An Example System

Figure 17:
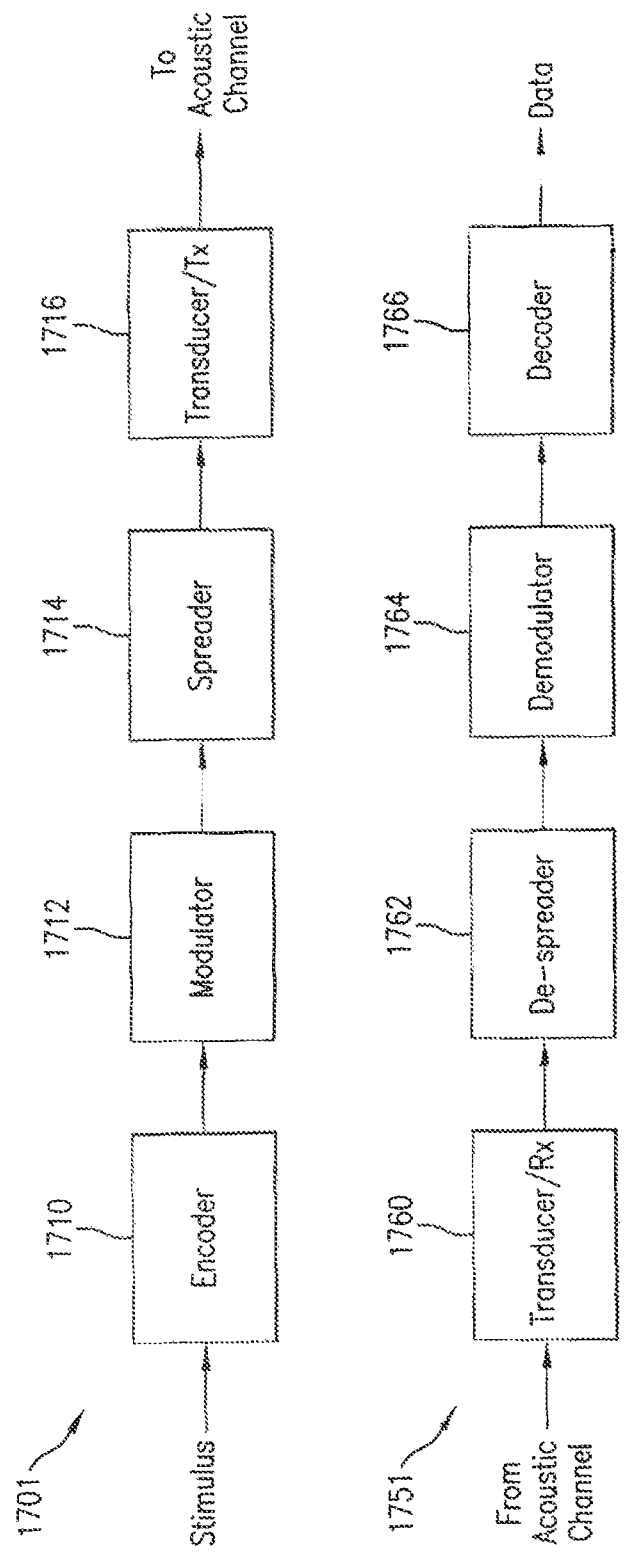
FIG. 17 illustrates a block diagram of an acoustic data transmission system utilizing a spreading code according to an embodiment of the present invention.

FIG. 17 depicts a block diagram illustrating an example acoustic data transmission system according to an embodiment of the present invention. The acoustic data transmission system of FIG. 17 includes a transmission path 1701 and a receive path 1751. In an embodiment, transmission path 1701 is included in ingestible capsule 104 and receive path 1751 is included in sensor link module 602.

Transmission path 1701 includes an encoder 1710, a modulator 1712, a spreader 1714, and an acoustic transducer (transmitter) 1716. Transmission path 1701 serves to encode and modulate data to generate an acoustic signal that is transmitted through the body of human 102. Each element of transmission path 1701 is described in more detail below.

Encoder 1710 encodes data symbols from a data source (such as sensor output signal 212). The encoding scheme may include discrete transformations of data symbols, including adding redundant symbols for forward error correction (FEC).

Modulator 1712 modulates the encoded discrete signal with a carrier. In an embodiment, modulator 1712 uses a narrow band modulation scheme, such as phase shift keying (PSK), frequency shift keying (FSK), quadrature amplitude modulation (QAM), or the like, as described in more detail below. Modulator 1712 includes a carrier generator (not shown).

Spreader 1714 spreads the modulated signal according to a spreading code, causing the modulated signal to be spread within a bandwidth that considerably exceeds the data bandwidth. In an embodiment, a spectrum of the modulated signal is increased by a factor of N, wherein N is the spreading factor of spreader 1714. Characteristics of the spreading code implemented by spreader 1714 are described below.

An ideal orthogonal spreading code sequence would completely eliminate any interference between a signal $S_r(t)$ and a time delayed version of that signal $S_r(t+\tau)$. Mathematically, the amplitude A of the interference between an ideal orthogonal spreading code satisfies the following equation:

$$A = \frac{1}{T}\int_0^T S_r(t)S_r(t+\tau)\,dt = 0, \text{ for any } |\tau| > T/N \quad \text{(Eq. 1)}$$

where [0,T] is the data symbol interval, T is the data symbol duration, and N is the spreading factor.

Rather than implementing the ideal orthogonal spreading code of equation (1), spreader 1714 implements a quasi-orthogonal spreading code. The quasi-orthogonal code implemented by spreader 1714 reduces interference between a signal $B_r(t)$ and a time-delayed signal $B_r(t+\tau)$ by a factor of N, wherein N is the spreading factor. In an embodiment, spreader 1714 implements a quasi-orthogonal Barker code B(t), satisfying the following equation:

$$A = \frac{1}{T}\left|\int_0^T B(t)B(t+\tau)\,dt\right| = N, \text{ for any } \tau = 0 \quad \text{(Eq. 2a)}$$

$$A = \frac{1}{T}\left|\int_0^T B(t)B(t+\tau)\,dt\right| \leq 1, \text{ for any } \tau > T/N \quad \text{(Eq. 2b)}$$

In this case spreading factor N is a number of binary elements ±1 within the Barker sequence (within the data symbol interval T). Equation (2) shows that side lobes of the Barker autocorrelation function do not exceed the N-th fraction of the main lobe. Thus, all widespread acoustic rays (i.e., rays which are time-delayed by more than a factor of T/N relative to the Barker sequence in the receiver) are suppressed by N times.

Spreader 1714 implements the spreading code by one or more linear operations. These linear (parametric) operations may simply comprise multiplication of the modulated signal and a spreading code sequence as described below, although other methods for spreading the modulated signal may be realized without deviating from the spirit and scope of the present invention. In an embodiment, spreader 1714 implements an 11 element Barker sequence, as described in more detail below. Other Barker sequences may be used. There are Barker sequences for N=2, 3, 4, 5, 7, 11, 13. For N>13 there are not quasi-orthogonal binary sequences with A≤1. Nevertheless there are sequences with length up to N=28 for A≤2, and sequences with length up to N=34 for A≤3. For larger N, linear recurrent M-sequences (pseudo-random binary sequences) may be used for signal spectrum spreading; they provide about √N times suppression of the delayed rays.

Returning to FIG. 17, the signal from the output of spreader 1714, having N times more bandwidth than the data symbol spectrum, is fed to acoustic transducer/Tx 1716 (such as acoustic transducer 904 described above). Acoustic transducer/Tx 1716 converts the electrical signals from transmission path 1701 into acoustic signals which are then transmitted through the multi-path acoustic channel in the body of human 102.

After traveling through the multi-path acoustic channel, the acoustic signal is received by receive path 1751 illustrated in FIG. 17. Receive path 1751 includes an acoustic transducer (receiver) 1760, a de-spreader 1762, a demodulator 1764, and a decoder 1766. At the receiving site, the signal from the output of acoustic transducer/Rx 1760 is subjected to the opposite sequence of transformations compared to transmission path 1701. Although the sequence of transformations is reversed, the implementation of each method may differ substantially as ingestible capsule 104 is designed to be small and low power, while the same constraints do not necessarily apply to sensor link module 602. A variety of implementations for transmit and receive paths are anticipated and do not depart from the spirit and scope of this invention. De-spreader 1762 transforms the received wideband signal into the initial narrowband modulated signal by synchronized multiplication of the wideband signal with the spreading code. Demodulator 1764 demodulates the narrowband signal using signal processing based on coherent or non-coherent detection schemes. Decoder 1766 distinguishes data symbols from the demodulated signals, based on soft or hard decision decoding procedures. It should be noted that both de-spreader 1762 and demodulator 1764 are controlled by a synchronization function (not shown in the FIG. 17).

It is to be appreciated that transmission path 1701 and receive path 1751 are presented for illustrative purposes only, and not limitation. Variations of transmission path 1701 and/or receive path 1751 can be implemented without deviating from the spirit and scope of the present invention. For example, modulator 1712 can be implemented after spreader 1714. As another example, some filtration elements—such as a band-pass filter (BPF) or low-pass filter (LPF)—may be used in both transmission path 1701 and receive path 1751. In such examples, a narrowband BPF is used after de-spreader 1762. Such filtration elements are not depicted in FIG. 17, although their inclusion is within the spirit and scope of the present invention, as would be apparent to a person skilled in the relevant art(s).

iii. Example Encoding Schemes (a) Phase Shift Keying

Figure 18:
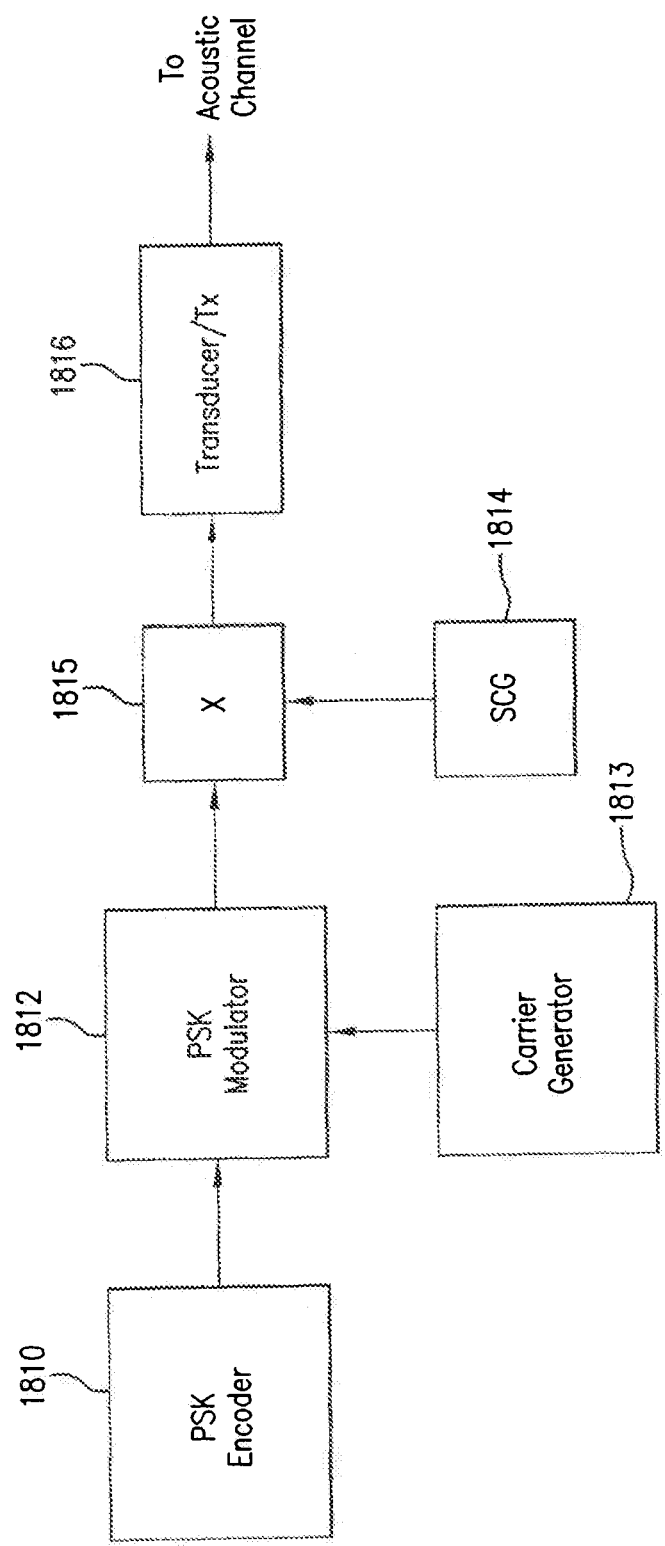
FIG. 18 illustrates a block diagram of an acoustic transmitter that utilizes a phase shift keying (PSK) modulation scheme and a spreading code according to an embodiment of the present invention.
Figure 19:
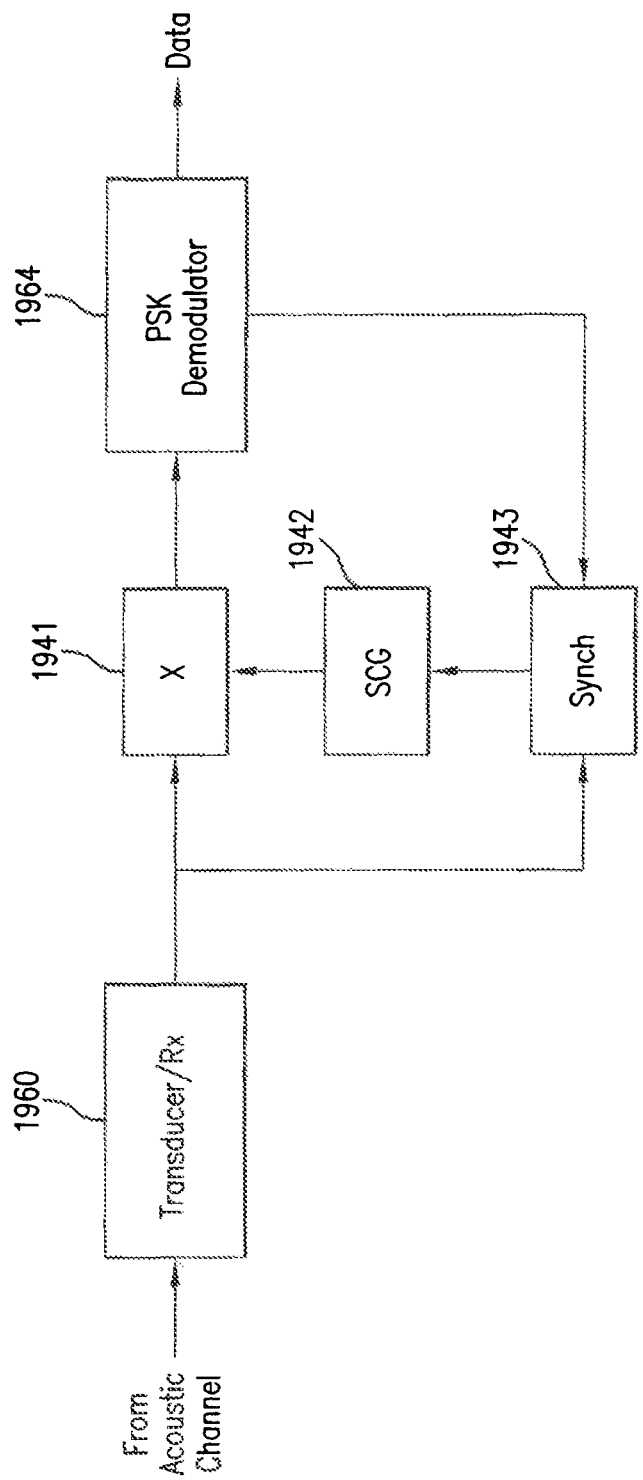
FIG. 19 illustrates a block diagram of an acoustic receiver of an acoustic data transmission system that utilizes a PSK modulation scheme and a spreading code according to embodiments of the present invention.

FIGS. 18 and 19 depict block diagrams respectively illustrating a transmission path and a receive path of an acoustic data transmission system based on PSK modulation in combination with a spreading code according to an embodiment of the present invention. The transmission path of FIG. 18 may be implemented in ingestible capsule 104 and the receive path of FIG. 19 may be implemented in an external receiver patch, such as sensor link module 602.

Referring to FIG. 18, the transmission path includes a PSK encoder 1810, a PSK modulator 1812, a carrier generator 1813, a spreading code generator (SCG) 1814, a multiplier 1815, and an acoustic transducer/Tx 1816. PSK encoder 1810 together with PSK modulator 1812 and carrier generator 1813 provide the phase modulated signals. The particular functions of PSK encoder 1810 and PSK modulator 1812 depend on the type of PSK modulation scheme—whether binary PSK, binary differential PSK, M-ary PSK or M-ary DPSK, or the like. For example, if the modulation scheme is implemented as binary PSK, then PSK encoder 1810 and PSK modulator 1812 may be implemented as a simple logic multiplier. If the PSK modulation scheme is implemented as DBPSK, then PSK encoder 1810 includes a binary multiplier and a binary delay element (see, e.g. FIGS. 20 and 22 below), and PSK modulator 1812 includes a simple multiplier. In the case of M-ary PSK or M-ary DPSK, for instance, QPSK or DQPSK, PSK encoder 1810 may be implemented as a Gray-code encoder, and PSK modulator 1812 may be implemented as an I/Q modulator according to known schemes.

The phase modulated carrier from the output of PSK modulator 1812 is fed to multiplier 1815, where it is multiplied by the spreading sequence, generated by SCG 1814. SCG 1814 generates the spreading sequence synchronously with the modulated symbols at the output of PSK modulator 1812.

The wideband signal at the output of multiplier 1815 is fed to acoustic transducer/Tx 1816. Acoustic transducer/Tx 1816 transmits the acoustic signal into the multi-path acoustic channel as described above.

After traveling through the multi-path acoustic channel, the acoustic signal is received by the receive path of FIG. 19. The receive path includes an acoustic transducer/Rx 1960, a multiplier 1941, a SCG 1942, a synchronization unit (synch) 1943, and a PSK demodulator 1964. Acoustic transducer/Rx 1960 receives the acoustic signal and converts it into an electrical signal. SCG 1942 and PSK demodulator 1964 are controlled by synch 1943, which uses both the received signal from the output of acoustic transducer/Rx 1960 and output signals from PSK demodulator 1964. The particular functions and schemes of PSK demodulator 1964 depend on both the PSK type and signal processing algorithm. For example, if it is PSK, the conventional coherent scheme based on the carrier recovery technique is used. If it is DPSK, the conventional I/Q non-coherent scheme or even the simplest autocorrelation scheme may be used.

(b) Differential Phase Shift Keying

Figure 20:
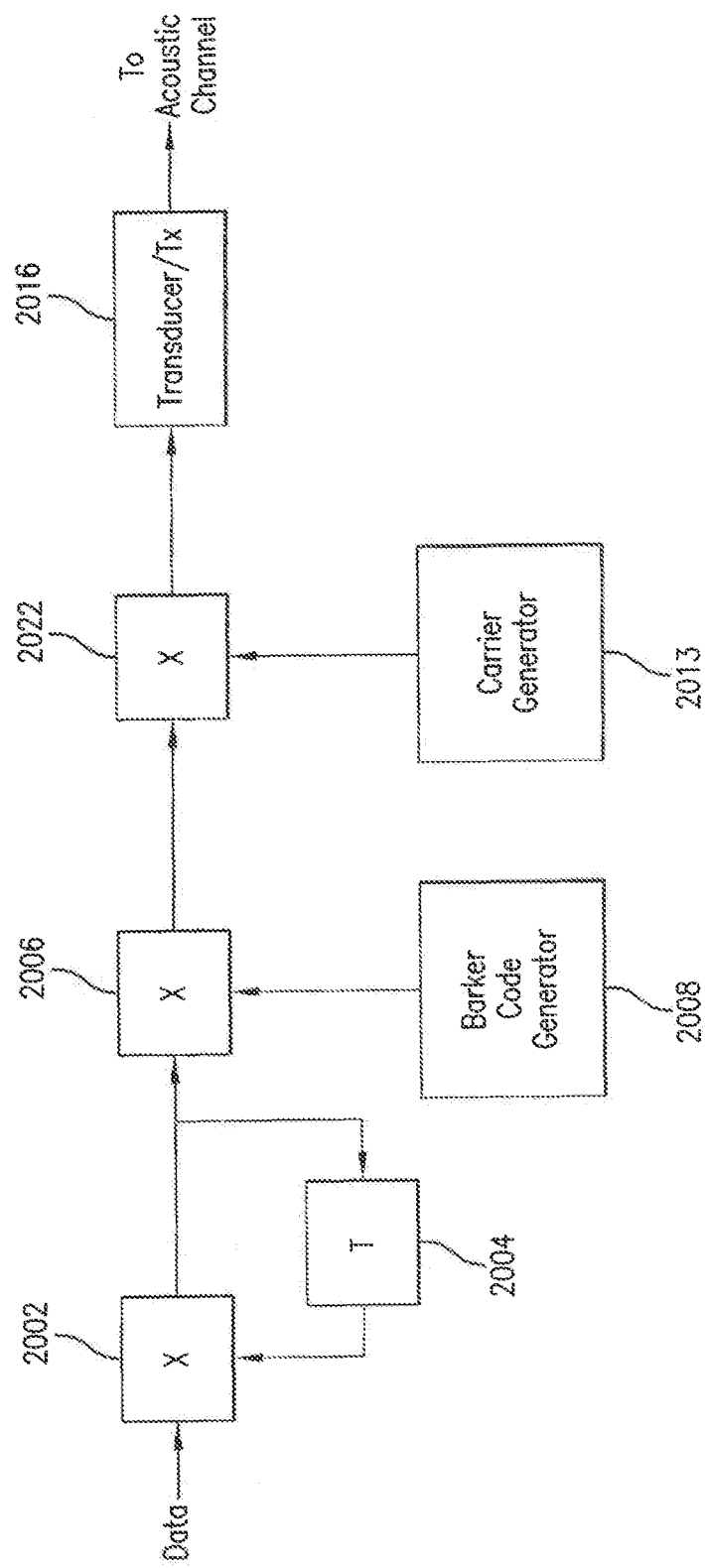
FIG. 20 illustrates a block diagram of a transmitter of an acoustic data transmission system that utilizes a differential PSK (DPSK) modulation scheme and a Barker spreading code according to an embodiment of the present invention.
Figure 21:
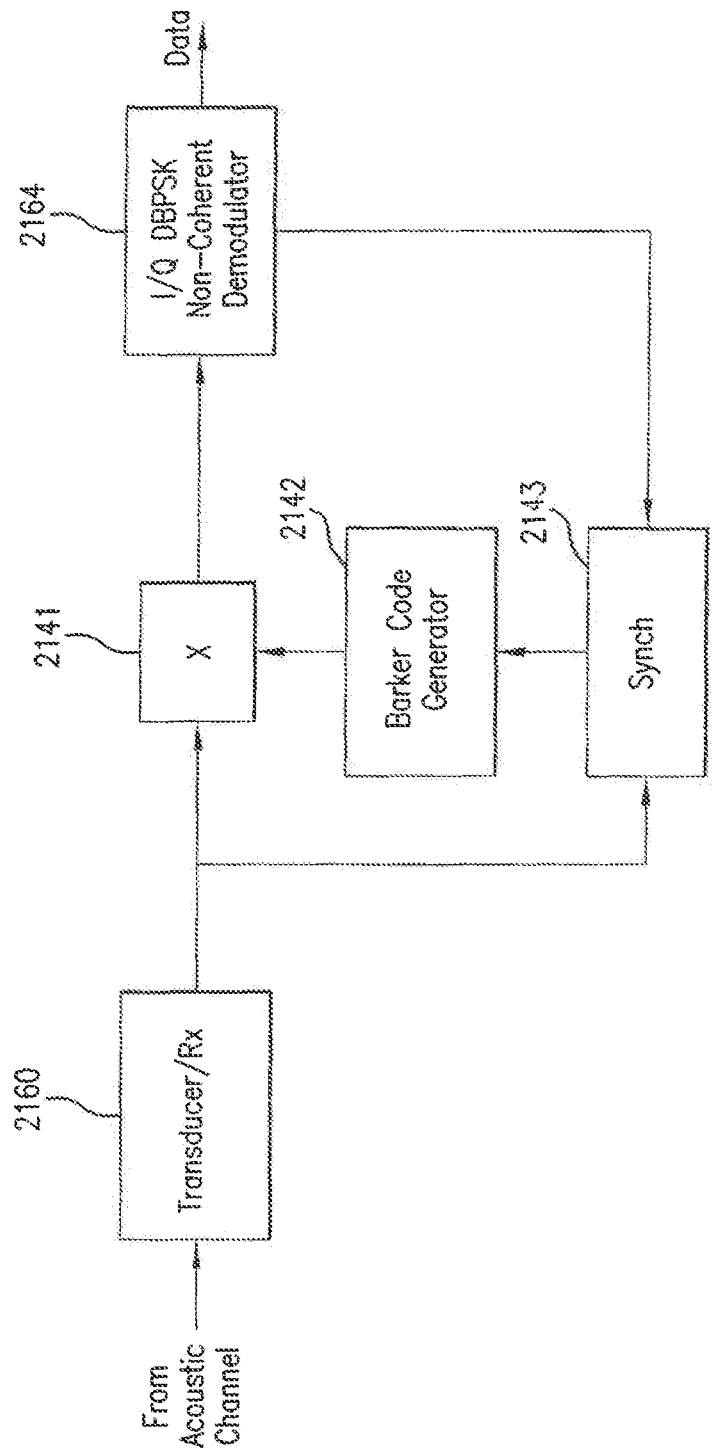
FIG. 21 illustrates a block diagram of a receiver of an acoustic data transmission system that utilizes a DPSK modulation scheme and a Barker spreading code according to an embodiment of the present invention.

FIGS. 20 and 21 depict block diagrams respectively illustrating a transmission path and a receive path of an acoustic data transmission system based on DBPSK in combination with a Barker spreading code according to an embodiment of the present invention. The transmission path of FIG. 20 may be implemented in ingestible capsule 104 and the receive path of FIG. 21 may be implemented in an external receiver patch, such as sensor link module 602.

The transmission path of FIG. 20 includes a multiplier 2002, a delay element 2004, a multiplier 2006, a Barker code generator 2008, a multiplier 2022, a carrier generator 2013, and an acoustic transducer/Tx 2016. Referring to FIG. 20, the DBPSK encoder includes multiplier 2002 and a (one bit) delay element 2004. In this scheme, a current data bit $b_k$ in form of ±1 is multiplied by a result of a previous multiplication $e_{k-1}$ after it goes through delay element 2004. Thus, the encoded bit $e_k$ that is submitted to multiplier 2006 can be written as $$e_k = e_{k-1} * b_k \tag{Eq. 3}$$

Barker code generator 2008 generates a Barker sequence. The encoded bit $e_k$ at the output of multiplier 2002 is subdivided into N equal parts by multiplication with the Barker sequence, containing N positive and negative ones, in multiplier 2006. Carrier generator 2013 generates a carrier. The spreaded signal from the output of multiplier 2006, containing N positive and negative ones, modulates the carrier in multiplier 2022. The modulated carrier is fed to acoustic transducer/Tx 2016 and transmitted into the multi-path acoustic channel.

After traveling through the multi-path acoustic channel, the acoustic signal is received by the receive path of FIG. 21. The receive path includes an acoustic transducer/Rx 2160, a multiplier 2141, a Barker code generator 2142, a synch 2143, and a demodulator 2164. Acoustic transducer/Rx 2160 receives the acoustic signal and converts it into an electrical signal. Barker code generator 2142 and demodulator 2164 are controlled by synch 2143, which uses both the received signal from the output of acoustic transducer/Rx 2160 and the output signals from demodulator 2164. As illustrated in FIG. 21, demodulator 2164 is implemented as an I/Q DBPSK non-coherent demodulator, which provides a substantially perfect bit error rate (BER). In this embodiment, the BER is very close to the minimum possible BER (for example, BER=$10^{-3}$ at SNR≈8.0 dB), at the comparatively simple implementation, which does not include any carrier recovery procedure.

(c) First Order and Second Order Differential Phase Shift Keying

An embodiment of the present invention uses both first order and second order differential phase shift keying (DPSK). Such an embodiment may be implemented in combination with a spreading code, such as a Barker spreading code described herein. Using first and second order DPSK provides several advantages over conventional DPSK as described in more detail below.

(1) Carrier Frequency Instability Problem

Digital phase-modulated signals—such as BPSK and quadrature phase-shift-keying (QPSK)—potentially provide the highest possible performance (i.e., the lowest BER) in noisy channels, as well as in fading noisy channels. However, there are some well known difficulties for PSK technique application in channels with carrier frequency instability. If the carrier frequency changes slowly, the problem is conventionally solved by one or more of the following methods: (i) adaptive adjustment of the reference signal (carrier recovery techniques) at the receiver; (ii) periodical transmission of the reference signal (package preamble); and/or (iii) constant transmission of the reference signal in parallel with the data signal. Method (iii) is used in most advanced mobile wireless standards, such as WiFi, WiMax, LTE, and the like. Although these methods provide some advantages, they all decrease the data transmission performance and complicate the overall data transmission system.

Embodiments of the present invention that use PSK modulation in acoustic data transmission are also complicated by carrier frequency instability. In such embodiments, there are two main sources of the carrier frequency instability.

The first one is instability of carrier generation. For proper data transmission, the carrier frequency instability should be less than $10^{-4}$ in order to achieve a nominal bit error rate, for example. If the nominal carrier frequency F is equal to approximately 1 MHz and symbol duration T is equal to approximately 200 µs (10 kbit/s at QPSK), then the phase shift $\Delta\phi$ will be given by $$\Delta\phi = 2\pi\Delta FT = 2\pi*100*200*10^{-6} \approx 7.2°.$$

This phase shift does not destroy the system, but considerably decreases its performance. For example, in a conventional PSK system an instability of carrier generation equal to $10^{-3}$ completely degrades data transmission.

The second source of the carrier frequency instability in acoustic systems is the Doppler Effect. For example, if ingestible capsule 104 moves with speed 10 cm/s, then the frequency shift $\Delta F$ is $$\Delta F \approx (0.1/1500)*10^6 \approx 67 \text{ Hz},$$

and the phase shift $\Delta\phi$ is $$\Delta\phi = 2\pi\Delta FT = 2\pi*67*200*10^{-6} = 4.8°.$$

So, the total phase shift, caused by both the Doppler Effect and carrier generation instability, is about 12 degrees—i.e., about 27% of minimum distance between signal vectors at QPSK—and therefore carrier frequency instability is an important problem to overcome in PSK-based acoustic data transmission systems of embodiments of the present invention.

The above-mentioned methods for addressing the carrier frequency instability problem consume a significant amount of power, and are therefore not desirable for implementation in acoustic data transmission systems of the present invention. Thus, an embodiment of the present invention provides a solution to the above-mentioned carrier frequency instability problem changing the PSK signal structure, without complicating the acoustic transmitter and with few additions to the acoustic receiver.

(2) Acoustic Data Transmission Based on Two Types of DPSK

Embodiments of the present invention include an acoustic data transmission system based on two types of DPSK techniques: (i) $D^1$PSK, the first order DPSK, modulates the first finite differences of the carrier phase in the acoustic transmitter; and (ii) $D^2$PSK, the second order DPSK, modulates the second finite differences of the carrier phase in the acoustic transmitter. At the receiving site, the acoustic receiver does not use any carrier recovery techniques or adaptive frequency/phase adjustment procedures, but rather is based on direct calculation of current carrier phase (i.e., as it is in the acoustic channel).

Advantageously, these embodiments of the present invention are substantially independent of carrier phase offset (i.e., substantially invariant to the initial phase shift in the acoustic system) at both $D^1$PSK and $D^2$PSK. In addition, these embodiments include a two-mode transmitter ($D^1$PSK or $D^2$PSK) based on a simple universal differential encoder and conventional carrier phase modulator. Moreover, these embodiments include a $D^2$PSK receiver, providing both $D^1$PSK and $D^2$PSK signal processing, based on a simple double-differential autocorrelation decoder with only symbol synchronization and without any carrier synchronization.

Figure 25:
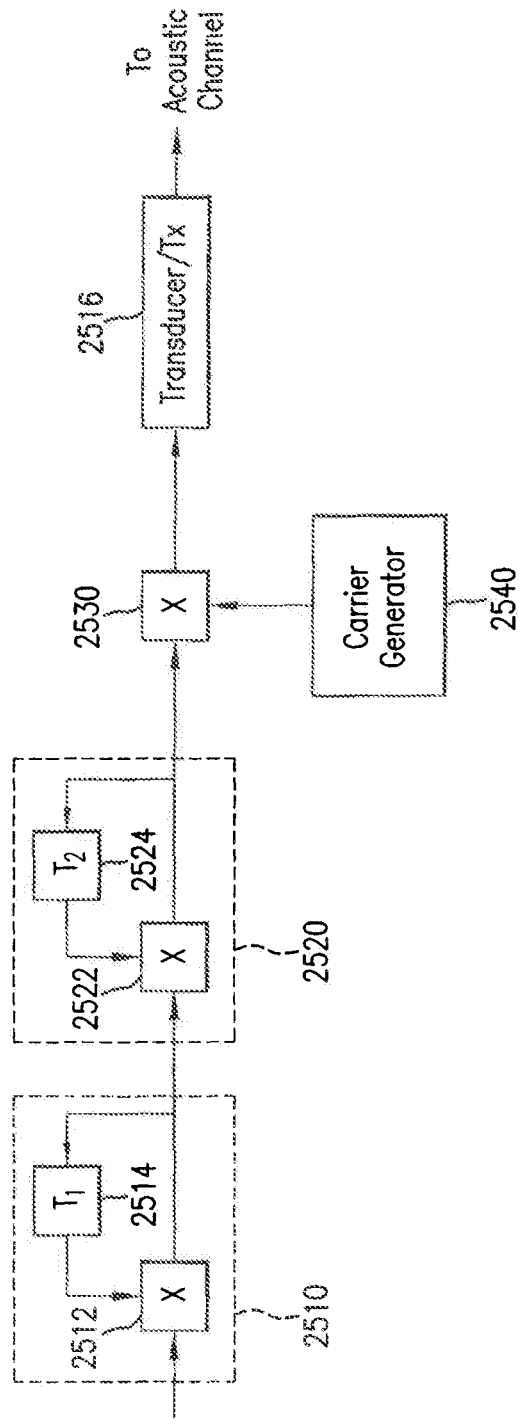
FIG. 25 illustrates a block diagram of a transmitter of an acoustic transmission system that uses two types of DPSK modulation according to an embodiment of the present invention.
Figure 26:
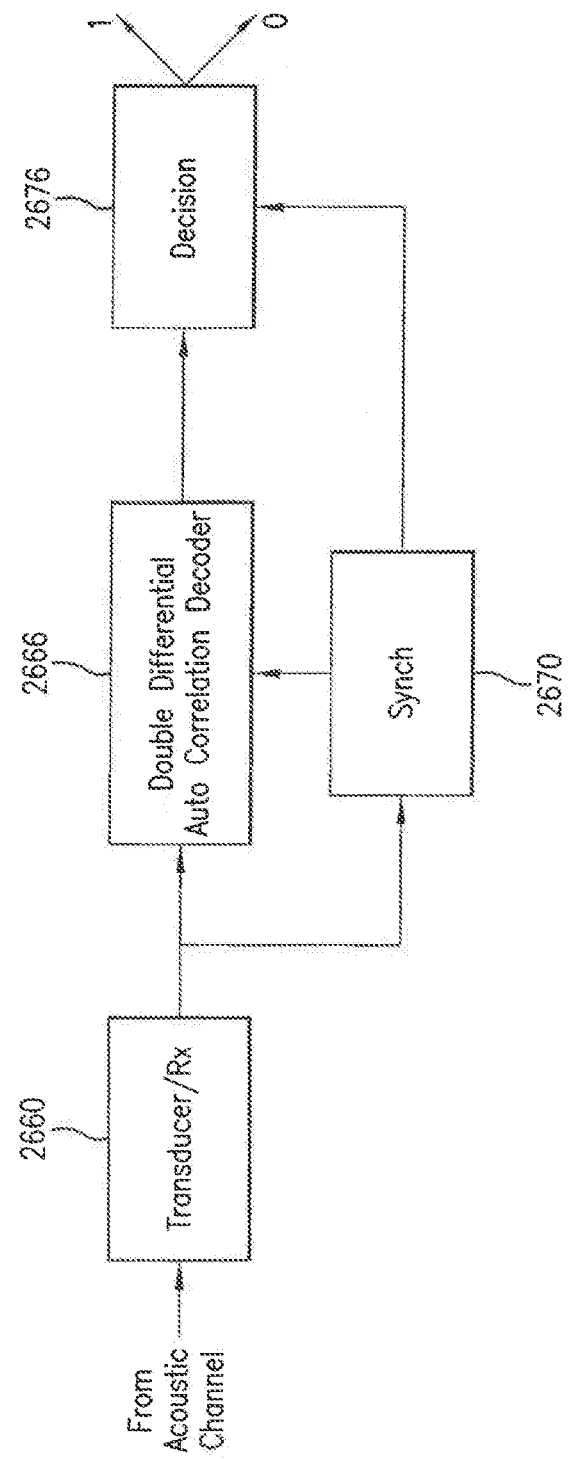
FIG. 26 illustrates a block diagram of a receiver of an acoustic transmission system that uses two types of DPSK modulation according to an embodiment of the present invention.

FIGS. 25 and 26 depict block diagrams respectively illustrating a transmission path and a receive path of an acoustic transmission system that uses two types of DPSK according to an embodiment of the present invention. The transmission path of FIG. 25 may be implemented in ingestible capsule 104 and the receive path of FIG. 26 may implemented in an external receiver patch, such as sensor link module 602.

Referring to FIG. 25, the transmission path includes a first differential encoder 2510, a second differential encoder 2520, a multiplier 2530, a carrier generator 2540, and an acoustic transducer/Tx 2516. First differential encoder 2510 includes a multiplier 2512 and a (one bit) delay element 2514. In this scheme, a current data bit $b_k$ in form of ±1 is multiplied by a result of a previous multiplication $e_{k-1}$ after it goes through delay element 2514. Thus, the encoded bit $e_k$ from first differential encoder 2510 can be written as $$e_k = e_{k-1} * b_k \quad \text{(Eq. 3)}$$

Second differential encoder 2520 includes a multiplier 2522 and a (one-bit) delay element 2524. The encoded bit $e_k$ from first differential encoder 2510 is multiplied by a result of a previous multiplication $f_{k-1}$ after it goes through delay element 2524. Thus, the encoded bit $f_k$ from second differential encoder 2520 can be written as $$f_k = f_{k-1} * e_k \quad \text{(Eq. 4)}$$

The encoded bit from second differential encoder 2520 is then provided to multiplier 2530.

Multiplier 2530 multiplies the encoded bit from second differential encoder 2520 with the signal from carrier generator 2540. The signal from multiplier 2530 is fed to acoustic transducer/Tx 2516.

Acoustic transducer/Tx 2516 converts the received signal into an acoustic signal that is transmitted through the multi-path acoustic channel.

After traveling through the multi-path acoustic channel, the acoustic signal is received by the receive path of FIG. 26. The receive path includes an acoustic transducer/Rx 2660, a double-differential autocorrelation decoder 2666, a synch 2670, and a decision module 2676. Acoustic transducer/Rx 2660 receives the acoustic signal and converts it into an electrical signal. Decoder 2666 directly calculates cos/sin trigonometric functions (I/Q components) of the first and second order phase differences for the received signal (modulated carrier) in a well-known manner. The received signal from the output of acoustic transducer/Rx 2660 is fed to decoder 2666 and to synch 2670. I/Q components from the output of decoder 2666 are fed to decision module 2676 for making a decision regarding the transmitted data symbol. Decoder 2666 and decision module 2676 are controlled by synch 2670.

It is to be appreciated that the acoustic transmission system illustrated in FIGS. 25 and 26 is presented for illustrative purposes only, and not limitation. For example, other embodiments may include an acoustic data transmission system with a quadrature DPSK modulation scheme ($D^1$QPSK and $D^2$QPSK). Such embodiments include a corresponding acoustic transmitter and receiver as would be apparent from the description contained herein. Additional embodiments may include a simple structure of a preamble signal, providing initial detection and synchronization for the data transmission session, as well as phase initialization for both $D^1PSK$ and $D^2PSK$ modes. Further embodiments use the trigonometric functions of the first and second order phase differences at the outputs of the autocorrelation demodulator for estimation of characteristics of current movement and location of ingestible capsule 104.

Thus, an embodiment of the present invention uses two types of DPSK encoding to provide an efficient solution for carrier phase uncertainty and carrier frequency instability in acoustic data transmission systems. These embodiments are substantially independent of carrier phase offset and of carrier frequency offset (substantially invariant to phase and frequency shifts in the acoustic channel). Also, these embodiments provide a high level of data transmission robustness (e.g., a high signal-to-noise ratio), associated with the PSK modulation technique.

(iv) Example Acoustic Data Transmission within Human Body

Figure 22:
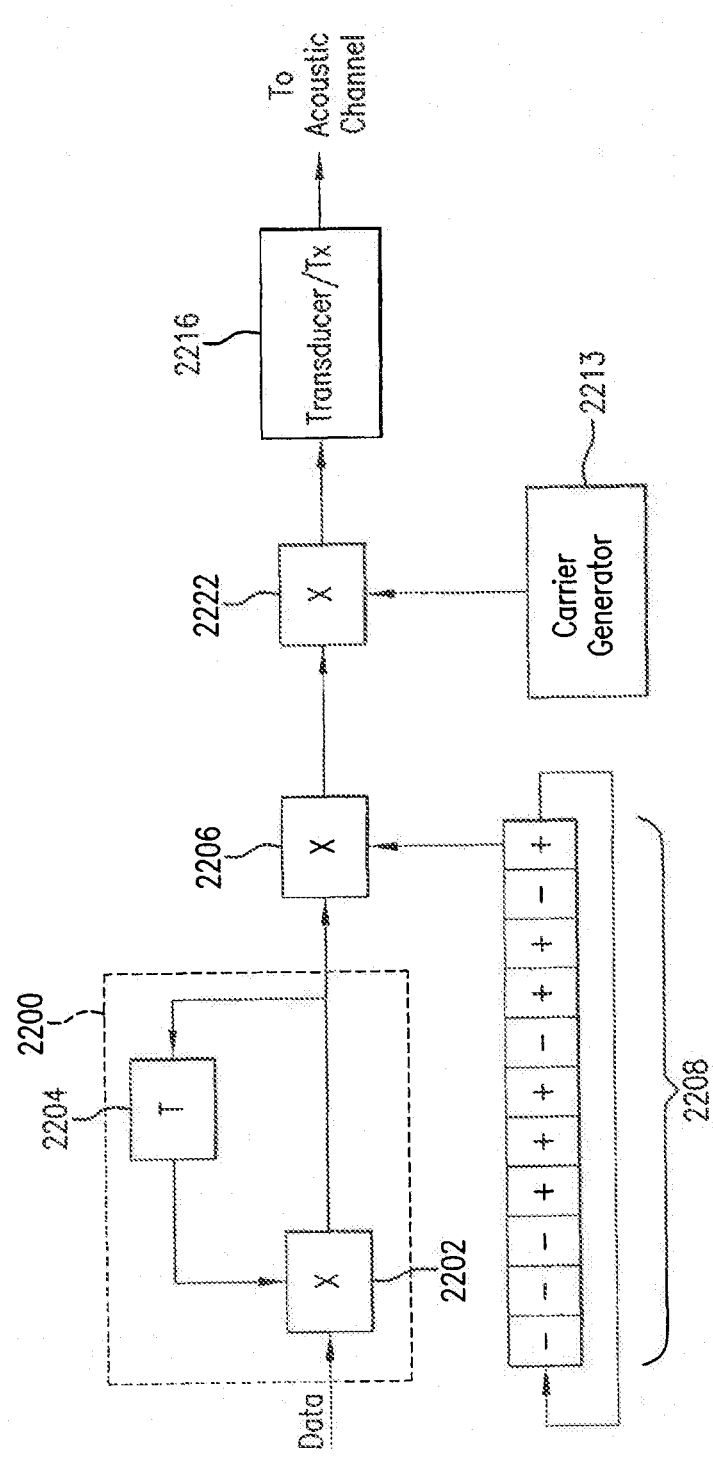
FIG. 22 illustrates a block diagram of a transmitter of an acoustic data transmission system that utilizes a DPSK modulation scheme and a Barker spreading code according to another embodiment of the present invention.
Figure 23:
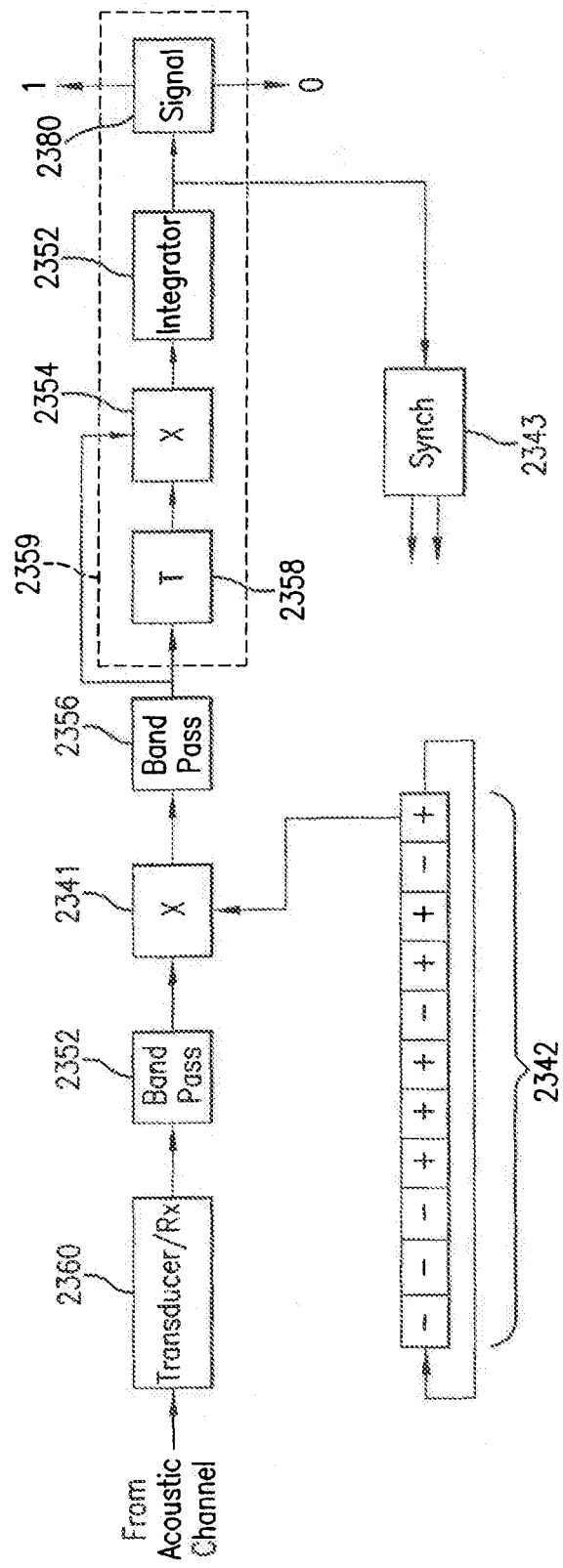
FIG. 23 illustrates a block diagram of a receiver of an acoustic data transmission system that utilizes a DPSK modulation scheme and a Barker spreading code according to another embodiment of the present invention.

FIGS. 22 and 23 depict block diagrams respectively illustrating a transmission path and a receive path of an acoustic data transmission system for acoustically transmitting data through a human's body according to an embodiment of the present invention. The transmission path of FIG. 22 may be implemented in ingestible capsule 104 and the receive path of FIG. 23 may be implemented in an external computing device, such as sensor link module 602. The acoustic transmission system illustrated in FIGS. 22 and 23 is based on a DBPSK modulation scheme in combination with an 11-element Barker code (11-Barker). For illustrative purposes, the acoustic transmission system of FIGS. 22 and 23 is described below in terms of data transmission having a bit rate of 10 kbit/s at 1 MHz carrier frequency through the acoustic channel with approximately 100 μs pulse response.

Referring to FIG. 22, the transmission path includes a DBPSK encoder 2200, a multiplier 2206, an 11-Barker register 2208, a carrier generator 2213, and an acoustic transducer/Tx 2216. The DBPSK encoder includes a multiplier 2202 and a (one-bit) delay element 2204. The DBPSK encoder functions in a similar manner to multiplier 2002 and delay element 2004 described above with reference to FIG. 20. For example, data bits in the form of ±1 with a bit rate of 10 kbit/s are fed to the input of the DBPSK encoder. The DBPSK includes multiplier 2202 and delay element 2204, which has a delay of approximately T=100 μs. Each current bit is multiplied by a result of the previous multiplication, as described above.

Barker register 2208 provides a Barker spreading code. The current ±1 signal (with duration 100 μs at the output of multiplier 2206) is transformed into a wideband sequence of positive and negative ones (each having a duration of approximately 100/11≈9.1 μs) by multiplication with the Barker sequence (generated by Barker register 2208). Barker register 2208 is an 11-bit cyclic shift register, containing ±1 binary digits as illustrated in FIG. 22. Barker register 2208 provides bit cyclic shifting with frequency 110 kHz, and therefore exactly 11 Barker elements are within the 100 μs data symbol interval. Barker register 2208 is synchronized with the data bit interval.

Carrier generator 2213 provides a 1 MHz carrier. The spreaded signal from the output of multiplier 2206, containing 11 positive and negative ones, modulates the 1 MHz carrier in multiplier 2222. The bit interval contains 100 cycles of the carrier, and Barker register 2208 contains about 9 carrier cycles.

The modulated carrier from multiplier 2222 is fed into acoustic transducer/Tx 2216. Acoustic transducer/Tx 2216 transmits an acoustic signal into the multi-path acoustic channel within human 102.

After traveling through the multi-path acoustic channel, the acoustic signal is received by the receive path of FIG. 23. The receive path includes an acoustic transducer/Rx 2360, an 11-Barker register 2342, a first band-pass filter 2352 and a second band-pass filter 2356, an autocorrelation DBPSK demodulator 2359, and a synch unit 2343.

Acoustic transducer/Rx 2360 receives the acoustic signal and transforms it into an electrical signal. The received signal from the output of transducer/Rx 2360 first passes through first band pass filter 2352. First band pass filter 2352 includes a wideband filter $BPF_1$ with a bandwidth of about 110 kHz around the 1 MHz carrier frequency.

The filtered signal is then multiplied, in multiplier 2341, by the Barker code from 11-Barker register 2342. 11-Barker register 2342 functions in a similar manner to Barker register 2208 (FIG. 22) described above.

The convoluted signal from the output of multiplier 2341 passes through second band pass filter 2356. Second band pass filter 2356 includes a narrowband filter $BPF_2$ with a bandwidth of about 10 kHz around the 1 MHz carrier frequency. The signal is then fed into the autocorrelation demodulator 2309.

Autocorrelation demodulator 2309 includes a delay element 2358, a multiplier 2354, an integrator 2352, and a sign detector (Sgn) 2380. Delay element 2358 has a time delay of approximately T=100 μs. It should be noted that delay element 2358 of FIG. 23 differs from delay element 2204 of FIG. 22. In the DBPSK encoder of FIG. 22, delay element 2204 functions as a bit memory; whereas, in the autocorrelation demodulator of FIG. 23, delay element 2358 functions as a delay line (samples memory).

In an embodiment, autocorrelation demodulator 2309 operates in the following manner. Multiplier 2354 multiplies the current input signal with the 100 μs delayed signal from delay element 2358. Integrator 2352 integrates (accumulates) the product during bit interval T=100 μs.

Sgn 2380 determines the received bit based on the sign of the integral. For example, a positive sign ("+") corresponds to a bit value of 1, and a negative sign ("−") corresponds to a bit value of 0.

Importantly, the above-described demodulation scheme does not require generation of the carrier and does not require any reference signal at all. Rather, the above-described demodulation scheme uses an initial synchronization of Barker register 2342 and the current symbol synchronization of both Barker register 2342 and integrator 2352 in the autocorrelation demodulator. At the ideal synchronization in the additive white Gaussian noise (AWGN) channel the demodulator provides a BER=$10^{-3}$ at SNR≈8.5 dB.

In an embodiment, a special preamble can be used for initial synchronization of Barker register 2342. The preamble, which contains at least two Barker sequences, is followed by a data package. During data package transmission, the symbol synchronization is carried out by synch unit 2343, using signals from the output of the demodulator.

(v) Improved Signal-to-Noise Ratio Based on Multi-Path Acoustic Signals

Figure 24:
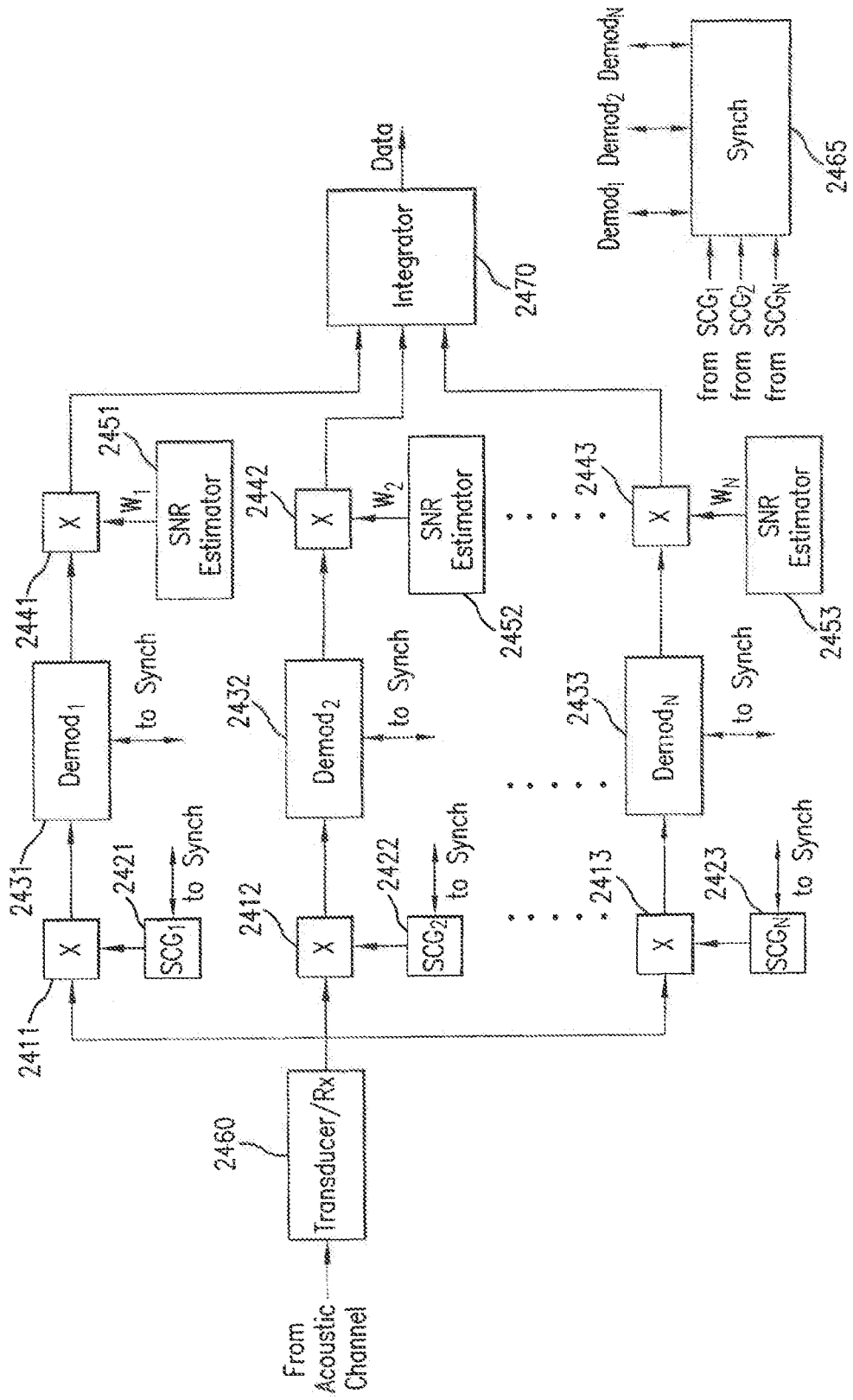
FIG. 24 illustrates a block diagram of a receiver of an acoustic data transmission system that extracts a signal from a plurality of reflected signals according to an embodiment of the present invention.

An embodiment of the present invention distinguishes different reflected acoustic rays to extract the ray with a high signal-to-noise ratio (SNR). This embodiment uses nearly all reflected acoustic rays by (i) initially distinguishing the acoustic rays having different time delays, (ii) accumulating signals of the acoustic rays in space divided receivers, and (iii) making a final decision based on a combined (integral) signal of the space divided receivers. The improved SNR can be achieved by a plurality of receive paths as illustrated in FIG. 24 which receive an acoustic signal after it travels through a multi-path acoustic channel. The acoustic signal can be transmitted through the multi-path acoustic channel using a transmitter similar to those described herein.

Referring to FIG. 24, the plurality of receive paths include an acoustic transducer/Rx 2460, a plurality of SCGs generating shifted versions of the spreading code, a corresponding plurality of demodulators, a plurality of SNR estimators, a plurality of weighted accumulators of the demodulator's outputs, a decision block (integrator) 2470, and a synch unit 2465. As illustrated in FIG. 24, the plurality of SCGs include a $SCG_1$ 2421, a $SCG_2$ 2422, and a $SCG_N$ 2423; the plurality of demodulators include a $demodulator_1$ 2431, a $demodulator_2$ 2432, and a $demodulator_N$ 2433; the plurality of SNR estimators include a SNR estimator 2451, a SNR estimator 2452 and a SNR estimator 2453. Each receive path of FIG. 24 includes a SCG, a demodulator, and SNR estimator. For simplicity of exposition, the operation of $SCG_1$ 2421, demodulator, 2431, and SNR estimator 2451 is described below. The operation of the other SCGs, demodulators, and SNR estimators will be apparent from this description.

Acoustic transducer/Rx 2460 receives the acoustic signal after it travels through the multi-path acoustic channel. Multiplier 2411 multiplies the received signal from the output of acoustic transducer/Rx 2460 by the shifted signals from the output of $SCG_1$ 2421, and provides the result to $demodulator_1$ 2431.

SNR estimator 2451 estimates the SNR of the received acoustic signal. Multiplier 2441 multiplies the soft decisions from the output of $demodulator_1$ 2431 by the weight coefficient $w_1$ provided by SNR estimator 2451, and provides the result to integrator 2470.

Integrator 2470 combines the final signal from each receive path for making a hard decision regarding the transmitted data symbol. The SCGs and the demodulators are controlled by synch unit 2465 in a similar manner to that described above.

The plurality of receive paths of FIG. 24 combine a plurality of reflected rays in the multi-path acoustic channel to provide an output signal having a high SNR, thereby providing improved performance.

Another embodiment combines the received data signal from each of a plurality of receivers (e.g. sensor link modules 602) having space diversity. The plurality of spatially diverse receivers can be used in different manners. According to a first approach, the final (integral) signal from each spatially diverse receiver (as described above with reference to FIG. 24) is combined (with corresponding weighted coefficients) into a super-signal, which serves as a basis for hard decision making. This approach provides a very high performance gain. A second approach provides signal processing in each spatially diverse receiver with only (individual) shift of the spreading code, and after that the outputs of the spatially diverse receivers are combined (with corresponding weighted coefficients) into a final (integral) signal for hard decision making. According to a third approach, the individual receivers find out in turn (in order of priority) the biggest next reflection and use a combination of the found reflections for making the final hard decision.

It is important to note that the exemplary frequency band of operation around 1 MHz is presented for illustrative purposes only, and not limitation. Persons skilled in the relevant art(s) will appreciate that a higher data rate, for example 2 times illustrated above, can be realized based on the teachings above, translated into, for example, a 2 MHz frequency band of operation. Such deviations from the teachings above are contemplated within the spirit and scope of this invention.

Furthermore, higher data rates may be achieved in accordance with an embodiment of the present invention by operating multiple parallel data paths or a single data path split into multiple data paths, wherein each is or many data paths are implemented through the methods described and exemplified above and operational on discrete and disjoint frequency bands. For example, from teachings and examples above, and with reference to FIG. 9, transducer 904A may be operational at 1 MHz, with a bandwidth of 100 kHz, and a data rate of 10 kbps. Additionally, transducer 904B may operate at 1.2 MHz, with 100 kHz of bandwidth and 10 kbps data rate. Device 104, if operating transducers 904A and 904B concurrently, can achieve a data rate of 20 kbps to an external set of receivers. A person skilled in the relevant art(s) will appreciate how to design a system with a plurality of transmitters and receivers in parallel operation to achieve a targeted data bit rate without depart from the spirit and scope of this present invention. For example, a plurality of orthogonal spreading codes may be used in combination with a single acoustic transducer to transmit through a corresponding plurality of acoustic channels, thereby increasing the data rate of transmission.

C. Frequency Hopping i. Overview

Figure 27:
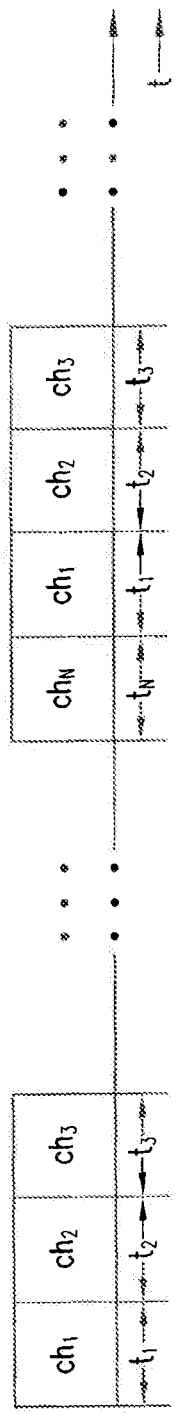
FIG. 27 illustrates a frequency hopping (FH) scheme to encode and/or decode an acoustic communication signal according to an exemplary embodiment of the present invention.

FIG. 27 illustrates a frequency hopping (FH) scheme to encode and/or decode an acoustic communication signal according to an exemplary embodiment of the present invention. An acoustic communication signal 2700, such as communication signal 106, may be transmitted from a transmitter, such as ingestible capsule 104, to a receiver, such as external computing device 108 or one or more sensor link modules 602 attached to the skin of the body, using the FH scheme. The FH scheme encodes and/or decodes communication signals by switching a carrier frequency among one or more frequency channels. The carrier frequency used to encode and/or decode the acoustic communication signal is changed or hopped over a range of frequencies according to a chosen code known as a hopping pattern.

As shown in FIG. 27, an acoustic communication signal 2700 may be partitioned into one or more time intervals denoted as $t_1$ through $t_N$. Time intervals $t_1$ through $t_N$ may represent the duration of a bit, a byte, a symbol, a session, or any other suitable time interval that will be apparent to those skilled in the relevant art. Each time interval $t_1$ through $t_N$ includes a corresponding frequency channel denoted as $ch_1$ through $ch_N$. In an exemplary embodiment, an initialization frequency channel, such as frequency channel $ch_1$, is reserved as a data sequence initiation signal or a synchronization signal between the transmitter and the receiver. After transmission of the acoustic communication signal, the transmitter transmits the initialization frequency channel to allow for transmission of a next acoustic communication signal. Upon detection of the initialization frequency channel, the receiver switches a corresponding carrier frequency to a carrier frequency associated with the initial frequency channel to begin decoding of the next acoustic communication signal.

The FH scheme selects or switches among frequency channels $ch_1$ through $ch_N$ based upon time intervals $t_1$ through $t_N$ to encode and/or decode acoustic communication signal 2700. For example, frequency channel $ch_1$ is selected for time interval $t_1$. After time interval $t_1$ lapses or expires, frequency channel $ch_2$ is selected for time interval $t_2$. The transition between a first frequency channel, such as frequency channel $ch_1$ and a second frequency channel, such as frequency channel $ch_2$, may be substantially instantaneous, as shown in FIG. 27, or delayed. Likewise, as time interval $t_2$ expires, frequency channel $ch_3$ is selected for time interval $t_3$. Each of remaining frequency channels $ch_4$ through $ch_N$ is selected for a corresponding time interval $t_4$ through $t_N$ in a similar manner. Upon expiration of time interval $t_N$, frequency channel $ch_1$ is selected once again to continue switching among frequency channels $ch_1$ through $ch_N$ based upon time intervals $t_1$ through $t_N$.

In an exemplary embodiment, a maximum duration of time intervals $t_1$ through $t_N$ is such that the information content embedded with a corresponding frequency channel is transmitted and/or received before the acoustic multipath phenomena generates a second considerable residual ray, described previously as the clear channel, for that particular frequency in a target environment, such as human 102. The second considerable ray represents the first reflection of the transmitted communication signal generated by the multipath phenomena, and starts the time period of a transitionary channel. In this exemplary embodiment, the duration (T) for each time interval $t_1$ through $t_N$ may be given by:

$$T = \frac{T_{RAY}}{\text{NUM\_CH}}, \quad \text{(Eq. 5)}$$

where $T_{RAY}$ represents a truncated ray delay and NUM_CH represents the number of frequency channels in frequency channels $ch_1$ through $ch_N$. The truncated ray delay represents an amount of time necessary for all rays generated by the multipath phenomena for a corresponding frequency to be attenuated to a negligible level, such as, but not limited to, fifteen decibels (dB) to provide an example. In an exemplary embodiment suitable for use in human 102 and at a particular ultrasonic frequency range, the truncated ray delay may be, for example, approximately equal to from 100 to 200 microseconds. However, this example is not limiting, and other maximum durations for time intervals $t_1$ through $t_N$ that are apparent to those skilled in the relevant art are within the scope and spirit of the present invention.

From the discussion above, the multipath phenomena may cause acoustic communication signal 2700 to reach the receiver by one or more paths. Switching from a frequency channel, such as frequency channel $ch_1$, to another frequency channel, such as frequency channel $ch_2$, before generation of the second considerable ray mitigates the effects of the multipath phenomena. In addition, cyclic repetition of frequency channels $ch_1$ through $ch_N$ after at least T*NUM_CH seconds, allows the transmitter and/or the receiver to reuse frequency channels $ch_1$ through $ch_N$ after all considerable rays from a corresponding frequency channel $ch_1$ through $ch_N$ have become negligible, returning the frequency of interest to a clear channel status. For example, the transmitter may once again select the corresponding carrier frequency associated with frequency channel $ch_1$ after at least T*NUM_CH seconds has elapsed to allow the second considerable residual ray and all other considerable rays to attenuate to a negligible level.

Figure 28:
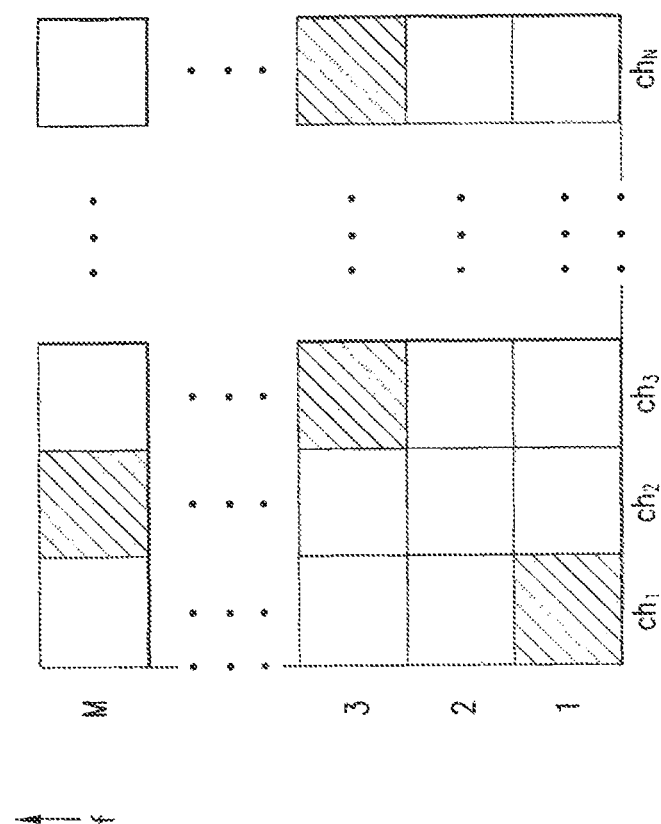
FIG. 28 illustrates a hopping pattern used to encode and/or decode the acoustic communication signal according to an exemplary embodiment of the present invention.

FIG. 28 illustrates a hopping pattern used to encode and/or decode the acoustic communication signal according to an exemplary embodiment of the present invention. The hopping pattern may be represented by a time-frequency matrix. The time-frequency matrix is a graphical representation of carrier frequencies, denoted as $f_1$ through $f_M$, that may be assigned to a corresponding frequency channel $ch_1$ through $ch_N$. Each frequency channel in frequency channel $ch_1$ through $ch_N$ need not contain a corresponding carrier frequency. For example, carrier frequency $f_1$ may be assigned to frequency channel $ch_1$. In other words, carrier frequency $f_1$ is used for the encoding and/or decoding of the acoustic communication signal during the time interval $t_1$ corresponding to frequency channel $ch_1$. Likewise, carrier frequency $f_M$ may be assigned to frequency channel $ch_2$. Similarly, carrier frequency $f_3$ may be assigned to frequency channel $ch_3$. Finally, carrier frequency $f_3$ may be assigned to frequency channel $ch_N$. However, this example is not limiting, those skilled in the arts will recognize that frequency channels $ch_1$ through $ch_N$ may assigned to any other suitable sequence of carrier frequencies $f_1$ through $f_M$ without departing from the spirit and scope of the invention. For example, any suitable random or pseudo-random sequence may be used to assign carrier frequencies $f_1$ through $f_M$ to the corresponding frequency channel $ch_1$ through $ch_N$. As another example, carrier frequencies $f_1$ through $f_M$ may be assigned to the corresponding frequency channel $ch_1$ through $ch_N$ in a sequential manner with a carrier frequency having a least frequency being assigned to frequency channel $ch_1$ and a carrier frequency having a greatest frequency being assigned to frequency channel $ch_N$. In a further example, an identification of the transmitter and/or the receiver, such as but not limited to an electronic identification, may be used to assign carrier frequencies $f_1$ through $f_M$ to the corresponding frequency channel $ch_1$ through $ch_N$. In this example, the identification of the transmitter and/or the receiver is unique for each transmitter and/or receiver thereby encrypting the acoustic communication signal based on the hopping pattern. A further example is having no frequency used more than once in channels $ch_1$ through $ch_N$ to ensure that each frequency has a clear channel. Furthermore, in an embodiment using encrypted information, a transmitter may send a signal on a frequency that is not part of the matrix. This additional information intentionally obscures the real information.

ii. Combination of Frequency Hopping and Pulse Interval Encoding

FIG. 29A illustrates a combined FH and pulse interval encoding (PIE) scheme to encode and/or decode an acoustic communication signal according to an exemplary embodiment of the present invention. An acoustic communication signal 2900 may represent an exemplary embodiment of communication signal 106. From the discussion of FIG. 27 above, a transmitter, such as communications module 204, transmits acoustic communication signal 2900 by encoding an information signal, such as sensor output signal 212, onto frequency channels $ch_1$ through $ch_N$ corresponding to time intervals $t_1$ through $t_N$. The transmitter delays the transmission of adjacent frequency channels, such as frequency channel $ch_1$ and frequency channel $ch_2$, by a corresponding time delay $T_1$ through $T_N$ to encode the information signal.

As shown in FIG. 29A, the transmitter transmits a first frequency channel, such as frequency channel $ch_1$, for a first interval of time, such as time interval $t_1$. The transmitter then waits or ceases to transmit for a corresponding time delay, such as time delay $T_1$, to begin the transmission of a second frequency channel, such as frequency channel $ch_2$. The transmitter encodes the information signal by varying a length of the corresponding time delay $T_1$. More specifically, the transmitter encodes the information signal by delaying the transmission of the second frequency channel a number of delay intervals $i_1$ through $i_k$. The number of delay intervals $i_1$ through $i_k$ included within a corresponding time delay $T_1$ through $T_N$ represents a logic value. The logic value may be one or more bits, one or more bytes, one or more symbols, or any other suitable data length or combination of data lengths. An individual delay interval in delay intervals $i_1$ through $i_k$ may be a duration of one or more bits, one or more bytes, one or more symbols, or any other suitable data length or combination of data lengths. An advantage of encoding using the scheme of FIG. 29A is that all actual transmit time $i_1$ can be as minimal as possible while the data encoding may extend a period of no transmission $T_1$. The average duty cycle of the transmitter emission may then fall substantially below 50%, which is a typical goal in most low power transmission systems. Since reasonable power is consumed when the transmitter is emitting, this encoding scheme is ultimately extremely power efficient from the standpoint of the transmitter.

As shown in FIG. 29B, delaying a transmission of a second frequency channel $ch_B$ after a transmission of a first frequency channel $ch_A$ by delay interval $i_1$ may represent a first logic value, such as a binary zero-zero. A second logic value, such as a binary one-zero, may be represented by delaying the transmission of second frequency channel $ch_B$ after the transmission of first frequency channel $ch_A$ by a combined duration of delay interval $i_1$ through delay interval $i_2$. A third logic value, such as a binary one-one, may be represented by delaying the transmission of second frequency channel $ch_B$ after the transmission of first frequency channel $ch_A$ by a combined duration of delay interval $i_1$ through delay interval $i_3$. A fourth logic value, such as a binary zero-one, may be represented by delaying the transmission of second frequency channel $ch_B$ after the transmission of first frequency channel $ch_A$ by a combined duration of delay interval $i_1$ through delay interval $i_4$. However, this example is not limiting, those skilled in the arts will recognize that any logic value may be represented by delaying the transmission of second frequency channel $ch_B$ any number of delay intervals $i_1$ through $i_k$ without departing from the spirit and scope of the invention. For example, N logic values may be represented by delaying the transmission of second frequency channel $ch_B$ any suitable number of delay intervals $i_1$ through $i_N$ and/or combinations thereof.

In a particular embodiment, relevant to a low power and reasonably compact sensor device 104, a timing basis may be derived from a simple and non-accurate on-board clock. Simple, low power clocks tend to drift from a target frequency for a variety of reasons and conditions understandable to one of skill in the art. The drift is more severe the longer the time period from synchronization. An effective and efficient design for the embodiment of FIG. 29B in this case may maintain a minimal time period $i_1$, while increasing the time periods $i_2$, $i_3$, and so on to compensate for anticipated maximal drift.

A receiver, such as external computing device 108 or one or more sensor link modules 602 attached to the skin of the body, decodes acoustic communication signal 2900 to recover the information signal. In particular, the receiver detects first frequency channel $ch_A$ then measures a length of the corresponding time delay $T_1$ through $T_N$ until detection of second frequency channel $ch_B$. The receiver assigns a recovered logic value based upon the length of the corresponding time delay $T_1$ through $T_N$. More specifically, the receiver measures the number of delay intervals $i_1$ through $i_k$ to determine the length of the corresponding time delay $T_1$ through $T_N$, then assigns the logic value to a recovered information signal to recover the information signal based upon the length of the corresponding time delay $T_1$ through $T_N$.

To decode acoustic communication signal 2900 encoded according to FIG. 29B, the receiver assigns the first logic value to the recovered information signal when a time delay between first frequency channel $ch_A$ and second frequency channel $ch_B$ is measured as delay interval $i_1$. Likewise, if the receiver measures the time delay between first frequency channel $ch_A$ and second frequency channel $ch_B$ as the combined duration of delay interval $i_1$ through delay interval $i_2$, the receiver assigns the second logic value to the recovered information signal. Similarly, if the receiver measures the time delay between first frequency channel $ch_A$ and second frequency channel $ch_B$ as the combined duration of delay interval $i_1$ through delay interval $i_3$, the receiver assigns the third logic value to the recovered information signal. Finally, if the receiver measures the time delay between first frequency channel $ch_A$ and second frequency channel $ch_B$ as the combined duration of delay interval $i_1$ through delay interval $i_4$, the receiver assigns the fourth logic value to the recovered information signal. However, this example is not limiting, those skilled in the arts will recognize that any logic value may be assigned to the recovered information signal based upon any suitable combination of delay intervals $i_1$ through $i_K$ without departing from the spirit and scope of the invention. For example, N logic values may be assigned to the recovered information signal using any suitable number of delay intervals $i_1$ through $i_K$ and/or combinations thereof.

Iii. Combination of Frequency Hopping and Differential Phase Shift Keying

FIG. 30A illustrates a combined FH and differential phase shift keying (DPSK) scheme to encode and/or decode an acoustic communication signal according to an exemplary embodiment of the present invention. From the discussion of FIG. 27 above, a transmitter, such as communications module 204, transmits an acoustic communication signal 3000, such as communication signal 106, by encoding an information signal, such as sensor output signal 212, onto frequency channels $ch_1$ through $ch_N$ corresponding to time intervals $t_1$ through $t_N$. The transmitter embeds one or more phases, denoted as $\phi_1$, through $\phi_i$, of a corresponding carrier frequency, such as carrier frequencies $f_1$ through $f_M$ as discussed in FIG. 28, onto each frequency channel in frequency channels $ch_1$ through $ch_N$ to encode the information signal. In other words, transitions among one or more phases $\phi_1$ through $\phi_i$ within a corresponding frequency channel in frequency channels $ch_1$ through $ch_N$ are used to encode the information signal.

Phases $\phi_1$ through $\phi_i$ are relative to the preceding phase. Such systems, as would be expected in very low power devices such as with sensor device 104, do not have extremely stable oscillators and may drift, have phase distortions, etc. Therefore, a phase reference to an initial phase, running for many bit periods and phase changes is very difficult to build. An encoding scheme that is simpler to implement in a low power scenario involving a phase change from a first time period $t_1$ to a second time period $t_2$, another phase change from a time period $t_2$ to a third time period $t_3$, and so on as is referred to herein as a differential phase change. FIG. 30B depicts two cycles of frequencies. Depending upon design goals and available bandwidths for operation, more or fewer cycles may be used as necessary as would be understood by a person skilled in the art. Thus, use of any number of cycles of frequencies in between phase changes does not depart from the spirit and scope of this invention.

As shown in FIG. 30A, the transmitter transmits a carrier frequency having the one or more phases $\phi_1$ through $\phi_i$, such as one of carrier frequencies $f_1$ through $f_M$ as shown in FIG. 28, associated with a first frequency channel, such as frequency channel $ch_1$, for a first interval of time, such as time interval $t_1$. The transmitter encodes the information signal by transmitting the one or more phases $\phi_1$ through $\phi_i$ of the carrier frequency throughout the first interval of time. After the first interval of time lapses or expires, the transmitter cycles through frequency channels $ch_1$ through $ch_N$ as discussed in FIG. 27 and transmits the one or more phases $\phi_1$ through $\phi_i$ of the carrier frequency associated with frequency channels $ch_1$ through $ch_N$, as discussed in FIG. 28 to encode the information signal.

As shown in FIG. 30B, the transmitter transmits a first phase $\phi_1$ of a carrier frequency, such as carrier frequencies $f_1$ through $f_M$, associated with frequency channels $ch_1$ through $ch_N$, for a time interval $t_A$, a time interval $t_B$, and a time interval $t_C$ to represent a first logic value, such as a binary zero-zero. A combination of time interval $t_A$, time interval $t_B$, and time interval $t_C$ is substantially less than or equal to one or more of time intervals $t_1$ through $t_N$. A second logic value, such as a binary zero-one, may be represented by transmitting the first phase $\phi_1$ of the carrier frequency for time interval $t_A$ and time interval $t_B$ followed by transmitting a second phase $\phi_2$ of the carrier frequency for time interval $t_C$. A third logic value, such as a binary one-one, may be represented by transmitting the first phase $\phi_1$ of the carrier frequency for time interval $t_A$, the second phase $\phi_2$ of the carrier frequency for time interval $t_B$, followed by the first phase $\phi_1$ of the carrier frequency for time interval $t_C$. A fourth logic value, such as a binary one-zero, may be represented by transmitting the first phase $\phi_1$ of the carrier frequency for time interval $t_A$, the second phase $\phi_2$ of the carrier frequency for time interval $t_B$ and time interval $t_C$. However, this example is not limiting, those skilled in the art will recognize that the transmitter may encode the information signal to represent any suitable number of logic values by transmitting at least one of the one or more phases $\phi_1$ through $\phi_i$ of the carrier frequency throughout time intervals $t_1$ through $t_N$. For example, the transmitter may encode the information signal using a carrier frequency having four phase differences to generate a combined FH and differential quadrature phase shift keyed (DQPSK) acoustic communication signal, a carrier frequency having eight phase differences to generate a combined FH and differential 8-phase shift keyed (D8PSK) acoustic communication signal, and/or a carrier frequency having N phase differences to generate a combined FH and differential N-phase shift keyed (DNPSK) acoustic communication signal.

A receiver, such as external computing device 108 or one or more sensor link modules 602 attached to the skin of the body, decodes acoustic communication signal 3000 to recover the information signal. In particular, the receiver detects the one or more phases $\phi_1$ through $\phi_i$ of the carrier frequency throughout time intervals $t_1$ through $t_N$. The receiver assigns a recovered logic value based upon a number of transitions among the one or more phases $\phi_1$ through $\phi_i$ of the carrier frequency.

To decode acoustic communication signal 3000 encoded according to FIG. 30B, the receiver assigns the first logic value to the recovered information signal upon detecting the first phase $\phi_1$ of the carrier frequency for time interval $t_A$, time interval $t_B$, and time interval $t_C$. Likewise, if the receiver detects the first phase $\phi_1$ of the carrier frequency for time interval $t_A$ and time interval $t_B$ followed by the second phase $\phi_2$ of the carrier frequency for time interval $t_C$, the receiver assigns the second logic value to the recovered information signal. Similarly, if the receiver detects the first phase $\phi_1$ of the carrier frequency for time interval $t_A$, the second phase $\phi_2$ of the carrier frequency for time interval $t_B$ followed by the first phase $\phi_1$ of the carrier frequency for time interval $t_C$, the receiver assigns the third logic value to the recovered information signal. Finally, if the receiver detects the first phase $\phi_1$ of the carrier frequency for time interval $t_A$ followed by the second phase $\phi_2$ of the carrier frequency for time interval $t_B$ and time interval $t_C$, the receiver assigns the fourth logic value to the recovered information signal. However, this example is not limiting, those skilled in the art will recognize that the receiver may decode the acoustic communication signal by assigning any suitable number of logic values by detecting at least one of the one or more phases $\phi_1$ through $\phi_i$ of the carrier frequency throughout time intervals $t_1$ through $t_N$.

FIG. 31 illustrates a block diagram of a transmitter to encode an information signal using a combined FH and DPSK scheme according to an exemplary embodiment of the present invention. A transmitter 3110 may be used to generate acoustic communication signal 3000 as shown in FIG. 30A. Transmitter 3110 may represent an exemplary embodiment of communications module 204. As will be understood by persons skilled in the relevant art from the teachings provided herein, transmitter 3110 may be readily implemented in hardware, software, or a combination of hardware and software. For example, based on the teachings provided herein, a person skilled in the relevant art could implement transmitter 3110 via a combination of one or more application specific integrated circuits and a processor core for implementing software commands stored in one or more attached memories. However, this example is not limiting, and other implementations are within the scope and spirit of the present invention.

As shown in FIG. 31, transmitter 3110 may include an acoustic communications module 3112 and a radiating element 3114. Acoustic communications module 3112 includes an encoder 3100, a function generator 3102, a mixer 3104, and a carrier generator 3106. Acoustic communications module 3112 may represent an exemplary embodiment of acoustic communications module 302. Encoder 3100 receives an information signal 3150. Information signal 3150 may include, but is not limited to, sensor output signal 212. Encoder 3100 encodes information signal 3150 to generate a reference pulse 3154. In an exemplary embodiment, encoder 3100 partitions information signal 3150 into one or more bits, one or more bytes, one or more symbols, or any other suitable manner that will be apparent to those skilled in the relevant art.

Function generator 3102 operates on reference pulse 3154 to produce an encoded baseband communication signal 3156. More specifically, function generator 3102 operates upon reference pulse 3154 using one or more mathematical functions, such as a Walsh function or any other suitable mathematical function that will be apparent to those skilled in the relevant art. For example, for a one bit transmission, function generator 3102 may store a first Walsh function $S_1$ and a second Walsh function $S_2$. First Walsh function $S_1$ may be represented as:

$$[S_0 \text{-} S_0], \qquad \text{(Eq. 6)}$$

where $S_0$ is a reference pulse with any carrier frequency, such as carrier frequencies $f_1$ through $f_M$. In an exemplary embodiment, reference pulse 3154 represents reference pulse $S_0$. Likewise, second Walsh function $S_2$ may be represented as:

$$[S_0 \text{-} S_0]. \qquad \text{(Eq. 7)}$$

Function generator 3102 may output first Walsh function $S_1$ or second Walsh function $S_2$ based upon reference pulse 3154. However, this example is not limiting, those skilled in the art will recognize that function generator 3102 may operate upon reference pulse 3154 using one or more mathematical functions without departing from the spirit and scope of the invention. For example, a set of Walsh functions for a two bit transmission may be denoted as $S_1=[S_0\ S_0\ S_0\ S_0]$, $S_2=[S_0\ S_0\ \text{-}S_0\ \text{-}S_0]$, $S_3=[S_0\ \text{-}S_0\ \text{-}S_0\ S_0]$, and $S_4=[S_0\ \text{-}S_0\ S_0\ \text{-}S_0]$. Likewise, a set of Walsh functions for a three bit transmission may be denoted as $S_1=[S_0\ S_0\ S_0\ S_0\ S_0\ S_0\ S_0\ S_0]$, $S_2=[S_0\ S_0\ S_0\ \text{-}S_0\ \text{-}S_0\ \text{-}S_0\ \text{-}S_0]$, $S_3=[S_0\ S_0\ \text{-}S_0\ \text{-}S_0\ \text{-}S_0\ \text{-}S_0\ S_0\ S_0]$, $S_4=[S_0\ S_0\ \text{-}S_0\ \text{-}S_0\ S_0\ S_0\ \text{-}S_0\ \text{-}S_0]$, $S_5=[S_0\ \text{-}S_0\ \text{-}S_0\ S_0\ S_0\ \text{-}S_0\ \text{-}S_0\ S_0]$, $S_6=[S_0 -S_0 -S_0 S_0 -S_0 S_0 S_0 -S_0]$, $S_7=[S_0 -S_0 S_0 -S_0 -S_0 S_0 -S_0 S_0]$, and $S_8=[S_0 -S_0 S_0 -S_0 S_0 -S_0 S_0 -S_0]$.

Carrier generator 3106 generates a carrier frequency 3160 according to the FH scheme as discussed in conjunction with FIG. 27 and FIG. 28. For example, carrier generator 3106 generates carrier frequency 3160 corresponding to carrier frequencies $f_1$ through $f_M$ assigned to frequency channels $ch_1$ through $ch_N$.

Multiplier 3104 generates an electrical communication signal 3158 by multiplying encoded baseband communication signal 3156 and carrier frequency 3160. More specifically, multiplier 3104 upconverts encoded baseband communication signal 3156 using carrier frequency 3160 to generate electrical communication signal 3158.

Radiating element 3114 converts electrical communication signal 3158 to an acoustic representation to generate an acoustic communication signal 3152. Acoustic communication signal 3152 is an exemplary embodiment of, but is not limited to, communication signal 106. Radiating element 3114 may represent an exemplary embodiment of radiating element 304. Radiating element 3114 may be, but is not limited to, an electromechanical transducer or piezoelectric (e.g., PZT, PVDF, etc.) element or transducer that vibrates at acoustic frequencies.

FIG. 32 illustrates a block diagram of a receiver to decode an acoustic communication signal using a combined FH and DPSK scheme according to an exemplary embodiment of the present invention. A receiver 3200, such as external computing device 108 or one or more sensor link modules 602 attached to the skin of the body, decodes an acoustic communication signal 3250 to recover a recovered information signal 3252. As shown in FIG. 32, receiver 3200 may include a radiating element 3202, a bandpass filter array 3204, a demodulator 3206, a function generator 3208, and a carrier generator 3210.

Radiating element 3202 receives acoustic communication signal 3250, such as acoustic communication signal 3000 to provide an example. Radiating element 3202 converts acoustic communication signal 3250 to an electrical signal to generate an electrical communication signal 3254. Radiating element 3202 may be, but is not limited to, an electromechanical transducer or piezoelectric (e.g., PZT, PVDF, etc.) element or transducer that vibrates at acoustic frequencies.

Bandpass filter array 3204 receives electrical communication signal 3254 to generate a filtered communication signal 3256. Bandpass filter array 3204 may include a selectable arrangement of one or more bandpass filters. Each bandpass filter in bandpass filter array 3204 may be implemented as, but not limited to, a Bessel filter, a Butterworth filter, a Chebyshev filter, a Comb filter, an Elliptic filter, or any other suitable filter topology to provide some examples. At least one or more of the bandpass filters corresponds to one or more of frequency channels $ch_1$ through $ch_N$. In an exemplary embodiment, bandpass filter array 3204 includes one bandpass filter for each of frequency channels $ch_1$ through $ch_N$. For example, a bandpass filter array 3204 having five bandpass filters may filter an electrical representation of acoustic communication signal 3250, namely electrical communication signal 3254, that is DPSK encoded over five frequency channels $ch_1$ through $ch_5$.

Demodulator 3206 uses a carrier frequency 3260 to demodulate and/or downconvert filtered communication signal 3256 to produce a demodulated communication signal 3258. In an exemplary embodiment, demodulator 3206 demodulates filtered communication signal 3256 to a baseband frequency. Demodulator 3206 may be implemented as an optimal non-coherent demodulator, a suboptimal non-coherent demodulator, such as a delay-and-multiply receiver, or any other suitable demodulator capable of demodulating a DPSK, a DQPSK, a D8PSK, and/or a DNPSK encoded communication signal.

Carrier generator 3210 generates carrier frequency 3260 according to the FH scheme as discussed in conjunction with FIG. 27 and FIG. 28. For example, carrier generator 3208 generates carrier frequency 3260 corresponding to carrier frequencies $f_1$ through $f_M$ assigned to frequency channels $ch_1$ through $ch_N$.

Function generator 3208 receives demodulated communication signal 3258 to generate recovered information signal 3252, such as communication signal 506 in FIG. 5. Function generator 3208 generates recovered information signal 3252 by decoding demodulated communication signal 3258 using one or more mathematical functions, such as a Walsh function or any other suitable mathematical function to provide some examples. For example, for a one bit transmission, function generator 3208 may operate upon demodulated communication signal 3258 using first Walsh function $S_1$ and assign a first logic value to recovered information signal 3252 corresponding to first Walsh function $S_1$. Similarly, function generator 3208 may operate upon demodulated communication signal 3258 using second Walsh function $S_2$ and assign a second logic value to recovered information signal 3252 corresponding to second Walsh function $S_2$. Those skilled in the art will recognize that function generator 3208 may assign recovered information signal 3252 any suitable number and/or type of logic values using one or more suitable mathematical functions. For example, function generator 3208 may assign recovered information signal 3252 a first logic value, a second logic value, a third logic value and/or a fourth logic value corresponding to first Walsh function $S_1$, second Walsh function $S_2$, third Walsh function $S_3$, and/or fourth Walsh function $S_4$ for a two bit transmission.

In an exemplary embodiment, receiver 3200 may simultaneously demodulate one or more acoustic communication signals 3250. Receiver 3200 may simultaneously receive one or more acoustic communication signals 3250 produced by one or more transmitters synchronously transmitting on a substantially identical frequency band using orthogonal sets of mathematical functions. For example, a first transmitter may use a first mathematical function, such as a first Walsh function $S_1$ of $[S_0\ S_0\ S_0\ S_0]$ and a second Walsh function $S_2=[S_0\ S_0\ -S_0\ -S_0]$ for its bit transmission while a second transmitter may use a second mathematical function, such as a first Walsh function $S_1$ of $[S_0\ -S_0\ -S_0\ S_0]$ and a second Walsh function $S_2=[S_0\ -S_0\ S_0\ -S_0]$ for its bit transmission.

iv. Combination of Frequency Hopping and Frequency Shift Keying

From the discussion of FIG. 27 above, a transmitter, such as communications module 204, may transmit an acoustic communication signal, such as communication signal 106, by encoding an information signal, such as sensor output signal 212, onto frequency channels $ch_1$ through $ch_N$ corresponding to time intervals $t_1$ through $t_N$. The transmitter embeds one or more carrier frequencies, such as carrier frequencies $f_1$ through $f_M$, onto each frequency channel in frequency channels $ch_1$ through $ch_N$ to encode the information signal.

FIG. 33A illustrates a hopping pattern used to encode and/or decode an acoustic communication signal using a combination of FH and differential frequency shift keying (DFSK) according to an exemplary embodiment of the present invention. Carrier frequencies $f_1$ through $f_M$ as discussed in FIG. 28, may be partitioned or divided into one or more sets of carrier frequencies. The one or more sets of carrier frequencies may include one or more bands, registers, octaves, or any other suitable division of carrier frequencies $f_1$ through $f_M$ that will be apparent to those skilled in the art. For example, as shown in FIG. 33A, frequency channels $ch_1$ through $ch_N$ correspond to a first set of carrier frequencies f including carrier frequencies $f_1$ through $f_{M/2}$ and a second set of carrier frequencies F including carrier frequencies $f_{M/2+1}$ through $f_{M/2}$. However, this example is not limiting, those skilled in the arts will recognize that carrier frequencies $f_1$ through $f_M$ may be divided into one or more sets of carrier frequencies without departing from the spirit and scope of the invention. Those skilled in the arts will also recognize that the sets of carrier frequencies, such as first set of carrier frequencies f and second set of carrier frequencies F, may contain a similar and/or a dissimilar number of carrier frequencies and consecutive and/or non-consecutive frequencies without departing from the spirit and scope of the invention.

Referring back to FIG. 33A, the transmitter and/or the receiver may assign one or more carrier frequencies to frequency channels $ch_1$ through $ch_N$. For example, the transmitter and/or the receiver may assign carrier frequency $f_1$ and/or carrier frequency $f_{M/2+1}$ to frequency channel $ch_1$. Likewise, the transmitter and/or the receiver may assign carrier frequency $f_{M/2}$ and/or carrier frequency $f_M$ to frequency channel $ch_2$. Similarly, the transmitter and/or the receiver may assign carrier frequency $f_3$ and/or carrier frequency $f_{M/2+3}$ to frequency channel $ch_3$. Finally, the transmitter and/or the receiver may assign carrier frequency $f_3$ and/or carrier frequency $f_{M/2+3}$ to frequency channel $ch_N$. However, this example is not limiting, those skilled in the arts will recognize that frequency channels $ch_1$ through $ch_N$ may be assigned to any other suitable sequence of carrier frequencies $f_1$ through $f_M$ without departing from the spirit and scope of the invention. Furthermore, to ensure a frequency always has a clear channel, the frequencies can be assigned to the channels so that no frequency is used more than once.

FIG. 33B further illustrates the hopping pattern used to encode and/or decode the acoustic communication signal using the combination of FH and DFSK according to an exemplary embodiment of the present invention. In this exemplary embodiment, carrier frequencies $f_1$ through $f_M$ are partitioned or divided evenly into two sets of carrier frequencies. Carrier frequencies $f_1$ through $f_{(M/2)}$ form a first set of carrier frequencies f. Carrier frequencies $f_{(M/2+1)}$ through $f_M$ form a second set of carrier frequencies F. In an exemplary embodiment, carrier frequencies $f_1$ through $f_{(M/2)}$ are substantially less than or equal to carrier frequencies $f_{(M/2+1)}$ through $f_M$. However, this example is not limiting, those skilled in the arts will recognize that frequency channels $ch_1$ through $ch_N$ may be assigned to one or more sets of carrier frequencies using any other suitable sequence of carrier frequencies $f_1$ through $f_M$ without departing from the spirit and scope of the invention.

As shown in FIG. 33B, first set of carrier frequencies f may be stored in a first set of slots of a data register. Those skilled in the art will recognize that the functionality of the data register may be implemented using other suitable classes of storage media such as a volatile memory, for example a read-only memory (ROM), a non-volatile memory, such as a random access memory (RAM), or any other device capable of storing data without departing from the spirit and scope of the invention. Likewise, second set of carrier frequencies F may be stored in a second set of slots of the data register. The data register may be implemented as a processor register, a hardware register, or any other suitable category of storage area. In addition, the data register may be implemented as, but is not limited to, a general purpose register (GPR) to store both data and addresses, a floating point register (FPR) to store floating point numbers, a constant register to hold read-only values, a vector register to hold data for vector processing done by Single Instruction, Multiple Data (SIMD) instructions, a special function register, or any other suitable class of registers depending on the content of the data. The data register may be implemented as a register file, individual flip-flops, high speed core memory, thin film memory, and any other suitable implementation that will be apparent to those skilled in the art.

The transmitter selects between first set of carrier frequencies f and second set of carrier frequencies F for each frequency channel in frequency channels $ch_1$ through $ch_N$ to encode the information signal. In other words, transitions among first set of carrier frequencies f and second set of carrier frequencies F encode the information signal. As shown in FIG. 33C, the transmitter transmits a carrier frequency from first set of carrier frequencies f for a time interval $t_{AA}$, a time interval $t_{BB}$, and a time interval $t_{CC}$ to represent a first logic value, such as a binary zero-zero. As used herein, the term "logic value" also refers to symbols belonging to sets of indeterminate size, not only to sets having just two states. Time interval $t_{AA}$, time interval $t_{BB}$, and time interval $t_{CC}$ are substantially equal to a corresponding time interval $t_1$ through $t_N$ corresponding to frequency channels $ch_1$ through $ch_N$ as discussed in FIG. 27. Alternately, the transmitter transmits a carrier frequency from second set of carrier frequencies F for a time interval $t_{AA}$, a time interval $t_{BB}$, and a time interval $t_{CC}$ to represent the first logic value.

A second logic value, such as a binary zero-one, may be represented by transmitting the carrier from first set of carrier frequencies f for time interval $t_{AA}$ and time interval $t_{BB}$ followed by the carrier frequency from second set of carrier frequencies F for time interval $t_{CC}$. Alternately, the second logic value may be represented by transmitting the carrier frequency from second set of carrier frequencies F for time interval $t_{AA}$ and time interval $t_{BB}$, followed by the carrier frequency from first set of carrier frequencies f for time interval $t_{CC}$.

A third logic value, such as a binary one-zero, may be represented by transmitting the carrier frequency from second set of carrier frequencies F for time interval $t_{AA}$ and time interval $t_{BB}$ followed by the carrier frequency from first set of carrier frequencies f for time interval $t_{CC}$. Alternately, the third logic value may be represented by transmitting the carrier frequency from first set of carrier frequencies f for time interval $t_{AA}$ and time interval $t_{BB}$, followed by the carrier frequency from second set of carrier frequencies F for time interval $t_{CC}$.

A fourth logic value, such as a binary one-one, may be represented by transmitting the carrier frequency from first set of carrier frequencies f for time interval $t_{AA}$, the carrier frequency from second set of carrier frequencies F for time interval $t_{BB}$, followed by the carrier frequency from first set of carrier frequencies f for time interval $t_{CC}$, Alternately, the fourth logic value may be represented by transmitting the carrier frequency from second set of carrier frequencies F for time interval $t_{AA}$, the carrier frequency from first set of carrier frequencies f for time interval $t_{BB}$, followed by the carrier frequency from second set of carrier frequencies F for time interval $t_{CC}$. However, this example is not limiting, those skilled in the art will recognize that the transmitter may encode the information signal to represent any suitable number of logic values by transmitting any suitable number of carrier frequencies from one or more sets of carrier frequencies without departing from the spirit and scope of the invention. For example, the transmitter may encode the information signal using four sets of carrier frequencies to generate a combined FH and differential quadrature frequency shift keyed (DQFSK) acoustic communication signal, eight sets of carrier frequencies to generate a combined FH and differential 8-frequency shift keyed (D8FSK) acoustic communication signal, and/or M sets of carrier frequencies to generate a combined FH and differential M-frequency shift keyed (DMFSK) acoustic communication signal.

A receiver, such as external computing device 108 or one or more sensor link modules 602 attached to the skin of the body, decodes the acoustic communication signal to recover the information signal. In particular, the receiver detects the carrier frequency from first set of carrier frequencies f and/or the carrier frequency from second set of carrier frequencies F. The receiver compares a detected carrier frequency to a previously detected carrier frequency and assigns a recovered logic value based upon the similarity and/or difference between the detected carrier frequency and the previously detected carrier frequency. The receiver then assigns the recovered logic value to a recovered information signal to recover the information signal.

To decode the acoustic communication signal encoded according to FIG. 33C, the receiver may assign the first logic value to the recovered information signal upon detecting the carrier frequency from first set of carrier frequencies f for time interval $t_{AA}$, time interval $t_{BB}$, and time interval $t_{CC}$. Alternately, the receiver may assign the first logic value to the recovered information signal upon detecting the carrier frequency from second set of carrier frequencies F for time interval $t_{AA}$, time interval $t_{BB}$, and time interval $t_{CC}$.

The receiver may assign the second logic value to the recovered information signal upon detecting the carrier frequency from first set of carrier frequencies f for time interval $t_{AA}$ and time interval $t_{BB}$, then detecting the carrier frequency from second set of carrier frequencies F for time interval $t_{CC}$. Alternately, the receiver may assign the second logic value to the recovered information signal upon detecting the carrier frequency from second set of carrier frequencies F for time interval $t_{AA}$, time interval $t_{BB}$, then detecting the carrier frequency from first set of carrier frequencies f for time interval $t_{CC}$.

The receiver may assign the third logic value to the recovered information signal upon detecting the carrier frequency from second set of carrier frequencies F for time interval $t_{AA}$ and time interval $t_{BB}$, then detecting the carrier frequency from first set of carrier frequencies f for time interval $t_{CC}$. Alternatively, the receiver may assign the third logic value to the recovered information signal upon detecting the carrier frequency from first set of carrier frequencies f for time interval $t_{AA}$ and time interval $t_{BB}$, then detecting the carrier frequency from second set of carrier frequencies F for time interval $t_{CC}$.

The receiver may assign the fourth logic value to the recovered information signal upon detecting the carrier frequency from first set of carrier frequencies f for time interval $t_{AA}$, the carrier frequency from second set of carrier frequencies F for time interval $t_{BB}$, then detecting the carrier frequency from first set of carrier frequencies f for time interval $t_{CC}$. Alternatively, the receiver may assign the fourth logic value to the recovered information signal upon detecting the carrier frequency from second set of carrier frequencies F for time interval $t_{AA}$, the carrier frequency from first set of carrier frequencies f for time interval $t_{BB}$, then detecting the carrier frequency from second set of carrier frequencies F for time interval $t_{CC}$. However, this example is not limiting, those skilled in the art will recognize that the receiver may decode the acoustic communication signal to represent any suitable number of logic values by detecting any suitable number of carrier frequencies from one or more sets of carrier frequencies without departing from the spirit and scope of the invention. For example, the receiver may decode the acoustic communication signal using four sets of carrier frequencies to decode the combined FH and DQFSK acoustic communication signal, eight sets of carrier frequencies to decode the combined FH and D8FSK acoustic communication signal, and/or M sets of carrier frequencies to decode the combined FH and DMFSK acoustic communication signal.

v. Combination of Frequency Hopping and Differential Frequency Shift Keying, and Differential Phase Shift Keying FIG. 34A illustrates a combined FH, DFSK, and DPSK scheme to encode and/or decode an acoustic communication signal according to an exemplary embodiment of the present invention. From the discussion of FIG. 27 above, a transmitter, such as communications module 204, transmits an acoustic communication signal 3400, such as communication signal 106, by encoding an information signal, such as sensor output signal 212, onto frequency channels $ch_1$ through $ch_N$ corresponding to time intervals $t_1$ through $t_N$. From the discussion of FIG. 33A, frequency channels $ch_1$ through $ch_N$ may be assigned to a first set of carrier frequencies f including carrier frequencies $f_1$ through $f_{M/2}$ and a second set of carrier frequencies F including carrier frequencies $f_{M/2+1}$ through $f_{M/2}$. Referring back to FIG. 34A, the transmitter embeds one or more phases, denoted as $\phi_1$ through $\phi_i$, of a corresponding carrier frequency from first set of carrier frequencies f and/or one or more phases $\phi_1$ through $\phi_i$ from second set of carrier frequencies F onto frequency channels $ch_1$ through $ch_N$ to encode the information signal. The transmitter embeds one or more phases $\phi_1$ through $\phi_i$ corresponding to one or more sets of carrier frequencies onto each frequency channel in frequency channels $ch_1$ through $ch_N$ to encode the information signal.

As shown in FIGS. 34B and 34C, the transmitter transmits a first phase $\phi_1$ of a carrier frequency from first set of carrier frequencies f for a time interval $t_A$ and a time interval $t_B$ corresponding to a time interval $t_{AA}$, and a time interval $t_A$ and a time interval $t_B$ corresponding to a time interval $t_{BB}$ to represent a first logic value, such as a binary zero-zero-zero. A combination of time interval $t_A$ and time interval $t_B$ is substantially less than or equal to corresponding time interval $t_{AA}$ and/or corresponding time interval $t_{BB}$. Time interval $t_{AA}$ and time interval $t_{BB}$ is substantially less than or equal to corresponding time intervals $t_1$ through $t_N$ as discussed in FIG. 27.

A second logic value, such as a binary zero-zero-one, may be represented by transmitting the first phase $\phi_1$ of the carrier frequency from first set of carrier frequencies f for time interval $t_A$ and time interval $t_B$ corresponding to time interval $t_{AA}$, then the first phase $\phi_1$ of the carrier frequency from first set of carrier frequencies f for time interval $t_A$ followed by a second phase $\phi_2$ of the carrier frequency from first set of carrier frequencies f for time interval $t_B$, time interval $t_A$ and time interval $t_B$ corresponding to time interval $t_{BB}$.

A third logic value, such as a binary zero-one-one, may be represented by transmitting the first phase $\phi_1$ of the carrier frequency from first set of carrier frequencies f for time interval $t_A$ and time interval $t_B$ corresponding to time interval $t_{AA}$ then a first phase $\phi_3$ of the carrier frequency from second set of carrier frequencies F for time interval $t_A$ followed by a second phase $\phi_4$ of the carrier frequency from second set of carrier frequencies F for time interval $t_B$, time interval $t_A$ and time interval $t_B$ corresponding to the time interval $t_{BB}$.

A fourth logic value, such as binary zero-one-zero, may be represented by transmitting the first phase $\phi_1$ of the carrier frequency from first set of carrier frequencies f for time interval $t_A$ and time interval $t_B$ corresponding to time interval $t_{AA}$, then the first phase $\phi_3$ of the carrier frequency from second set of carrier frequencies F for time interval $t_A$ and time interval $t_B$ corresponding to time interval $t_{BB}$.

A fifth logic value, such as binary one-zero-zero, may be represented by transmitting the first phase $\phi_1$ of the carrier frequency from first set of carrier frequencies f for time interval $t_A$ followed by the second phase $\phi_2$ of the carrier frequency from first set of carrier frequencies f for time interval $t_B$, time interval $t_A$ and time interval $t_B$ corresponding to time interval $t_{AA}$, then the second phase $\phi_2$ of the carrier frequency from first set of carrier frequencies f for time interval $t_A$ and time interval $t_B$ corresponding to time interval $t_{BB}$.

A sixth logic value, such as binary one-zero-one, may be represented by transmitting the first phase $\phi_1$ of the carrier frequency from first set of carrier frequencies f for time interval $t_A$ followed by the second phase $\phi_2$ of the carrier frequency from first set of carrier frequencies f for time interval $t_B$, time interval $t_A$ and time interval $t_B$ corresponding to time interval $t_{AA}$, then the second phase $\phi_2$ of the carrier frequency from first set of carrier frequencies f for time interval $t_A$ followed by the by the second phase $\phi_2$ of the carrier frequency from first set of carrier frequencies f for time interval $t_B$, time interval $t_A$ and time interval $t_B$ corresponding to time interval $t_{BB}$.

A seventh logic value, such as binary one-one-one, may be represented by transmitting the first phase $\phi_1$ of the carrier frequency from first set of carrier frequencies f for time interval $t_A$ followed by the second phase $\phi_2$ of the carrier frequency from first set of carrier frequencies f for time interval $t_B$, time interval $t_A$ and time interval $t_B$ corresponding to time interval $t_{AA}$, then the first phase $\phi_3$ of the carrier frequency from second set of carrier frequencies F for time interval $t_A$ followed by the second phase $\phi_4$ of the carrier frequency from second set of carrier frequencies F for time interval $t_B$, time interval $t_A$ and time interval $t_B$ corresponding to time interval $t_{BB}$.

An eighth logic value, such as binary one-one-zero, may be represented by transmitting the first phase $\phi_1$ of the carrier frequency from first set of carrier frequencies f for time interval $t_A$ followed by the second phase $\phi_2$ of the carrier frequency from first set of carrier frequencies f for time interval $t_B$, time interval $t_A$ and time interval $t_B$ corresponding to time interval $t_{AA}$, then the first phase $\phi_3$ of the carrier frequency from second set of carrier frequencies F for time interval $t_A$ and time interval $t_B$ corresponding to time interval $t_{BB}$. However, this example is not limiting, those skilled in the art will recognize that the transmitter may encode the information signal to represent any suitable number of logic values by transmitting any suitable number of carrier frequencies from one or more sets of carrier frequencies where each carrier frequency includes one or more phase $\phi_1$ through $\phi_i$ without departing from the spirit and scope of the invention.

FIG. 35 illustrates a block diagram of a transmitter to encode an information signal to a combination of FH, DFSK and DPSK acoustic communication signal according to an exemplary embodiment of the present invention. A transmitter 3500 may be used to generate an acoustic communication signal 3552, such as communication signal 3400 as shown in FIG. 34A, based on an information signal 3550, such as sensor output signal 212. Transmitter 3500 may represent an exemplary embodiment of communications module 204. As will be understood by persons skilled in the relevant art from the teachings provided herein, transmitter 3500 may be readily implemented in hardware, software, or a combination of hardware and software. For example, based on the teachings provided herein, a person skilled in the relevant art could implement transmitter 3500 via a combination of one or more application specific integrated circuits and a processor core for implementing software commands stored in one or more attached memories. However, this example is not limiting, and other implementations are within the scope and spirit of the present invention.

As shown in FIG. 35, transmitter 3500 may include an acoustic communications module 3502 and a radiating element 3504. Acoustic communications module 3502 includes a bit splitter 3504, a multiplier 3506, a delay module 3508, a carrier generator 3510, a DFSK switch 3512, a phase shifting module 3514, and a DPSK switch 3516. Acoustic communications module 3502 may represent an exemplary embodiment of acoustic communications module 302.

Bit splitter 3504 receives information signal 3550. Bit splitter 3504 parses or partitions the information signal 3550 into a first data stream 3554A and a second data stream 3554B. Bit splitter 3504 may partition information signal 3550 into one or more bits, one or more bytes, one or more symbols, or any other suitable manner that will be apparent to those skilled in the relevant art. First bit stream 3554A and second bit stream 3554B may be of similar or of dissimilar lengths.

A multiplier 3506A compares first data stream 3554A to a first delayed DPSK switch control signal 3556A to produce a DPSK switch control signal 3558A. A first delay module 3508A delays DPSK switch control signal 3558A by one or more bits, one or more bytes, one or more symbols, or any other suitable manner based upon a data length of the DPSK switch control signal 3558A to produce first delayed DPSK switch control signal 3556A. In an exemplary embodiment, first delay module 3508A delays DPSK switch control signal 3558A by one bit. Likewise, a multiplier 3506B multiplies second data stream 3554B and a second delayed encoded data stream 3556B to produce a second encoded data stream 3558B. A second delay module 3508B delays second encoded data stream 3558B by one or more bits, one or more bytes, one or more symbols, or any other suitable manner based upon a data length of the second encoded data stream 3558B to produce second delayed encoded data stream 3558B. In an exemplary embodiment, second delay module 3508B delays second encoded data stream 3558B by one bit.

The carrier generator 3510 generates a first carrier frequency 3562A from a first set of carrier frequencies and a second carrier frequency 3562B from a second set of carrier frequencies. More specifically, carrier generator 3510 generates one or more carrier frequencies, such as carrier frequencies $f_1$ through $f_M$ to provide an example, according to the FH scheme as discussed in conjunction with FIG. 27. Carrier generator 3510 then divides the one or more carrier frequencies into the first set of carrier frequencies and the second set of carrier frequencies as discussed in FIG. 33A.

The DFSK switch 3512 selects between first carrier frequency 3562A and second carrier frequency 3562B based upon second encoded data stream 3558B to generate a DFSK data stream 3564. For example, DPSK switch 3516 may select first carrier frequency 3562A when second encoded data stream 3558B corresponds to a first logical value, such as a binary zero to provide an example. Likewise, DPSK switch 3516 may select second carrier frequency 3562B when second encoded data stream 3558B corresponds to a second logical value, such as a binary one to provide an example.

Phase shifting module 3514 alters a phase of DFSK data stream 3564 to produce a phase shifted DFSK data stream 3566. In an exemplary embodiment, phase shifting module 3514 alters the phase of DFSK data stream 3564 by one hundred eighty degrees by inverting DFSK data stream 3564. DPSK switch 3516 selects between DFSK data stream 3564 and phase shifted DFSK data stream 3566 based upon first encoded data stream 3558B to generate a combined DFSK and DPSK data stream 3568. For example, DPSK switch 3516 may select phase shifted DFSK data stream 3566 when DPSK switch control signal 3558A corresponds to a first logical value, such as a binary zero to provide an example. Likewise, DPSK switch 3516 may select DFSK data stream 3564 when DPSK switch control signal 3558A corresponds to a second logical value, such as a binary one to provide an example.

Radiating element 3504 converts combined DFSK and DPSK data stream 3568 to an acoustic representation to generate acoustic communication signal 3552 based upon combined DFSK and DPSK data stream 3568. Radiating element 3504 may represent an exemplary embodiment of radiating element 304. Radiating element 3504 may be, but is not limited to, an electromechanical transducer or piezoelectric (e.g., PZT, PVDF, etc.) element or transducer that vibrates at acoustic frequencies.

FIG. 36 illustrates a block diagram of a receiver to decode an information signal from an acoustic communication signal encoded using a combination of FH, DFSK and DPSK according to an exemplary embodiment of the present invention. A receiver 3600, such as external computing device 108 or one or more sensor link modules 602 attached to the skin of the body, decodes an acoustic communication signal 3650 to recover a DFSK component 3652 and a DPSK component 3654. As shown in FIG. 36, receiver 3600 may include a radiating element 3602, a carrier generator 3604, a DFSK/DPSK demodulator 3606, a DPSK switch 3608, and a differential decoder 3610.

Radiating element 3602 receives acoustic communication signal 3650, such as acoustic communication signal 3400 to provide an example. Radiating element 3602 converts acoustic communication signal 3650 to an electrical signal to generate an electrical communication signal 3656. Radiating element 3602 may be, but is not limited to, an electromechanical transducer or piezoelectric (e.g., PZT, PVDF, etc.) element or transducer that vibrates at acoustic frequencies.

Carrier generator 3604 generates a first carrier frequency 3658A from a first set of carrier frequencies and a second carrier frequency 3658B from a second set of carrier frequencies. More specifically, carrier generator 3604 generates one or more carrier frequencies, such as carrier frequencies $f_1$ through $f_M$ to provide an example, according to the FH scheme as discussed in conjunction with FIG. 27. Carrier generator 3604 then divides the one or more carrier frequencies into the first set of carrier frequencies and the second set of carrier frequencies as discussed in FIG. 33A.

DFSK/DPSK demodulator 3606 demodulates electrical communication signal 3656 using a corresponding carrier frequency to produce a corresponding DFSK output 3660 and a corresponding DPSK output 3662. More specifically, DFSK/DPSK demodulator 3606A demodulates electrical communication signal 3656 using first carrier frequency 3658A from the first set of carrier frequencies to produce a DFSK output 3660A and a DPSK output 3662A. Likewise, DFSK/DPSK demodulator 3606B demodulates electrical communication signal 3656 using second carrier frequency 3658B from the second set of carrier frequencies to produce a DFSK output 3660B and a DPSK output 3662B.

FIG. 37 illustrates a block diagram of a demodulator to decode an information signal from an acoustic communication signal encoded using a combination of FH, DFSK, and DPSK according to an exemplary embodiment of the present invention. DFSK/DPSK demodulator 3700 is an exemplary embodiment of DFSK/DPSK demodulator 3606A and/or DFSK/DPSK demodulator 3606B as shown in FIG. 36.

Referring to FIG. 37, DFSK/DPSK demodulator 3700 operates upon electrical communication signal 3656 using a corresponding carrier frequency 3658 to produce a corresponding DFSK output 3660 and a corresponding DPSK output 3662. DFSK/DPSK demodulator 3700 includes a multiplier 3702, a phase shifter 3704, an integrator 3706, a multiplier 3708, a delay module 3710, a summation network 3712, an in-phase correlator 3714, an in-phase correlator 3716, a decision device 3718, a quadrature phase correlator 3720, a quadrature phase correlator 3722, and a summation network 3724.

Multiplier 3702 downconverts electrical communication signal 3656 using a corresponding carrier frequency to produce a corresponding downconverted communication signal 3752. More specifically, a first multiplier 3702A downconverts electrical communication signal 3656 using carrier frequency 3658 to produce a first downconverted communication signal 3752A. Likewise, a second multiplier 3702B downconverts electrical communication signal 3656 using a phase shifted carrier frequency 3750 to produce a second downconverted communication signal 3752B. Phase shifter 3704 delays or shifts a phase of carrier frequency 3658 to produce phase shifted carrier frequency 3750. In an exemplary embodiment, phase shifter 3704 shifts the phase of carrier frequency 3658 by ninety degrees.

Integrator 3706 integrates a corresponding downconverted communication signal 3752. More specifically, integrator 3706A accumulates first downconverted communication signal 3752A within each half-symbol interval of T/2 to produce an in-phase information signal 3754A. Likewise, integrator 3706B accumulates second downconverted communication signal 3752B within each half-symbol interval of T/2 to produce a quadrature phase information signal 3754B.

Multiplier 3708 multiplies in-phase information signal 3754A and/or quadrature phase information signal 3754B with a delayed in-phase information signal 3756A and/or a delayed quadrature phase information signal 3756B. More specifically, multiplier 3708A multiplies in-phase information signal 3754A with delayed in-phase information signal 3756A to produce an in-phase decision statistic 3758A. Delay module 3710A delays in-phase information signal 3754A by a half-symbol interval of T/2 to produce delayed in-phase information signal 3756A. Likewise, multiplier 3708B multiplies quadrature phase information signal 3754B with delayed quadrature phase information signal 3756B to produce a quadrature phase decision statistic 3758B. Delay module 3710B delays quadrature phase information signal 3754B by a half-symbol interval of T/2 to produce delayed quadrature phase information signal 3756B.

Summation network 3712 combines in-phase decision statistic 3758A and in-phase decision statistic 3758A to produce a decision statistic 3760. Decision device 3718 assigns a logic value to DPSK output 3662 based upon decision statistic 3760. In an exemplary embodiment, decision device 3718 implements a signum function. For example, when decision statistic 3760 is less than zero, decision device 3718 assigns a first bit estimate to DPSK output 3662. Likewise, when decision statistic 3760 is greater than zero, decision device 3718 assigns a second bit estimate to DPSK output 3662.

In-phase correlator 3714 correlates in-phase information signal 3754A to produce a correlated in-phase information signal 3762A. Likewise, in-phase correlator 3716 correlates delayed in-phase information signal 3756A to produce a correlated delayed in-phase information signal 3762B. Quadrature phase correlator 3720 correlates quadrature information signal 3754B to produce a correlated quadrature information signal 3764A. Likewise, quadrature correlator 3722 correlates delayed quadrature information signal 3756B to produce a correlated delayed in-phase information signal 3764B. Summation network 3724 then combines correlated in-phase information signal 3762A, correlated delayed in-phase information signal 3762B, correlated quadrature information signal 3764B, and correlated delayed in-phase information signal 3764B to produce DFSK output 3660.

FIG. 38 illustrates a block diagram of a demodulator to decode an information signal from an acoustic communication signal encoded using a combination of FH, DFSK, and DPSK according to another exemplary embodiment of the present invention. DFSK/DPSK demodulator 3800 is an exemplary embodiment of DFSK/DPSK demodulator 3606A and/or DFSK/DPSK demodulator 3606B as shown in FIG. 36.

Referring to FIG. 38, DFSK/DPSK demodulator 3800 operates upon electrical communication signal 3656 using a corresponding carrier frequency 3658 to produce a corresponding DFSK output 3660 and a corresponding DPSK output 3662. DFSK/DPSK demodulator 3800 includes a multiplier 3802, a phase shifter 3804, an integrator 3806, a multiplier 3808, a delay module 3810, a multiplier 3812, a summation network 3814, a difference network 3816, a decision device 3818, a decision device 3820, a bit combiner 3822, an in-phase correlator 3824, an in-phase correlator 3826, a quadrature phase correlator 3828, a quadrature phase correlator 3830, and a summation network 3832. Multiplier 3802 downconverts electrical communication signal 3656 using a corresponding carrier frequency to produce a corresponding downconverted communication signal 3852. More specifically, a first multiplier 3802A downconverts electrical communication signal 3656 using carrier frequency 3658 to produce a first downconverted communication signal 3852A. Likewise, a second multiplier 3802B downconverts electrical communication signal 3656 using a phase shifted carrier frequency 3850 to produce a second downconverted communication signal 3852B. Phase shifter 3804 delays or shifts a phase of carrier frequency 3658 to produce phase shifted carrier frequency 3850. In an exemplary embodiment, phase shifter 3804 shifts the phase of carrier frequency 3658 by ninety degrees.

Integrator 3806 integrates a corresponding downconverted communication signal 3852. More specifically, integrator 3806A accumulates first downconverted communication signal 3852A within each half-symbol interval of T/2 to produce an in-phase information signal 3854A. Likewise, integrator 3806B accumulates second downconverted communication signal 3852B within each half-symbol interval of T/2 to produce a quadrature phase information signal 3854B.

Multiplier 3808 multiplies in-phase information signal 3854A and/or quadrature phase information signal 3854B with a delayed in-phase information signal 3856A and/or a delayed quadrature phase information signal 3856B. More specifically, multiplier 3808A multiplies in-phase information signal 3854A with delayed in-phase information signal 3856A to produce an in-phase decision statistic 3858A. Delay module 3810A delays in-phase information signal 3854A by a half-symbol interval of T/2 to produce delayed in-phase information signal 3856A. Likewise, multiplier 3808B multiplies quadrature phase information signal 3854B with delayed quadrature phase information signal 3856B to produce a quadrature phase decision statistic 3858B. Delay module 3810B delays quadrature phase information signal 3854B by a half-symbol interval of T/2 to produce delayed quadrature phase information signal 3856B.

Multiplier 3828A multiplies in-phase phase information signal 3854A with quadrature phase information signal 3854B to produce a decision statistic 3860A. Likewise, multiplier 3828B multiplies in-phase phase information signal 3854B with quadrature phase information signal 3854B to produce a decision statistic 3860B.

Summation network 3814 combines in-phase decision statistic 3858A and in-phase decision statistic 3858A to produce a decision statistic 3862. Likewise, difference network 3816 subtracts decision statistic 3860A and decision statistic 3860B to produce a decision statistic 3864. Decision device 3818 assigns a logic value to a first DPSK output 3866 based upon decision statistic 3862. In an exemplary embodiment, decision device 3818 implements a signum function. For example, when decision statistic 3862 is less than zero, decision device 3818 assigns a first bit estimate to first DPSK output 3866. Likewise, when decision statistic 3860 is greater than zero, decision device 3818 assigns a second bit estimate to first DPSK output 3866. Similarly, decision device 3820 assigns a logic value to a second DPSK output 3868 based upon decision statistic 3862. In an exemplary embodiment, decision device 3820 implements a signum function. For example, when decision statistic 3862 is less than zero, decision device 3820 assigns a first bit estimate to the second DPSK output 3868. Likewise, when decision statistic 3860 is greater than zero, decision device 3820 assigns a second bit estimate to second DPSK output 3868. Bit combiner 3822 combines first DPSK output 3868 and second DPSK output 3868 to produce DPSK output 3662A.

In-phase correlator 3824 correlates delayed in-phase information signal 3856A to produce a correlated delayed in-phase information signal 3870A. Likewise, in-phase correlator 3826 correlates in-phase information signal 3854A to produce a correlated in-phase information signal 3870B. Quadrature phase correlator 3828 correlates quadrature information signal 3854B to produce a correlated quadrature information signal 3872A. Likewise, quadrature correlator 3830 correlates delayed quadrature information signal 3856B to produce a correlated delayed in-phase information signal 3872B. Summation network 3832 then combines correlated in-phase information signal 3870A, correlated delayed in-phase information signal 3870B, correlated quadrature information signal 3872A, and correlated delayed in-phase information signal 3872B to produce DFSK output 3660.

Referring back to FIG. 36, differential decoder 3610 produces DFSK component 3652 based upon DFSK output 3660A and DFSK output 3660B. In an exemplary embodiment, differential decoder 3610 assigns a first logic value, such as a binary zero, to DFSK component 3652 when the combination of DFSK output 3660A and DFSK output 3660B is substantially equal to zero. Otherwise, differential decoder 3610 assigns a second logic value, such as a binary one, to DFSK component 3652 when the combination of DFSK output 3660A and DFSK output 3660B is substantially equal to one. In addition, differential decoder 3610 produces a DPSK selection signal 3670.

DPSK switch 3608 selects DPSK output 3662A or DPSK output 3662B based upon DPSK selection signal 3670 to produce DPSK component 3654. For example, DPSK switch 3608 selects DPSK output 3662A when DPSK selection signal 3670 corresponds to a first logic value, such as a binary zero. Likewise, DPSK switch 3608 selects DPSK output 3662B when DPSK selection signal 3670 corresponds to a second logic value, such as a binary one.

vi. Use of Multiple Frequency Bands with a Combination of Frequency Hopping and Time Interval Encoding FIG. 39A illustrates a hopping pattern used to encode and/or decode an acoustic communication signal using multiple frequency bands with FH according to an exemplary embodiment of the present invention. As shown in FIG. 39A, an available bandwidth of the communication channel is substantially equally divided into three frequency bands $B_1$ through $B_3$. For example, as shown in FIG. 39A, frequency band $B_1$ includes a first bandwidth encompassing carrier frequencies $f_1$ through $f_i$, frequency band $B_2$ includes a second bandwidth encompassing carrier frequencies $f_{i+1}$ through $f_{M-i-1}$, and frequency band $B_3$ includes a third bandwidth encompassing carrier frequencies $f_{M-i}$ through $f_M$. However, this example is not limiting, the available bandwidth of the communication channel may be divided into one or more frequency bands $B_1$ through $B_K$. In addition, the available bandwidth of the communication channel need not be substantially equally divided into one or more frequency bands $B_1$ through $B_K$. For example, frequency band $B_1$ may encompass a greater amount of the available bandwidth of the communication channel when compared to frequency band $B_2$.

In an embodiment utilizing substantially different frequency bands $B_1$ and $B_2$, a received amplitude of a particular first frequency in band $B_1$ as compared with a received amplitude of a particular second frequency in band $B_2$ can derive distance from a sensor device 104 to a receiver such as sensor link 602. Acoustic attenuation of signals is proportional to a frequency of transmission for a given medium, such as with human body 102. However, the knowledge of absolute amplitude of emission is not easily attainable for a reference to calculate a distance from a resulting attenuation. Considering multiple frequencies with multiple amplitudes, a sensitive receiver may be able to calculate with accuracy a difference between received amplitudes of these two frequencies. A mathematical model with known quantities of attenuation versus distance for both frequencies may then also solve a difference of known attenuations versus distances for both frequencies. In such an example, there is only one final solution that resolves the distance from a match of amplitude differentials with the difference in amplitude actually received. In so doing, use of a single phased array receiver (for the direction component of the location) in combination with use of multiple frequency bands (for the distance component of the location) can potentially resolve the location of the origin of acoustic signals to a reasonable accuracy.

Referring back to FIG. 39A, a pulse $P_1$ through $P_N$ may be assigned a corresponding carrier frequency from one or more frequency bands $B_1$ through $B_K$. For example, pulse $P_1$ may be assigned to carrier frequency $f_1$ from frequency band $B_1$, carrier frequency $f_{i+1}$ from frequency band $B_2$, and/or carrier frequency $f_{M-i}$ from frequency band $B_3$. However, this example is not limiting, those skilled in the arts will recognize that pulses $P_1$ through $P_N$ may be assigned to one or more frequency bands $B_1$ through $B_K$ using any other suitable sequence of carrier frequencies $f_1$ through $f_M$ without departing from the spirit and scope of the invention. In an exemplary embodiment, one or more pulses $P_1$ through $P_N$ are sequentially assigned to the carrier frequencies. After transmission and/or reception of pulse $P_1$ using a carrier frequency from one of frequency bands $B_1$ through $B_3$, a transmitter and/or a receiver sequentially reassigns the carrier frequency associated with the frequency band according to the hopping scheme. For example, if pulse $P_1$ is transmitted and/or received using carrier frequency $f_1$ associated with frequency band $B_1$, the transmitter and/or a receiver reassigns frequency band $B_1$ to a next carrier frequency according to the hopping scheme and leaves frequency bands $B_2$ and $B_3$ in their current state.

FIG. 39B illustrates a multiple frequency band with FH scheme to encode and/or decode an acoustic communication signal according to an exemplary embodiment of the present invention. A transmitter, such as communications module 204, transmits an acoustic communication signal, such as communication signal 106, by encoding an information signal, such as sensor output signal 212, using one or more pulses $P_1$ through $P_N$ as described in FIG. 39A.

The transmitter selects one or more pulses $P_1$ through $P_N$ from frequency bandwidths $B_1$ through $B_3$ to encode the information signal. As shown in FIG. 39B, the transmitter transmits a first pulse, such as pulse $P_1$, assigned to a carrier frequency from frequency band $B_1$ for a time interval $t_{AA}$ and a time interval $t_{BB}$ followed by a third pulse, such as pulse $P_3$, assigned to a carrier frequency from frequency band $B_3$ for time interval $t_{CC}$ to represent a first logic value, such as a binary zero-zero. Time interval $t_{AA}$, time interval $t_{BB}$, and time interval $t_{CC}$ are greater than or equal to a duration of a corresponding pulse in one or more pulses $P_1$ through $P_N$. In an exemplary embodiment, third pulse $P_3$ indicates an end of a transmission. However, this example is not limiting, those skilled in the arts will recognize that any one of pulses $P_1$ through $P_N$ may be used to indicate the end of the transmission without departing from the spirit and scope of the invention.

A second logic value, such as a binary zero-one, may be represented by transmitting the first pulse assigned to the carrier frequency from frequency band $B_1$ for time interval $t_{AA}$, a second pulse, such as pulse $P_2$, assigned to a carrier frequency from frequency band $B_2$ for time interval $t_{BB}$, and third pulse $P_3$ assigned to a carrier frequency from frequency band $B_3$ for time interval $t_{CC}$ to indicate the end of transmission.

A third logic value, such as a binary one-one, may be represented by transmitting the pulse assigned to the carrier frequency from frequency band $B_2$ for time interval $t_{AA}$ and time interval $t_{BB}$, followed by the third pulse assigned to a carrier frequency from frequency band $B_3$ for time interval $t_{CC}$ to indicate the end of transmission.

A fourth logic value, such as a binary one-zero, may be represented by transmitting the pulse assigned to the carrier frequency from frequency band $B_2$ for time interval $t_{AA}$, a pulse assigned to the carrier frequency from frequency band $B_1$ for time interval $t_{BB}$, followed by the third pulse assigned to the carrier frequency from frequency band $B_3$ for time interval $t_{CC}$. However, this example is not limiting, any logic value may be represented by transmitting pulses $P_1$ through $P_N$ assigned to carrier frequencies from frequency bands $B_1$ through $B_K$. For example, a binary zero-zero-zero-one-zero-one-one-zero may be represented by transmitting the first pulse, the second pulse, and the third pulse assigned to a carrier frequency from frequency band $B_1$, a fourth pulse assigned to a carrier frequency from frequency band $B_2$, a fifth pulse assigned to a carrier frequency from frequency band $B_1$, a sixth and a seventh pulse assigned to a carrier frequency from frequency band $B_2$, and an eighth pulse assigned to a carrier frequency from frequency band $B_1$, followed by a ninth pulse assigned to a carrier frequency from frequency band $B_3$ to indicate the end of transmission.

A receiver, such as external computing device 108 or one or more sensor link modules 602 attached to the skin of the body, decodes the acoustic communication signal to recover the information signal. The receiver assigns the recovered logic value by detecting the carrier frequency from frequency band $B_1$, and/or the carrier frequency from frequency band $B_2$ until the end of transmission as indicated by detecting the carrier frequency from frequency band $B_3$. In an exemplary embodiment, the receiver includes three detection circuits, one detection circuit for each frequency band $B_1$ through $B_3$.

To decode the acoustic communication signal encoded according to FIG. 39B, the receiver may assign the first logic value to a recovered information signal by detecting first pulse $P_1$ assigned to the carrier frequency from frequency band $B_1$ for a time interval $t_{AA}$ and a time interval $t_{BB}$ followed by third pulse $P_3$ assigned to the carrier frequency from frequency band $B_3$ for time interval $t_{CC}$ to indicate the end of transmission.

The receiver may assign the second logic value to the recovered information signal by detecting first pulse $P_1$ assigned to the carrier frequency from frequency band $B_1$ for time interval $t_{AA}$, second pulse $P_2$ assigned to the carrier frequency from frequency band $B_2$ for time interval $t_{BB}$, followed by third pulse $P_3$ assigned to the carrier frequency from frequency band $B_3$ for time interval $t_{CC}$ to indicate the end of transmission.

The receiver may assign the third logic value to the recovered information signal by detecting pulse $P_2$ assigned to the carrier frequency from frequency band $B_2$ for time interval $t_{AA}$ and time interval $t_{BB}$, followed by third pulse $P_3$ assigned to the carrier frequency from frequency band $B_3$ for time interval $t_{CC}$ to indicate the end of transmission.

The receiver may assign the fourth logic value to the recovered information signal by detecting pulse $P_2$ assigned to the carrier frequency from frequency band $B_2$ for time interval $t_{AA}$, first pulse $P_1$ assigned to the carrier frequency from frequency band $B_1$ for time interval $t_{BB}$, followed by a third pulse $P_3$ assigned to the carrier frequency from frequency band $B_3$ for time interval $t_{CC}$ to indicate the end of transmission. However, this example is not limiting, any logic value may be represented by transmitting pulses $P_1$ through $P_N$ for any suitable number of time intervals. For example, the receiver may assign a binary zero-zero-zero-one-zero-one-one-zero to the recovered information signal by detecting the first pulse, the second pulse, and the third pulse assigned to a carrier frequency from frequency band $B_1$, a fourth pulse assigned to a carrier frequency from frequency band $B_2$, a fifth pulse assigned to a carrier frequency from frequency band $B_1$, a sixth and a seventh pulse assigned to a carrier frequency from frequency band $B_2$, and an eighth pulse assigned to a carrier frequency from frequency band $B_1$ followed by a ninth pulse assigned to a carrier frequency from frequency band $B_3$ to indicate the end of transmission.

FIG. 39C illustrates a multiple frequency band with FH and time interval encoding scheme to encode and/or decode an acoustic communication signal according to an exemplary embodiment of the present invention. As shown in FIG. 39C, a corresponding time delay $T_1$ through $T_N$ having one or more time delay intervals, denoted as $\tau_N$, may be used to implement a repeat function. The duration of time delay interval $\tau_N$ is substantially less than or equal to the duration of a corresponding pulse in one or more pulses $P_1$ through $P_N$. The repeat function indicates that the next bits of the acoustic communication signal are substantially equal to a previous bit transmitted and/or received based upon a number of time delay intervals $\tau_N$. More specifically, delaying by a time delay interval $\tau_N$ after a binary one indicates that the next bits in the acoustic communication signal also indicate a binary one. Likewise, delaying by two time delay intervals $\tau_N$ after a binary one indicates that the two next bits in the acoustic communication signal also indicate a binary one. For example, the repeat function allows an eight bit word represented by binary zero-one-one-one-one-one-one-one to be encoded and/or decoded by transmitting and/or receiving a first pulse assigned to a carrier frequency from frequency band $B_1$, a second pulse assigned to a carrier frequency from frequency band $B_2$, and a period of five time delay intervals $\tau_N$, followed by a third pulse assigned to a carrier frequency from frequency band $B_3$ to indicate the end of transmission.

The repeat function may also allow for the repetition of one or more bits, one or more bytes, one or more symbols, or any other suitable data length or combination of data lengths. For example, the repeat function may also allow the eight bit word represented by binary zero-one-one-one-one-one-one-one to be repeated n times by transmitting and/or receiving a first pulse assigned to a carrier frequency from frequency band $B_1$, a second pulse assigned to a carrier frequency from frequency band $B_2$, a period of five time delay intervals $\tau_N$, a third pulse assigned to a carrier frequency from frequency band $B_3$, a period of n delay intervals $\tau_N$, followed by a fourth pulse assigned to a carrier frequency from frequency band $B_3$ to indicate the end of transmission.

In another exemplary embodiment, the pulse assigned to a carrier frequency from frequency band $B_3$ may be used to implement a truncation function. The truncation function indicates that the remaining bits of the acoustic communication signal are substantially equal to a previous bit transmitted and/or received. More specifically, truncating after a binary one indicates that the rest of the bits in the acoustic communication signal are also binary one. Likewise, truncating after a binary zero indicates that the rest of the bits in the acoustic communication signal are also binary zero. For example, the truncation function allows an eight bit word represented by binary zero-one-one-one-one-one-one-one to be encoded and/or decoded using substantially similar encoding and/or decoding as the second logic value as discussed above. In this example, third pulse $P_3$ assigned to a carrier frequency from frequency band $B_3$ indicates that the remaining six bits of the eight bit word are equal to a previous bit transmitted and/or received. Likewise, the truncation function allows an eight bit word represented by binary one-zero-zero-zero-zero-zero-zero-zero to be encoded and/or decoded using substantially similar encoding and/or decoding as the fourth logic value as discussed above. However, these examples are not limiting, the truncation function may be used to indicate that any suitable number of bits are substantially equal to the previous bit transmitted and/or received. In addition, the transmitter and/or the receiver may use the truncation function in any location throughout the encoding and/or decoding of the acoustic communication signal.

In a further exemplary embodiment, the corresponding time delays $T_1$ through $T_N$, including one or more time delay intervals $\tau_N$, may be additionally used to encode the acoustic communication signal. In this exemplary embodiment, the transmitter transmits a first pulse assigned to a carrier frequency from one of the frequency bands, such as pulse $P_1$ assigned to a carrier frequency from frequency band $B_1$, for a first interval of time, such as time interval $t_1$. The transmitter then waits or ceases to transmit for a corresponding time delay, such as time delay $T_1$, before beginning the transmission of a second pulse assigned to a carrier frequency from one of the frequency bands, such as pulse $P_2$ including a carrier frequency from frequency band $B_2$. The transmitter encodes the information signal by varying a length of the corresponding time delay. More specifically, the transmitter encodes the information signal by delaying the transmission of the pulse by one or more time delay intervals $\tau_N$. The one or more time delay intervals $\tau_N$ within a corresponding time delay $T_1$ through $T_N$ represent a logic value. The logic value may be one or more bits, one or more bytes, one or more symbols, or any other suitable data length or combination of data lengths. An individual delay interval in one or more time delay intervals $\tau_N$ may be a duration of one or more bits, one or more bytes, one or more symbols, or any other suitable data length or combination of data lengths so long as the duration of an individual delay interval $\tau_N$ is substantially less than or equal to the duration of a corresponding pulse in one or more pulses $P_1$ through $P_N$.

In an additional exemplary embodiment, a pulse assigned to a carrier frequency from one of the frequency bands transmitted and/or received prior to one or more time delay intervals $\tau_N$ may be used to implement an advancement function. In other words, the pulse assigned to the carrier frequency from one of the frequency bands transmitted and/or received prior to one or more time delay intervals $\tau_N$ may correspond to a number of one or more time delay intervals $\tau_N$. In other words, the transmitter and/or the receiver supplements a transmitted and/or a received one or more time delay intervals $\tau_N$ with a predetermined number of the one or more time delay intervals $\tau_N$.

As shown in FIG. 39D, a first pulse assigned to a carrier frequency from a first frequency band, such as pulse $P_1$ assigned to a carrier frequency from frequency band $B_1$, may be assigned a value of zero delay intervals $\tau_N$. Likewise, a second pulse assigned to a carrier frequency from a second frequency band, such as pulse $P_2$ assigned to a carrier frequency from frequency band $B_2$, may be assigned a value of i delay intervals $\tau_N$. Finally, a $n^{th}$ pulse assigned to a carrier frequency from a $n^{th}$ frequency band, such as pulse $P_N$ assigned to a carrier frequency from frequency band $B_N$, may be assigned a value of j delay intervals $\tau_N$. However, this example is not limiting, one or more pulses $P_1$ through $P_N$ may be assigned to any suitable value of delay intervals $\tau_N$ without departing from the spirit and scope of the present invention.

When encoding and/or decoding the acoustic communication signal, the transmitter and/or the receiver encodes and/or decodes the acoustic communication signal based upon an amount of one or more time delay intervals $\tau_N$ included within the acoustic communication signal. On the other hand, the transmitter and/or the receiver supplements the transmitted and/or the received one or more time delay intervals $\tau_N$ by factoring in an additional i delay intervals $\tau_N$ when the pulse assigned to a carrier frequency from one of the frequency bands transmitted and/or received prior to one or more time delay intervals $\tau_N$ corresponds to the second pulse assigned to a carrier frequency from the second frequency band. In other words, transmitting and/or receiving the second pulse assigned to the carrier frequency from the second frequency band and waiting and/or measuring m time delay intervals $\tau_N$ is substantially identical to waiting and/or measuring m+i time delay intervals $\tau_N$ for the purposes of encoding and/or decoding the acoustic communication signal. Likewise, the transmitter and/or the receiver supplements the transmitted and/or the received one or more time delay intervals $\tau_N$ by factoring in an additional j delay intervals $\tau_N$ when the pulse assigned to a carrier frequency from one of the frequency bands transmitted and/or received prior to the one or more time delay intervals $\tau_N$ corresponds to the $n^{th}$ pulse assigned to a carrier frequency from the $n^{th}$ frequency band. In other words, transmitting and/or receiving the $n^{th}$ pulse assigned to the carrier frequency from the second frequency band and waiting and/or measuring m time delay intervals $\tau_N$ is substantially identical to waiting and/or measuring m+j time delay intervals $\tau_N$ for the purposes of encoding and/or decoding the acoustic communication signal.

VII. Conclusion

While various embodiments of the present invention have been described above, it should be understood that they have been presented by way of example only, and not limitation. It will be apparent to persons skilled in the relevant art that various changes in form and detail can be made therein without departing from the spirit and scope of the invention. For example, acoustic data communication schemes can be conceived that combine all the techniques above. Thus, the breadth and scope of the present invention should not be limited by any of the above-described exemplary embodiments, but should be defined only in accordance with the following claims and their equivalents.

What is claimed is:

1. A receiver that is communicatively coupled to an ingestible capsule, the receiver comprising:
    a carrier generator configured to select a first and a second carrier frequency that are associated with a first and a second frequency channel, respectively, based on a hopping pattern; and
    a radiating element configured to acoustically receive, from the ingestible capsule, a first portion of data through a body of an animal as an original waveform in accordance with the first carrier frequency for a duration of the first frequency channel,
    wherein the carrier generator is further configured to switch from the first carrier frequency to the second carrier frequency before a reflection of the original waveform is received by the radiating element.

2. The receiver of claim 1, wherein the radiating element is further configured to measure a second portion of the duration of the first frequency channel, the second portion of the duration of the first frequency channel including a number of delay intervals that is associated with a logic value of the first portion of data.

3. The receiver of claim 1, wherein the radiating element is further configured to detect a phase of the first carrier frequency to determine a logic value of the first portion of data.

4. The receiver of claim 1, wherein the radiating element comprises:
    a transducer configured to convert the acoustically received first portion of data to a first portion of an electrical communication signal.

5. The receiver of claim 4, further comprising:
    a filter array configured to receive the first portion of the electrical communication signal and to generate a first portion of a filtered communication signal,
    wherein the filter array comprises a first bandpass filter and a second bandpass filter corresponding to the first frequency channel and the second frequency channel, respectively.

6. The receiver of claim 5, further comprising:
    a demodulator configured to use the first carrier frequency to demodulate or downconvert the first portion of the filtered communication signal and to generate a first portion of a demodulated signal.

7. The receiver of claim 6, further comprising:
    a function generator configured to receive the first portion of the demodulated signal from the demodulator and to generate a first portion of a recovered information signal by decoding the first portion of the demodulated signal.

8. The receiver of claim 1, wherein the receiver is further configured to simultaneously demodulate a plurality of acoustic communication signals.

9. The receiver of claim 1, wherein the receiver is further configured to attach to skin of the body of the animal.

10. The receiver of claim 1, wherein the receiver is further configured to decode the acoustically received first portion of data based on a differential phase shift keying scheme.

11. A receiver that is communicatively coupled to an ingestible capsule, the receiver comprising:
- a radiating element configured to acoustically receive, from the ingestible capsule, a first portion of data through a body of an animal as an original waveform in accordance with a first carrier frequency of a first frequency channel and a second portion of data in accordance with a second carrier frequency of a second frequency channel and to convert the acoustically received first portion of data to a first portion of an electrical communication signal;
- a carrier generator configured to select the first carrier frequency or the second carrier frequency that are associated with the first frequency channel and the second frequency channel, respectively, based on a hopping pattern, and to switch from the first carrier frequency to the second carrier frequency before a reflection of the original waveform is received by the radiating element; and
- a demodulator configured to demodulate and/or downconvert the first portion of the electrical communication signal based on the first carrier frequency and the second portion of the electrical communication signal based on the second carrier frequency.

12. The receiver of claim 11, wherein the radiating element is further configured to measure a second portion of the duration of the first frequency channel, the second portion of the duration of the first frequency channel including a number of delay intervals that is associated with a logic value of the first portion of data.

13. The receiver of claim 11, wherein the radiating element is further configured to detect a phase of the first carrier frequency to determine a logic value of the first portion of data.

14. The receiver of claim 11, wherein the radiating element comprises:
- a transducer configured to convert the acoustically received first portion of data to the first portion of the electrical communication signal.

15. The receiver of claim 14, further comprising:
- a filter array configured to receive the first portion of the electrical communication signal and to generate a filtered communication signal,
- wherein the filter array comprises a first bandpass filter and a second bandpass filter corresponding to the first frequency channel and the second frequency channel, respectively.

16. The receiver of claim 15, wherein the demodulator is further configured to use the first carrier frequency to generate a first portion of a demodulated signal based on a differential phase shift keying scheme.

17. The receiver of claim 16, further comprising:
- a function generator configured to receive the first portion of the demodulated signal from the demodulator and to generate a first portion of a recovered information signal by decoding the first portion of the demodulated signal.

18. The receiver of claim 11, wherein the receiver is further configured to simultaneously demodulate a plurality of acoustic communication signals.

19. The receiver of claim 11, wherein the receiver is further configured to attach to skin of the body of the animal.

20. The receiver of claim 11, wherein the receiver is further configured to decode the acoustically received first portion of data based on a differential phase shift keying scheme.

* * * * *